(12) United States Patent
Masuyama et al.

(10) Patent No.: US 8,475,999 B2
(45) Date of Patent: Jul. 2, 2013

(54) COMPOUND AND PHOTORESIST COMPOSITION CONTAINING THE SAME

(75) Inventors: Tatsuro Masuyama, Toyonaka (JP); Mitsuhiro Hata, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 114 days.

(21) Appl. No.: 12/852,237

(22) Filed: Aug. 6, 2010

(65) Prior Publication Data

US 2011/0039209 A1    Feb. 17, 2011

(30) Foreign Application Priority Data

Aug. 11, 2009    (JP) ................................ 2009-186906

(51) Int. Cl.
    *G03C 1/00*    (2006.01)
(52) U.S. Cl.
    USPC ..................................... 430/283.1; 430/270.1
(58) Field of Classification Search
    USPC ................... 430/270.1; 546/194; 560/19, 24, 560/157; 548/563, 533
    See application file for complete search history.

(56) References Cited

U.S. PATENT DOCUMENTS

| | | | |
|---|---|---|---|
| 6,399,272 | B1 | 6/2002 | Lee et al. |
| 2001/0023050 | A1 | 9/2001 | Numata et al. |
| 2003/0194639 | A1 | 10/2003 | Miya et al. |
| 2006/0194982 | A1 | 8/2006 | Harada et al. |
| 2009/0068594 | A1 | 3/2009 | Shimbori |
| 2011/0039209 | A1 | 2/2011 | Masuyama et al. |

FOREIGN PATENT DOCUMENTS

| | | |
|---|---|---|
| JP | 6-148887 A | 5/1994 |
| JP | 7-333851 A | 12/1995 |
| JP | 2001-166476 A | 6/2001 |
| JP | 2008-249993 A | 10/2008 |
| JP | 2009-199021 A | 9/2009 |

OTHER PUBLICATIONS

Aoshima et al., "Synthesis of Photolabile Caged Amino Acids for Measuring Amino Acid Transporters", Jan. 14, 1992, Bioscience, Biotechnology, and Biochemistry, 56 (7), 1086-1089.*

* cited by examiner

*Primary Examiner* — Cynthia Kelly
*Assistant Examiner* — Anna Conlin
(74) *Attorney, Agent, or Firm* — Birch, Stewart, Kolasch & Birch, LLP

(57) ABSTRACT

The present invention provides a compound represented by the formula (C1):

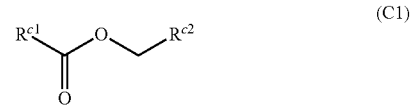

(C1)

wherein $R^{c2}$ represents a C6-C10 aromatic hydrocarbon group having at least one nitro group and $R^{c1}$ represents a group represented by the formula (1):

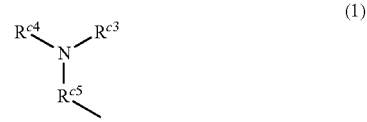

(1)

wherein $R^{c4}$ represents a hydrogen atom etc., $R^{c5}$ represents a C1-C30 divalent hydrocarbon group, and $R^{c3}$ represents a group represented by the formula (3-1), (3-2) or (3-3):

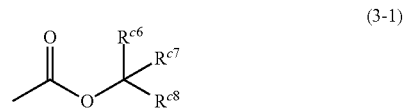

(3-1)

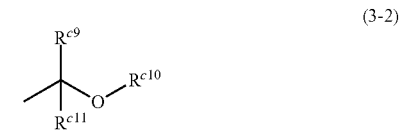

(3-2)

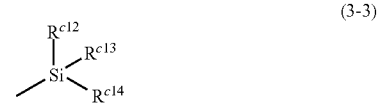

(3-3)

wherein $R^{c6}$, $R^{c7}$, $R^{c8}$, $R^{c9}$, $R^{c10}$, $R^{c11}$, $R^{c12}$, $R^{c13}$ and $R^{c14}$ each independently represent a C1-C30 hydrocarbon group, and a photoresist composition comprising a resin, an acid generator and the compound represented by the formula (C1).

5 Claims, No Drawings

COMPOUND AND PHOTORESIST COMPOSITION CONTAINING THE SAME

This nonprovisional application claims priority under 35 U.S.C. §119(a) on Patent Application No. 2009-186906 filed in JAPAN on Aug. 11, 2009, the entire contents of which are hereby incorporated by reference.

FIELD OF THE INVENTION

The present invention relates to a novel compound and a photoresist composition containing the same.

BACKGROUND OF THE INVENTION

A photoresist composition used for semiconductor microfabrication employing a lithography process contains an acid generator comprising a compound generating an acid by irradiation.

US 2003/0194639 A1 discloses a photoresist composition comprising 2,6-diisopropylaniline or tetrabutylammonium hydroxide.

SUMMARY OF THE INVENTION

The present invention is to provide a novel compound and a photoresist composition containing the same.

The present invention relates to the followings:

<1> A compound represented by the formula (C1):

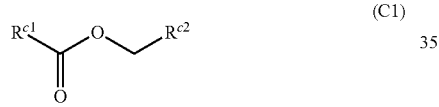

(C1)

wherein $R^{c2}$ represents a C6-C10 aromatic hydrocarbon group having at least one nitro group and the aromatic hydrocarbon group can have one or more substituents other than a nitro group, and $R^{c1}$ represents a group represented by the formula (1):

(1)

wherein $R^{c4}$ represents a hydrogen atom, or a linear, branched chain or cyclic C1-C6 aliphatic hydrocarbon group, $R^{c5}$ represents a C1-C30 divalent hydrocarbon group which can have one or more substituents selected from the group consisting of a halogen atom, a hydroxyl group, a mercapto group (—SH), an amino group and a carbamoyl group (—CONH$_2$), and one or more —CH$_2$— in the divalent hydrocarbon group can be replaced by —O—, —CO—, —S— or —NR$^{c15}$— in which R$^{c15}$ represents a hydrogen atom or a linear or branched chain C1-C4 alkyl group, and one or more —CH= in the divalent hydrocarbon group can be replaced by —N=, and $R^{c4}$ and $R^{c5}$ can be bonded each other to form a ring together with the nitrogen atom to which $R^{c4}$ and $R^{c5}$ are bonded, and $R^{c3}$ represents a group represented by the formula (3-1), (3-2) or (3-3):

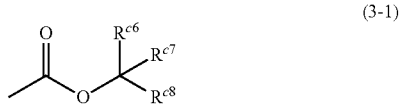

(3-1)

(3-2)

(3-3)

wherein $R^{c6}$, $R^{c7}$, $R^{c8}$, $R^{c9}$, $R^{c10}$, $R^{c11}$, $R^{c12}$, $R^{c13}$ and $R^{c14}$ each independently represent a C1-C30 hydrocarbon group which can have one or more hydroxyl groups, and one or more —CH$_2$— in the C1-C30 hydrocarbon group can be replaced by —O—, —CO—, —S— or —NR$^{c16}$— in which $R^{c16}$ represents a hydrogen atom or a linear or branched chain C1-C4 alkyl group, and $R^{c6}$ and $R^{c7}$ can be bonded each other to form a ring together with the carbon atom to which $R^{c6}$ and $R^{c7}$ are bonded, and $R^{c9}$ and $R^{c10}$ can be bonded each other to form a ring together with the carbon atom to which $R^{c9}$ is bonded and the oxygen atom to which $R^{c10}$ is bonded;

<2> The compound according to <1>, wherein $R^{c2}$ is a nitrophenyl group;

<3> The compound according to <1> or <2>, wherein $R^{c3}$ is a group represented by the formula (3-1);

<4> The compound according to any one of <1> to <3>, wherein $R^{c1}$ is a group represented by the formula (1-1) or (1-2):

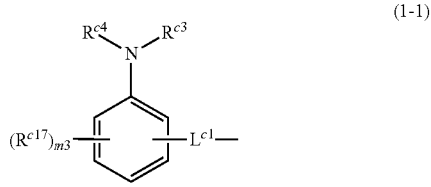

(1-1)

(1-2)

wherein $R^{c3}$ and $R^{c4}$ are the same as defined in <1>, and $R^{c17}$ is independently in each occurrence a C1-C10 hydrocarbon group which can have one or more hydroxyl groups, and one or more —CH$_2$— in the C1-C10 hydrocarbon group can be replaced by —O—, —CO—, —S— or —NR$^{c19}$— in which $R^{c19}$ represents a hydrogen atom or a linear or branched chain C1-C4 alkyl group, m3 represents an integer of 0 to 4, and $L^{c1}$ represents a single bond or a linear C1-C4 alkanediyl group, $R^{c18}$ represents a hydrogen atom, a linear, branched chain or cyclic C1-C15 aliphatic hydrocarbon group or a C7-C15 aralkyl group, and one or more —CH$_2$— in the aliphatic hydrocarbon group and the aralkyl group can be replaced by —O—, —CO— or —S—, and the aliphatic hydrocarbon group and the aralkyl group can have one or more substituents selected from the group consisting of a halogen atom, a hydroxyl group, a mercapto group (—SH), an amino group and a carbamoyl group (—CONH$_2$), and R$^{c4}$ and R$^{c18}$ can be bonded each other to form a ring together with the carbon atom to which R$^{c18}$ is bonded and the nitrogen atom to which R$^{c4}$ is bonded;

<5> The compound according to any one of <1> to <4>, wherein the compound represented by the formula (C1) is a compound represented by the formula (C1-1), (C1-2), (C1-3) or (C1-4):

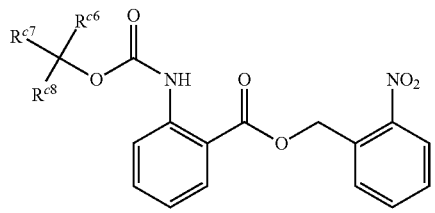
(C1-1)

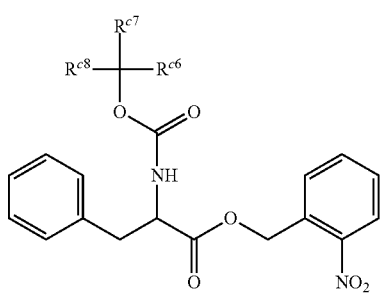
(C1-2)

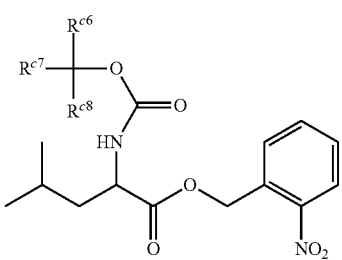
(C1-3)

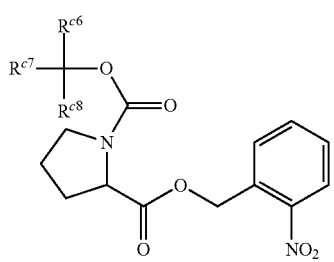
(C1-4)

wherein R$^{c6}$, R$^{c7}$ and R$^{c8}$ are the same meanings as defined in <1>;

<6> A photoresist composition comprising a resin, an acid generator and a compound according to any one of <1> to <5>;

<7> A process for producing a compound represented by the formula (C1):

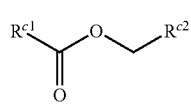
(C1)

wherein R$^{c2}$ represents a C6-C10 aromatic hydrocarbon group having at least one nitro group and the aromatic hydrocarbon group can have one or more substituents other than a nitro group, and R$^{c1}$ represents a group represented by the formula (1):

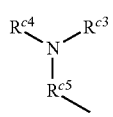
(1)

wherein R$^{c4}$ represents a hydrogen atom, or a linear, branched chain or cyclic C1-C6 aliphatic hydrocarbon group, R$^{c5}$ represents a C1-C30 divalent hydrocarbon group which can have one or more substituents selected from the group consisting of a halogen atom, a hydroxyl group, a mercapto group (—SH), an amino group and a carbamoyl group (—CONH$_2$), and one or more —CH$_2$— in the divalent hydrocarbon group can be replaced by —O—, —CO—, —S— or —NR$^{c15}$— in which R$^{c15}$ represents a hydrogen atom or a linear or branched chain C1-C4 alkyl group, and one or more —CH= in the divalent hydrocarbon group can be replaced by —N=, and R$^{c4}$ and R$^{c5}$ can be bonded each other to form a ring together with the nitrogen atom to which R$^{c4}$ and R$^{c5}$ are bonded, and R$^{c3}$ represents a group represented by the formula (3-1), (3-2) or (3-3):

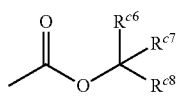
(3-1)

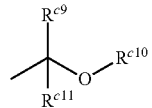
(3-2)

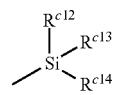
(3-3)

wherein R$^{c6}$, R$^{c7}$, R$^{c8}$, R$^{c9}$, R$^{c10}$, R$^{c11}$, R$^{c12}$, R$^{c13}$ and R$^{c14}$ each independently represent a C1-C30 hydrocarbon group which can have one or more hydroxyl groups, and one or more —CH$_2$— in the C1-C30 hydrocarbon group can be replaced by —O—, —CO—, —S— or —NR$^{c16}$— in which R$^{c16}$ represents a hydrogen atom or a linear or branched chain C1-C4 alkyl group, and R$^{c6}$ and R$^{c7}$ can be bonded each other to form a ring together with the carbon atom to which R$^{c6}$ and R$^{c7}$ are bonded, and R$^{c9}$ and R$^{c10}$ can be bonded each other to form a ring together with the carbon atom to which R$^{c9}$ is bonded and the oxygen atom to which R$^{c10}$ is bonded, comprising reacting a compound represented by the formula (C1a):

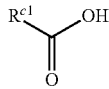
(C1a)

wherein $R^{c1}$ is the same meaning as defined above, or a salt thereof with a compound represented by the formula (C1b):

(C1b)

wherein $R^{c2}$ is the same meaning as defined above and X represents a chlorine atom, a bromine atom or an iodine atom.

DESCRIPTION OF PREFERRED EMBODIMENTS

The compound of the present invention is represented by the formula (C1):

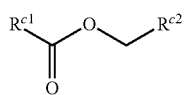
(C1)

(hereinafter, simply referred to as the compound (C1)).

The compound (1) has an amino group protected with an acid-leaving group and a specific structure represented by $R^{c2}$—$CH_2$—O—CO—. The photoresist composition comprising the compound (C1) gives a photoresist pattern having a good Mask Error Enhancement Factor (MEEF).

In this specification, "acid-leaving group" means a group capable of leaving from an amino group by the action of an acid generated from an acid generator. Because the acid-leaving group bonds to the amino group, the basicity of the amino group protected with an acid-leaving group in the compound (C1) becomes lower than a free amino group, and when an acid generated from an acid generator is contacted with the amino group protected with an acid-leaving group, the acid-leaving group leaves to form a free amino group. Therefore, the compound (1) acts as a quencher in the photoresist composition because it reacts with an excess acid generated from the acid generator.

In the formula (C1), $R^{c1}$ represents a group represented by the formula (1):

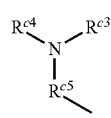
(1)

(hereinafter, simply referred to as the group (1)), and the group (1) has an amino group protected with an acid-leaving group $R^{c3}$. $R^{c3}$ represents a group represented by the formula (3-1), (3-2) or (3-3):

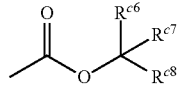
(3-1)

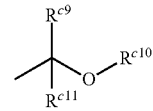
(3-2)

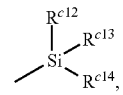
(3-3)

and

The group represented by the formula (3-1) is preferable.

$R^{c6}$, $R^{c7}$, $R^{c8}$, $R^{c9}$, $R^{c10}$, $R^{c11}$, $R^{c12}$, $R^{c13}$ and $R^{c14}$ each independently represent a C1-C30 hydrocarbon group which can have one or more hydroxyl groups. Examples of the C1-C30 hydrocarbon group include a linear, branched chain or cyclic C1-C30 hydrocarbon group and a C6-C30 aromatic hydrocarbon group, and the aliphatic hydrocarbon group may be a saturated or unsaturated aliphatic hydrocarbon group. Examples of the linear aliphatic hydrocarbon group include a linear C1-C30 alkyl group such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, a tetracosyl group, a pentacosyl group, a hexacosyl group, a heptacosyl group, an octacosyl group, a nonacosyl group and a triacontyl group. Among them, a linear C1-C4 alkyl group is preferable.

Examples of the branched chain hydrocarbon group include a branched chain C3-C30 alkyl group such as an isopropyl group, an isobutyl group, a sec-butyl group, a tert-butyl group, a 2-methylpentyl group, a 2-ethylpentyl group, a 2-methylhexyl group, a 2-ethylhexyl group, a 2-propylhexyl group and a 1,1-dimethylhexyl group, and among them, an isopropyl group, a sec-butyl group, a tert-butyl group and a 2-ethylhexyl group are preferable.

Examples of the cyclic hydrocarbon group include a monocyclic hydrocarbon group such as a C3-C30 cycloalkyl group, and a polycyclic hydrocarbon group such as a bridged cyclic hydrocarbon group. Examples of the cycloalkyl group include a C3-C30 cycloalkyl group such as a cyclopropyl group, a cyclobutyl group, a cyclopentyl group, a cyclohexyl group, a cycloheptyl group and a cyclooctyl group. Examples of the bridged cyclic hydrocarbon group include a norbornyl group, a bicycle[2.2.2]octyl group, a 1-adamantyl group, a 2-adamantyl group, the following groups having a structure condensed two or more rings such as a norbornane ring:

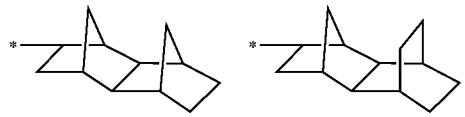

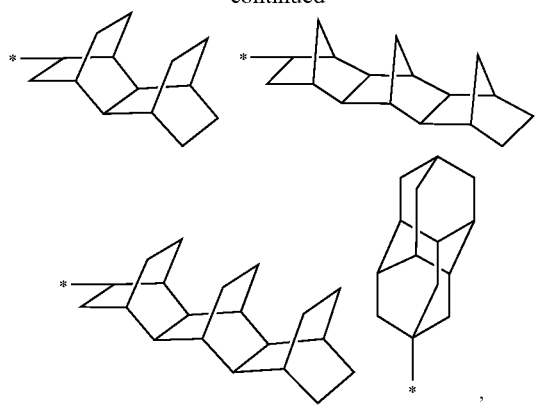

and a group formed by combining a linear hydrocarbon group with a cyclic hydrocarbon group such as the followings.

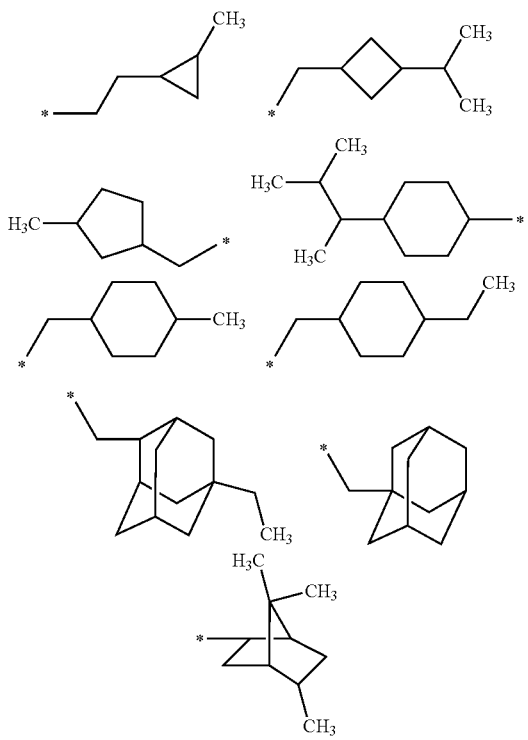

In the above formulae and the following formulae, * represents a binding position to an adjacent atom.

Examples of the aromatic hydrocarbon group include a phenyl group, a phenyl group having one or more alkyl groups such as a 4-methylphenyl group and a 3,4-dimethylphenyl group, a 1-naphthyl group and a 2-naphthyl group.

The C1-C30 hydrocarbon group may be a group formed by combining an aliphatic hydrocarbon group with an aromatic hydrocarbon group such as an aralkyl group such as a benzyl group.

One or more —$CH_2$— in the C1-C10 hydrocarbon group, preferably in the alicyclic hydrocarbon group, can be replaced by —O—, —CO—, —S— or —$NR^{c16}$— in which $R^{c16}$ represents a hydrogen atom or a linear or branched chain C1-C4 alkyl group. Examples of the hydrocarbon group in which one or more —$CH_2$— are replaced by —O— include the followings.

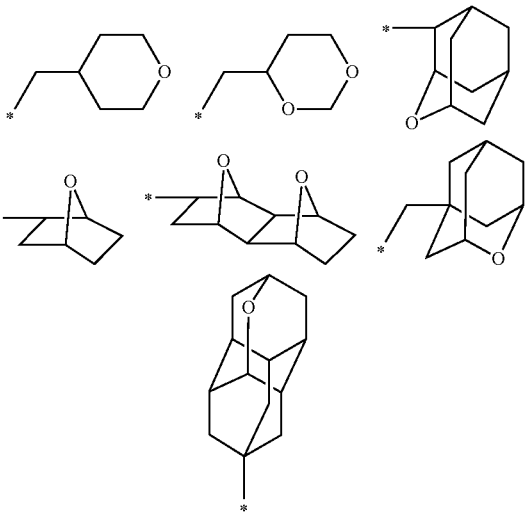

Examples of the hydrocarbon group in which one or more —$CH_2$— are replaced by —CO— include the followings.

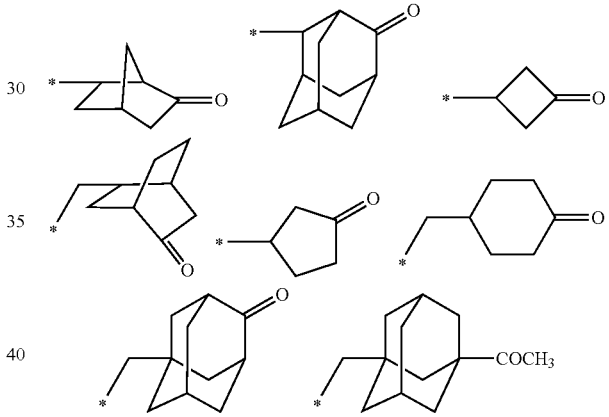

Examples of the hydrocarbon group in which one or more —$CH_2$— are replaced by —S— include the followings.

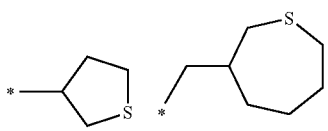

Examples of the hydrocarbon group in which one or more —$CH_2$— are replaced by —$NR^{c16}$— include the followings.

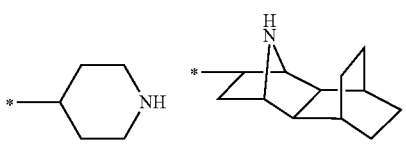

The C1-C30 hydrocarbon group which can have one or more hydroxyl groups, and examples the hydrocarbon group having one or more hydroxyl groups include the followings.

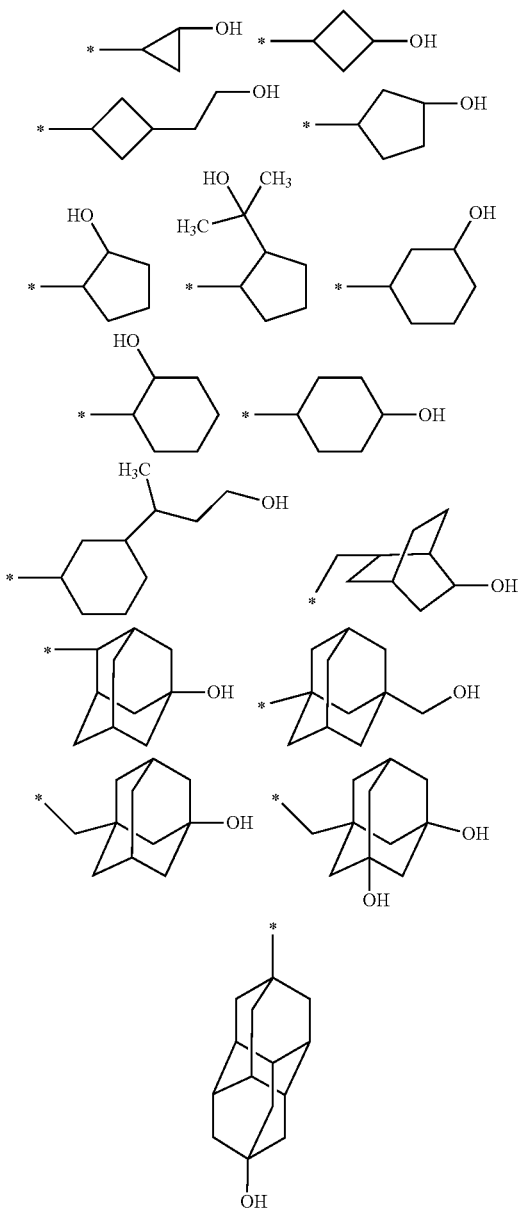

$R^{c6}$ and $R^{c7}$ can be bonded each other to form a ring together with the carbon atom to which $R^{c6}$ and $R^{c7}$ are bonded. The ring may be a monocycle such as a cycloalkane ring, and a polycycle such as a bridged hydrocarbon ring. Examples thereof include a cyclopropane ring, a cyclobutane ring, a cyclopentane ring, a cyclohexane ring, a cycloheptane ring, a cyclooctane ring, an or bornane ring, a bicyclo[2.2.2] octane ring, an adamantane ring and the followings.

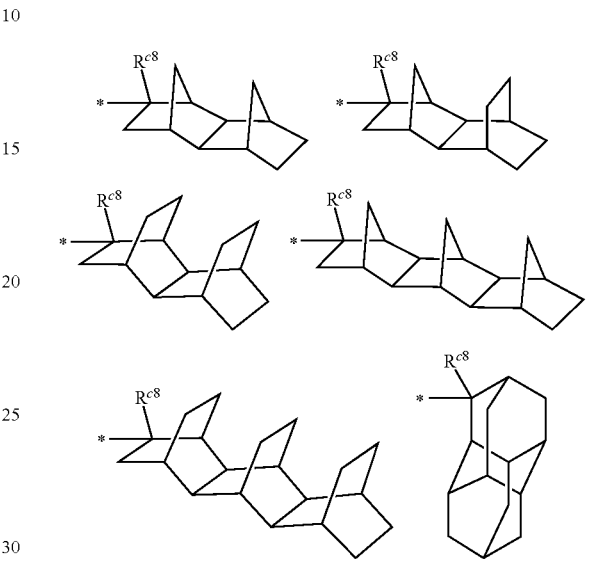

$R^{c9}$ and $R^{c10}$ can be bonded each other to form a ring together with the carbon atom to which $R^{c9}$ is bonded and the oxygen atom to which $R^{c10}$ is bonded, and preferable examples the ring include an oxolane ring, which is a five-membered ring containing an oxygen atom, and an oxane ring, which is a six-membered ring containing an oxygen atom, and specific examples thereof include the followings.

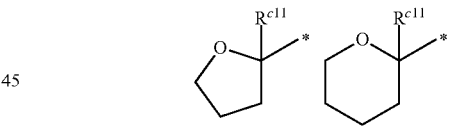

Other examples of the C1-C30 hydrocarbon group include the followings.

Examples of the group represented by the formula (3-1) include the followings.

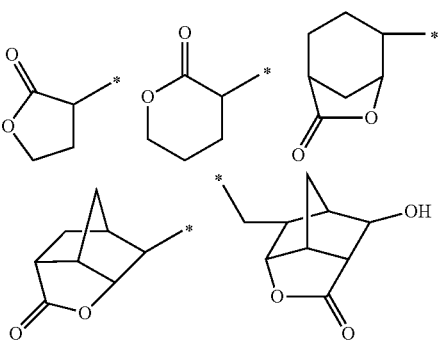

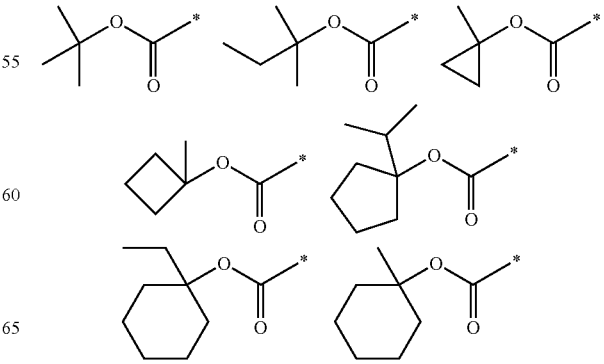

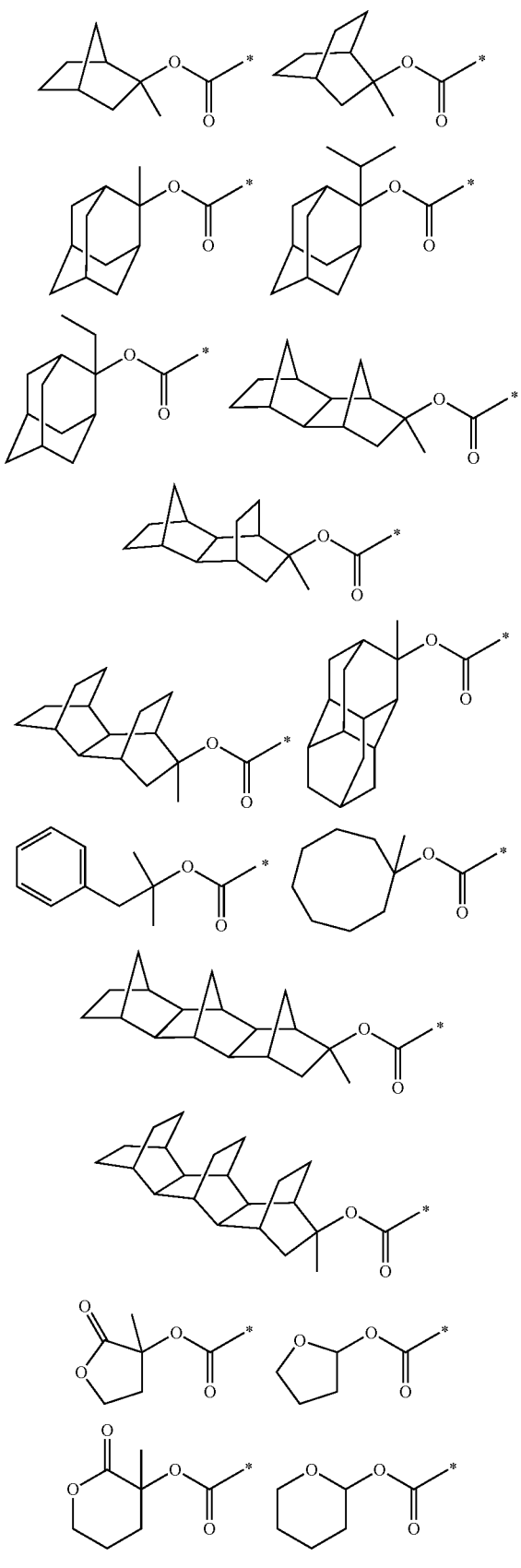

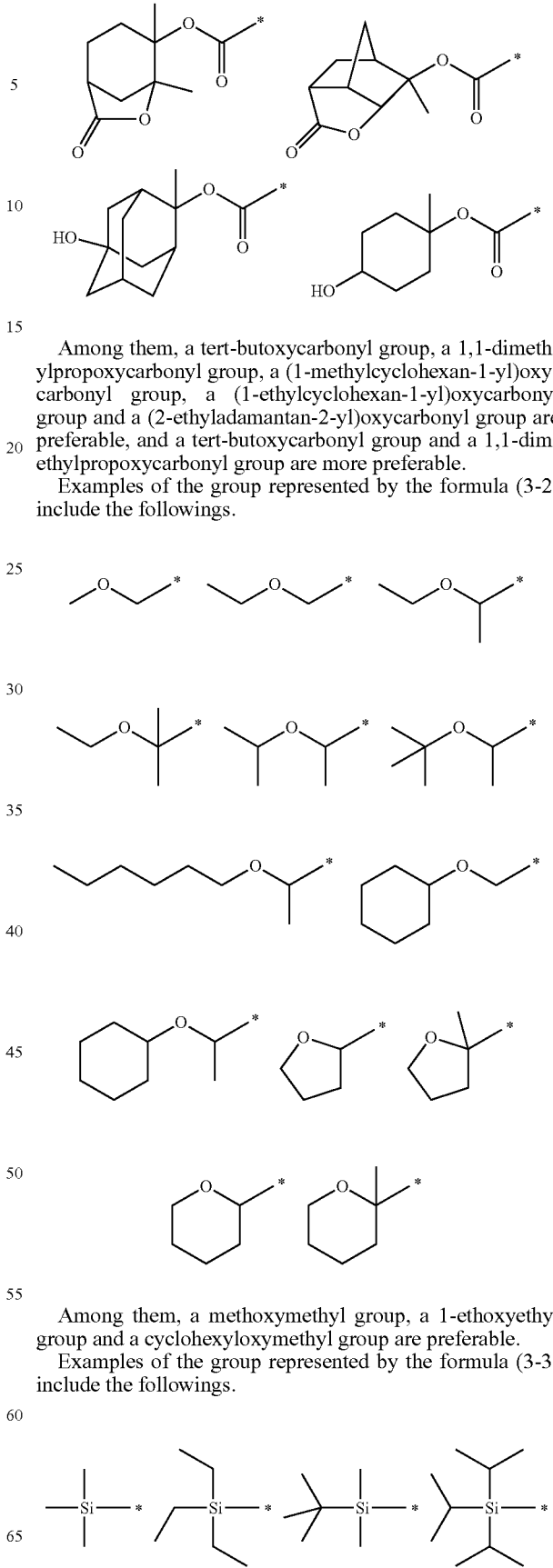

Among them, a tert-butoxycarbonyl group, a 1,1-dimethylpropoxycarbonyl group, a (1-methylcyclohexan-1-yl)oxycarbonyl group, a (1-ethylcyclohexan-1-yl)oxycarbonyl group and a (2-ethyladamantan-2-yl)oxycarbonyl group are preferable, and a tert-butoxycarbonyl group and a 1,1-dimethylpropoxycarbonyl group are more preferable.

Examples of the group represented by the formula (3-2) include the followings.

Among them, a methoxymethyl group, a 1-ethoxyethyl group and a cyclohexyloxymethyl group are preferable.

Examples of the group represented by the formula (3-3) include the followings.

-continued

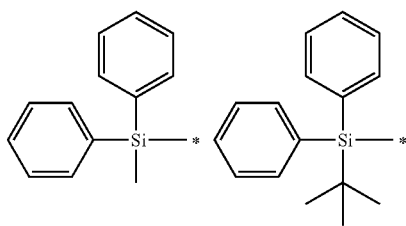

Among them, a trimethylsilyl group and a diphenylmethylsilyl group are preferable.

$R^{c4}$ represents a hydrogen atom, or a linear, branched chain or cyclic C1-C6 aliphatic hydrocarbon group. Examples of the C1-C6 aliphatic hydrocarbon group include a methyl group, an ethyl group, a propyl group, an isopropyl group, a butyl group, an isobutyl group, a pentyl group, a hexyl group, a cyclopentyl group and a cyclohexyl group. $R^{c4}$ is preferably a hydrogen atom, a methyl group or an ethyl group, and is more preferably a hydrogen atom.

$R^{c5}$ represents a C1-C30 divalent hydrocarbon group which can have one or more substituents selected from the group consisting of a halogen atom, a hydroxyl group, a mercapto group (—SH), an amino group and a carbamoyl group (—CONH$_2$). One or more —CH$_2$— in the divalent hydrocarbon group can be replaced by —O—, —CO—, —S— or —NR$^{c15}$— in which R$^{c15}$ represents a hydrogen atom or a linear or branched chain C1-C4 alkyl group, and one or more —CH= in the divalent hydrocarbon group can be replaced by —N=.

Examples of the C1-C30 divalent hydrocarbon group include a divalent linear or branched chain aliphatic hydrocarbon group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a divalent hydrocarbon group containing a cyclic structure such as the followings:

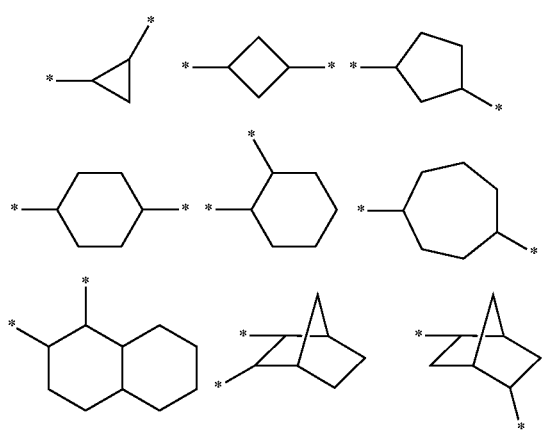

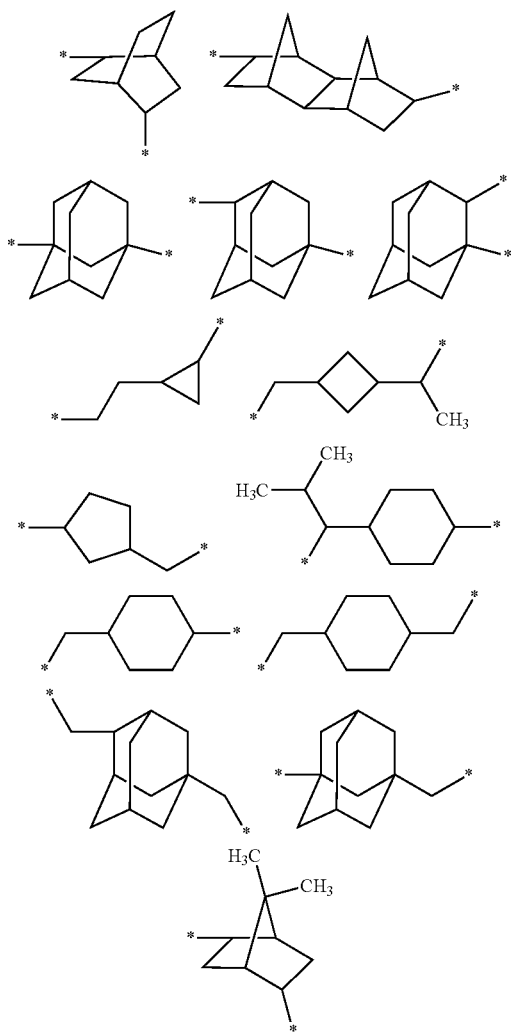

and a divalent aromatic hydrocarbon group such as the followings.

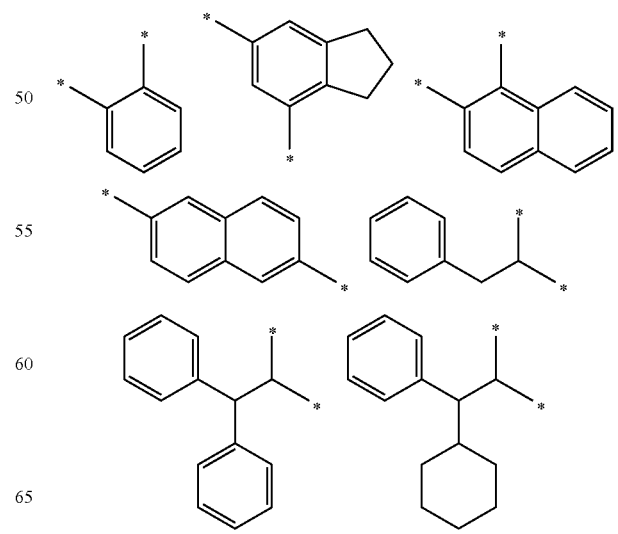

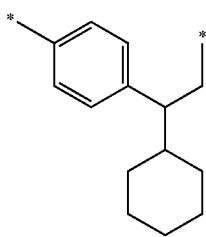

Examples of the C1-C30 divalent hydrocarbon group in which one or more —CH$_2$— are replaced by —O—, —S— or —NR$^{c15}$— include the followings.

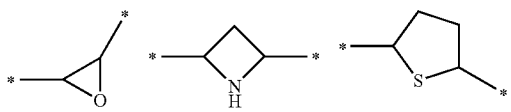

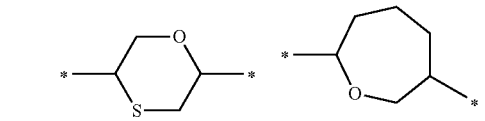

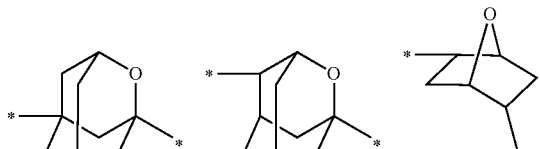

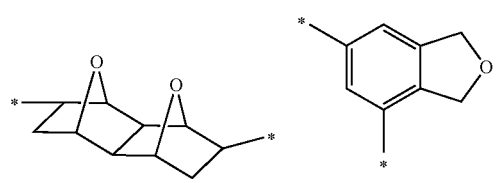

Examples of the C1-C30 divalent hydrocarbon group in which one or more —CH$_2$— are replaced by —CO— include the followings.

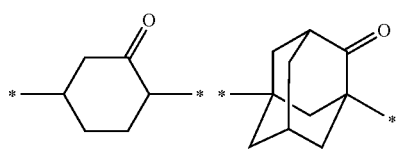

Examples of the C1-C30 divalent hydrocarbon group in which one or more —CH= are replaced by —N= include the followings.

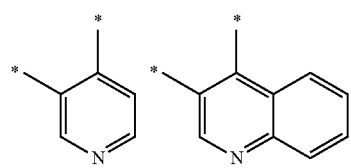

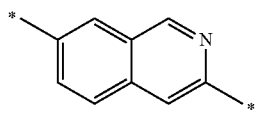

R$^{c4}$ and R$^{c5}$ can be bonded each other to form a ring together with the nitrogen atom to which R$^{c4}$ and R$^{c5}$ are bonded, and the ring can have a linear, branched chain or cyclic aliphatic hydrocarbon group as a side chain, and the ring may be a condensed ring such as a octahydroisoindole ring. Preferably examples of the ring include a five-membered saturated nitrogen-containing heteroring, a six-membered saturated nitrogen-containing heteroring and a seven-membered saturated nitrogen-containing heteroring, and a pyrrolidine ring and a piperidine ring are more preferable, and a pyrrolidine ring is especially preferable.

R$^{c1}$ is preferably a group represented by the formula (1-1), (1-2) or (1-3)

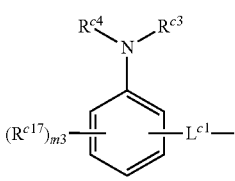

(1-1)

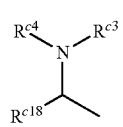

(1-2)

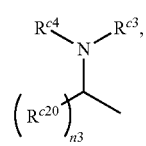

(1-3)

is more preferably a group represented by the formula (1-1) or (1-2), and especially preferably a group represented by the formula (1-2).

In the formulae (1-1) to (1-3), R$^{c3}$ and R$^{c4}$ are the same as defined above. L$^{c1}$ represents a single bond or a linear C1-C4 alkanediyl group, and preferably a single bond or a methylene group, and more preferably a single bond.

In the formula (1-1), R$^{c17}$ is independently in each occurrence a C1-C10 hydrocarbon group which can have one or more hydroxyl groups, and one or more —CH$_2$— in the C1-C10 hydrocarbon group can be replaced by —O—, —CO—, —S— or —NR$^{c19}$— in which R$^{c19}$ represents a hydrogen atom or a linear or branched chain C1-C4 alkyl group. Examples thereof include the same as described above. In the formula (1-1), when m3 is 0, R$^{c17}$ is nonexistent, and m3 is preferably 0 or 1, and more preferably 0. Examples of R$^{c17}$ include an alkyl group such as a heptyl group, an isopropyl group and a cylohexyl group, an alkylcarbonyl group, an alkoxy group, an alkylcarbonyloxy group and an alkylcarbonylimino group. Examples of the alkylcarbonyl group include the followings.

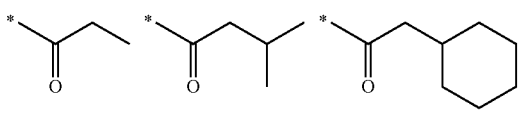

Examples of the alkoxy group include the followings.

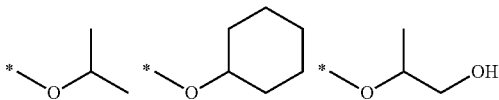

Examples of the alkylcarbonyloxy group include the followings.

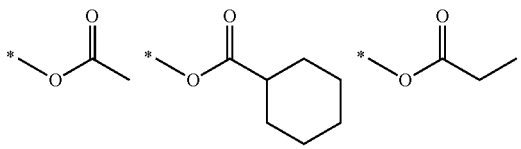

Examples of the alkylcarbonylimino group include the followings.

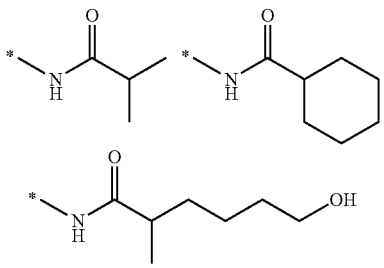

$R^{c17}$ is preferably a linear or branched chain C1-C4 alkyl group or a (C1-C4 alkyl)carbonyloxy group.

In the formula (1-2), $R^{c18}$ represents a hydrogen atom, a linear, branched chain or cyclic C1-C15 aliphatic hydrocarbon group or a C7-C15 aralkyl group. Examples of the aliphatic hydrocarbon group include a methyl group, an ethyl group, a propyl group, an isopropyl group, a butyl group, an isobutyl group, a pentyl group, a hexyl group, a cyclopentyl group, a cyclohexyl group, a 2-cyclohexylethyl group and dicyclohexylmethyl group. Examples of the aralkyl group include a benzyl group and a 2-phenylethyl group. The aliphatic hydrocarbon group and the aralkyl group can have one or more substituents selected from the group consisting of a halogen atom, a hydroxyl group, a mercapto group (—SH), an amino group and a carbamoyl group (—CONH$_2$), and examples of the aliphatic hydrocarbon group and the aralkyl group having one or more substituents include a hydroxymethyl group, a 2-hydroxyethyl group, a mercaptomethyl group, a 2-mercaptoethyl group, a (4-hydroxyphenyl)methyl group, a 2-carbamoylethyl group (—C$_2$H$_5$—CONH$_2$). One or more —CH$_2$— in the aliphatic hydrocarbon group and the aralkyl group can be replaced by —O—, —CO— or —S—, and examples of the aliphatic hydrocarbon group and the aralkyl group in which one or more —CH$_2$— are replaced by —O—, —CO— or —S— include a 2-methoxycarbonylethyl group (—C$_2$H$_5$—CO—O—CH$_3$) and a 2-(methylthio) ethyl group (—C$_2$H$_5$—S—CH$_3$). $R^{c18}$ is preferably an isobutyl group or a benzyl group.

$R^{c4}$ and $R^{c18}$ can be bonded each other to form a ring together with the carbon atom to which $R^{c18}$ is bonded and the nitrogen atom to which $R^{c4}$ is bonded, and the ring can have a linear, branched chain or cyclic aliphatic hydrocarbon group as a side chain, and the ring may be a condensed ring such as a octahydroisoindole ring. Preferably examples of the ring include a five-membered saturated nitrogen-containing heteroring, a six-membered saturated nitrogen-containing heteroring and a seven-membered saturated nitrogen-containing heteroring, and a pyrrolidine ring and a piperidine ring are more preferable, and a pyrrolidine ring is especially preferable.

In the formula (1-3), $R^{c20}$ is independently in each occurrence a hydrogen atom, or a linear, branched chain or cyclic C1-C15 aliphatic hydrocarbon group, and one or more —CH$_2$— in the aliphatic hydrocarbon group can be replaced by —O—, —CO—, —S— or —NH—, n3 represents 2 or 3, and $R^{c4}$ and any one of ($R^{c20}$)s can be bonded each other to form a ring together with the carbon atom to which $R^{c20}$ is bonded and the nitrogen atom to which $R^{c4}$ is bonded, and any two of ($R^{c20}$)s can be bonded each other to form a ring together with the carbon atoms to which ($R^{c20}$)s are bonded. Examples of the aliphatic hydrocarbon group include the same as described above. Examples of the aliphatic hydrocarbon group in which one or more —CH$_2$— are replaced by —O—, —CO—, —S— or —NH— include a 3-(ethoxyimino)propyl group. The ring formed by combining $R^{c4}$ and any one of ($R^{c20}$)s can have a linear, branched chain or cyclic aliphatic hydrocarbon group as a side chain, and the ring may be a condensed ring such as a octahydroisoindole ring. Preferably examples of the ring include a five-membered saturated nitrogen-containing heteroring, a six-membered saturated nitrogen-containing heteroring and a seven-membered saturated nitrogen-containing heteroring. Examples of the ring formed by combining any two of ($R^{c20}$)s include a cyclohexane ring, a decahydronaphthalene ring and an adamantane ring.

In the formula (C1), $R^{c2}$ represents a C6-C10 aromatic hydrocarbon group having at least one nitro group and the aromatic hydrocarbon group can have one or more substituents other than a nitro group. As the substituent other than a nitro group, an electron-withdrawing group other than a nitro group is preferable, and examples thereof include a perfluoroalkyl group, a perchloroalkyl group, a cyano group and an alkoxycarbonyl group. The aromatic hydrocarbon group can have a weak electron-donating group such as an alkyl group such as a methyl group, an ethyl group, a propyl group and a butyl group.

Examples of $R^{c2}$ include a nitrophenyl group, a dinitrophenyl group, a methylnitrophenyl group, a dimethylnitrophenyl group, an ethylnitrophenyl group, a propylnitrophenyl group, a butylnitrophenyl group and a nitronaphthyl group, and a nitrophenyl group is preferable, and a 2-nitrophenyl group and a 4-nitrophenyl group are more preferable, and a 2-nitrophenyl group is especially preferable.

Among the compound (C1), the compound wherein $R^{c1}$ is the group represented by the formula (1-1) or (1-2), $R^{c2}$ is a nitrophenyl group, and $R^{c3}$ is the group represented by the formula (3-1) is preferable, and the following compounds represented by the formulae (C1-1), (C1-2), (C1-3) and (C1-4):

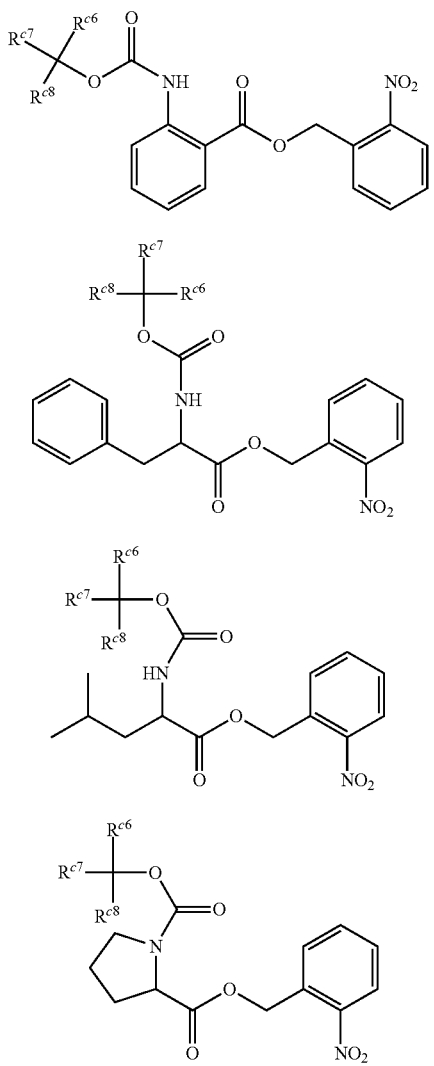
(C1-1)
(C1-2)
(C1-3)
(C1-4)
wherein $R^{c6}$, $R^{c7}$ and $R^{c8}$ are the same meanings as defined above.
Examples of the compound wherein $R^{c1}$ is the group represented by the formula (1-1) and $R^{c2}$ is a nitrophenyl group include the followings.
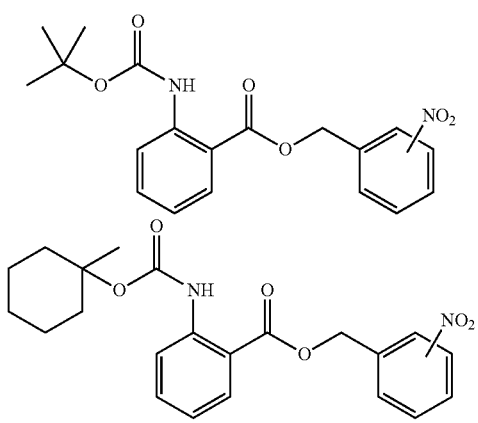
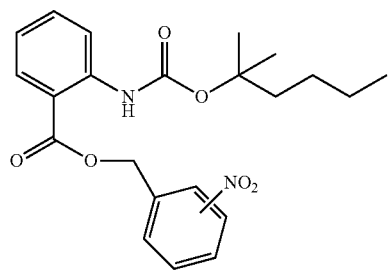
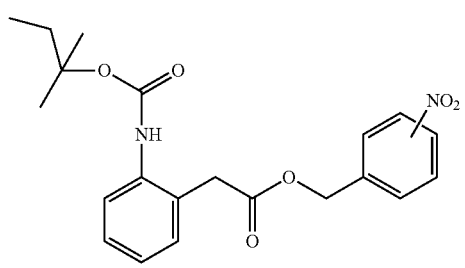
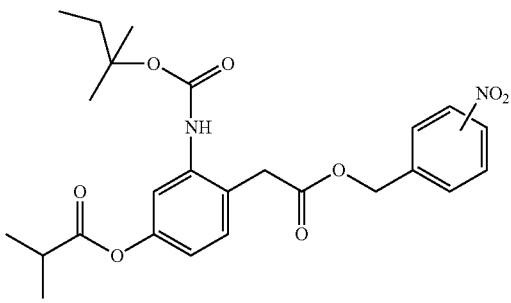
Examples of the compound wherein $R^{c1}$ is the group represented by the formula (1-2) and $R^{c2}$ is a nitrophenyl group include the followings.
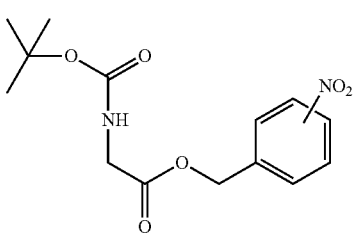
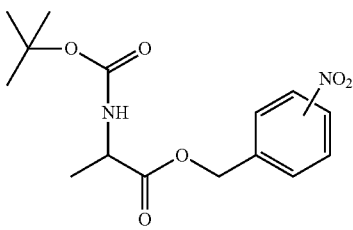
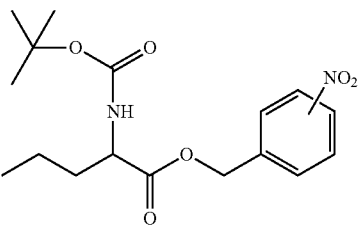

21
-continued
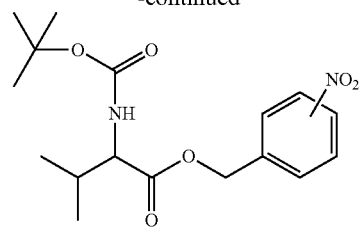
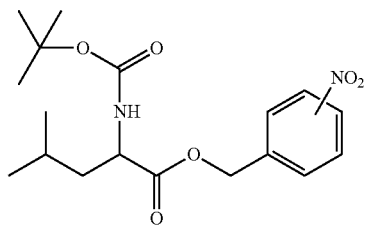
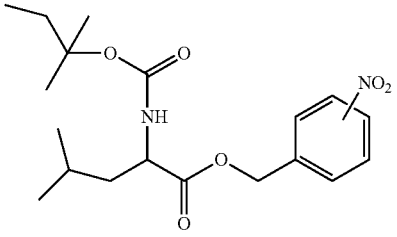
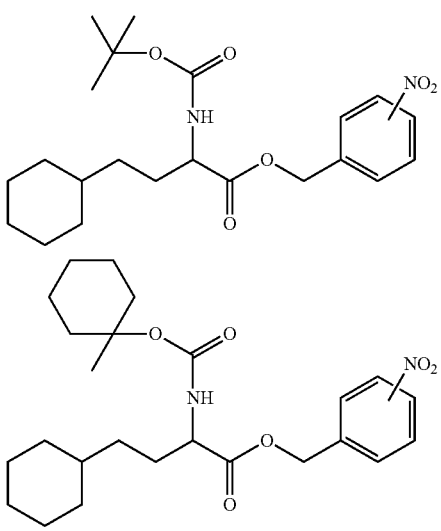
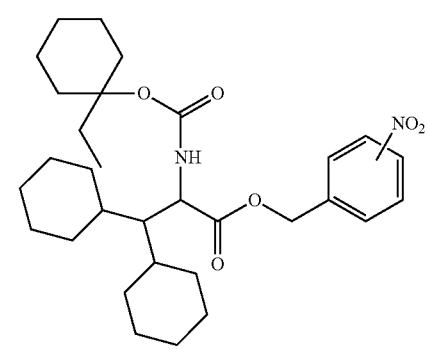
22
-continued
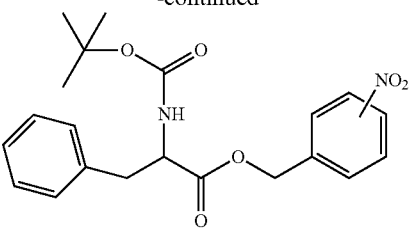
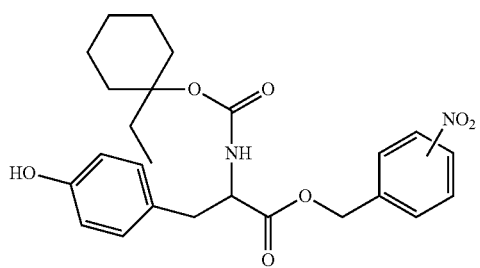
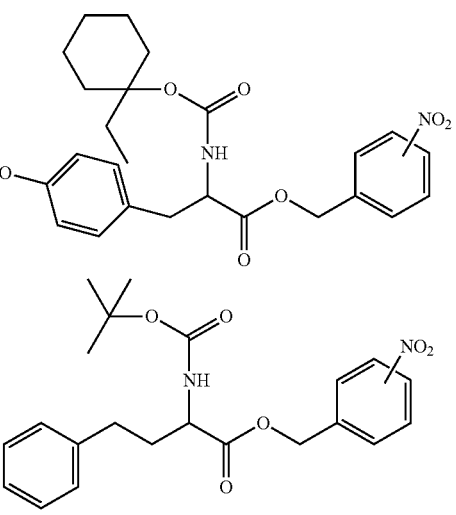
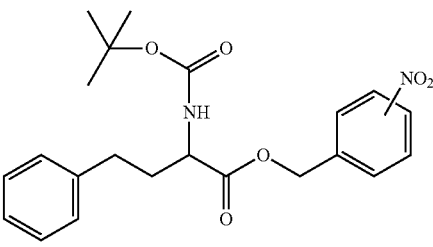
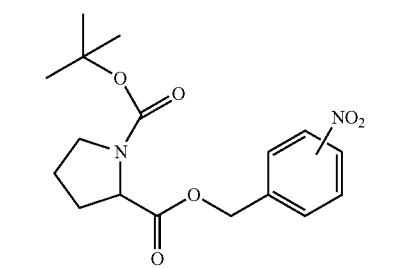
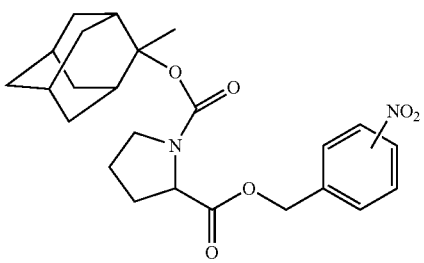
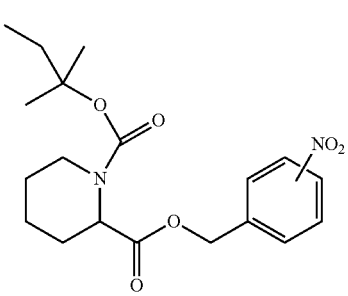

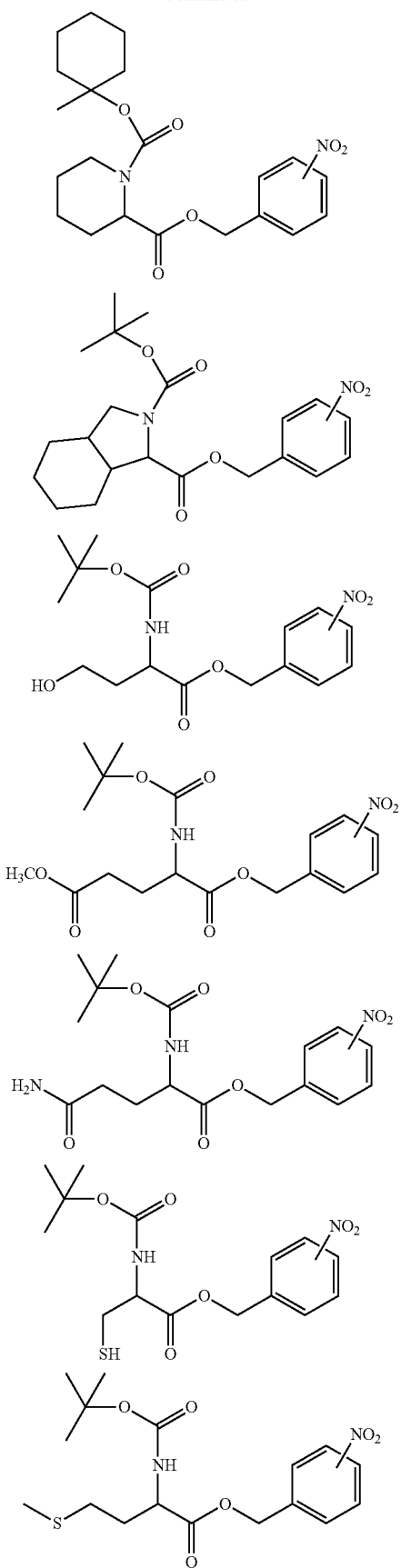
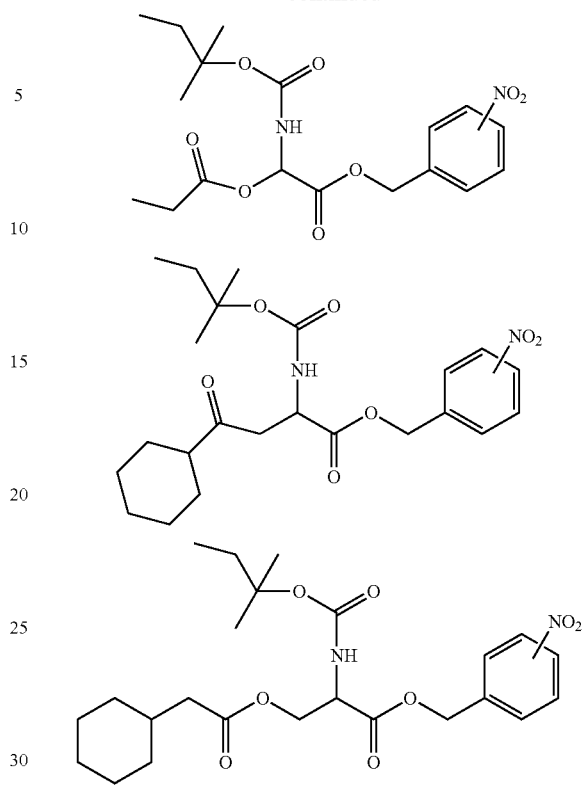
Examples of the compound wherein $R^{c1}$ is the group represented by the formula (1-3) and $R^{c2}$ is a nitrophenyl group include the followings.
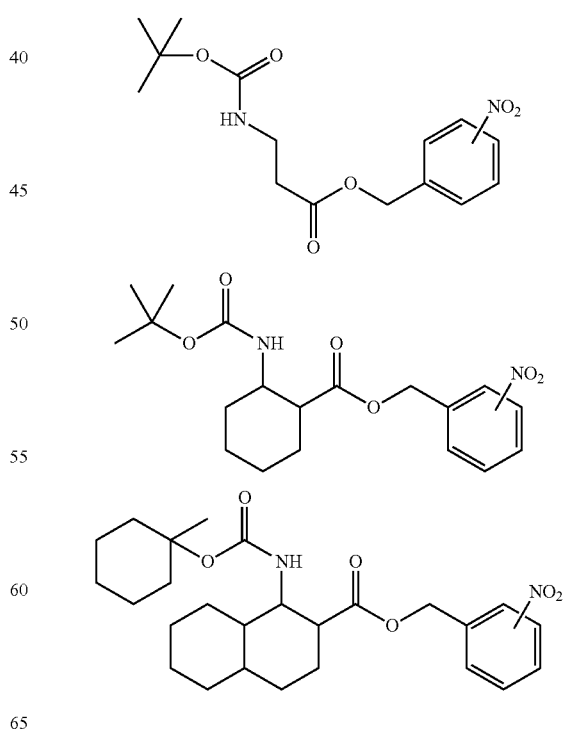

-continued

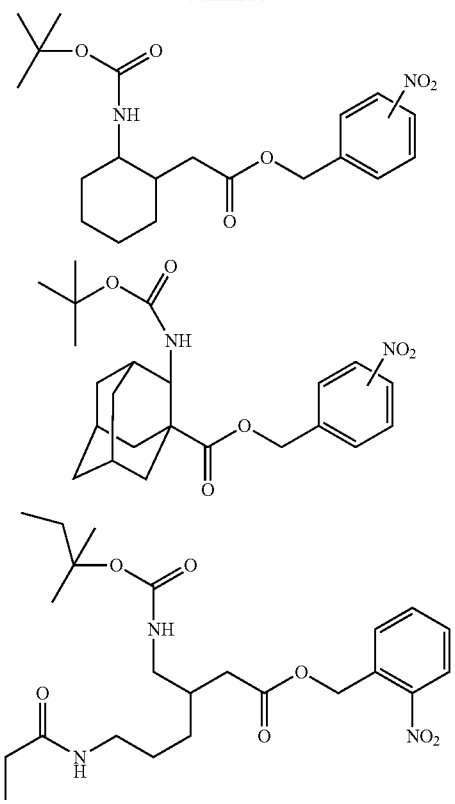

Among the above compounds, the following compounds represented by the formulae (C1-1-1), (C1-2-1), (C1-3-1), (C1-3-2) and (C1-4-1) are preferable.

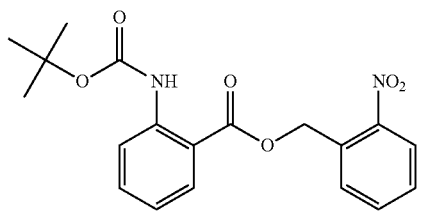
(C1-1-1)

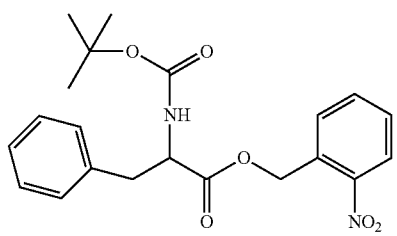
(C1-2-1)

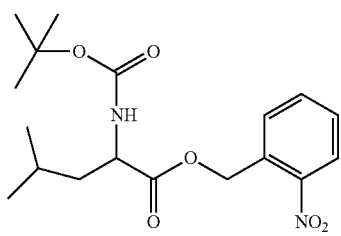
(C1-3-1)

-continued

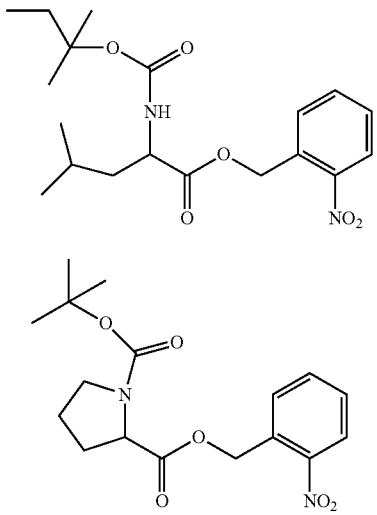
(C1-3-2)

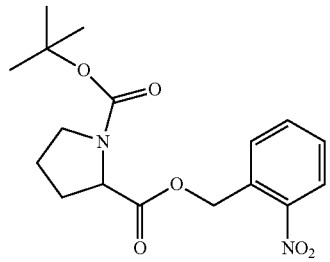
(C1-4-1)

The compound (C1) can be produced by a process comprising reacting a compound represented by the formula (C1-a):

(C1a)

wherein $R^{c1}$ is the same meaning as defined above (hereinafter, simply referred to as the compound (C1-a)), or a salt thereof with a compound represented by the formula (C1b):

(C1b)

wherein $R^{c2}$ is the same meaning as defined above and X represents a chlorine atom, a bromine atom or an iodine atom (hereinafter, simply referred to as the compound (C1b)). The reaction is preferably conducted in the presence of a basic alkali metal salt. Preferable basic alkali metal salt is at least one selected from the group consisting of a cesium salt, a potassium salt and a sodium salt. In the reaction, a salt of the compound (C1a) can be used in place of the compound (C1a). Preferable salt of the compound (C1a) is an alkali metal salt of the compound (C1a), and more preferable one is at least one selected from the group consisting of a cesium salt of the compound (C1a), a potassium salt of the compound (C1a) and a sodium salt of the compound (C1a).

When the compound (C1b) wherein X is a chlorine atom or a bromine atom, the reaction can be carried out in the presence of an alkali metal iodide.

The reaction is usually conducted in an organic solvent such as an aprotic polar solvent such as N,N-dimethylformamide and dimethylsulfoxide, with stirring at about 20 to about 150° C., preferably about 50 to about 100° C.

A commercially available compound (C1a) can be used.

Alternatively, compounds represented by the formula (C1a-1), (C1a-2) and (C1a-3) can be produced according to the following protection reactions.

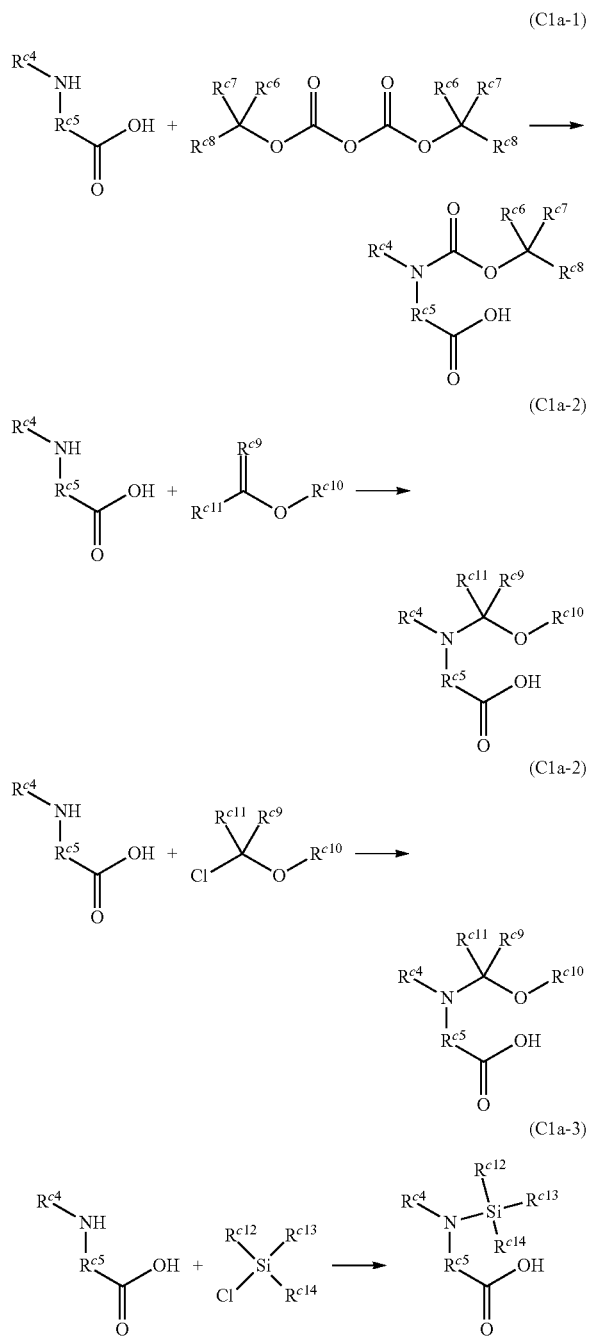

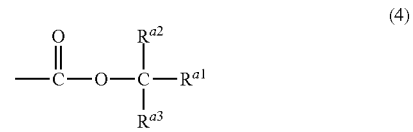

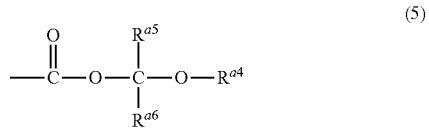

The above protection reaction is usually carried out in an organic solvent with stirring under gently heating (e.g. at about 0 to about 50° C.) or no heating. Examples of the organic solvent include tetrahydrofuran, 1,4-dioxane, ethyl acetate, N,N-dimethylformamide, chloroform and dichloroethane, and among them, an aprotic polar solvent such as tetrahydrofuran is preferable. The protection reaction can be conducted in the presence of a catalyst In the protection reaction producing the compound represented by the formula (C1a-1), sodium hydroxide can be used as the catalyst, and in the protection reaction producing the compound represented by the formula (C1a-3), methyl lithium (CH$_3$Li) can be used as the catalyst. When the compound represented by the formula (C1a-2) containing a dihydropyran structure is produced, sulfuric acid can be used as the catalyst. The above-mentioned protection reactions are known as a protection reaction of an amino group and known protecting agents other than the above-mentioned agent can be used and the reaction can be conducted under the conditions other than the above-mentioned condition.

Next, a photoresist composition comprises a resin, an acid-generator and the compound (C1) will be illustrated.

The photoresist composition of the present invention can contain two or more kinds of the compound (C1). The content of the compound (C1) is preferably 0.01 part by weight or more, more preferably 0.05 part by weight or more and much more preferably 001 part by weight or more per 100 parts by weight of the resin. The content of the compound (C1) is preferably 5 parts by weight or less, more preferably 3 parts by weight or less and much more preferably 2 parts by weight or less per 100 parts by weight of the resin.

The resin is preferably one being insoluble or poorly soluble in an aqueous alkali solution but becoming soluble in an aqueous alkali solution by the action of an acid. The resin preferably comprises a structural unit derived from a monomer having an acid-labile group in its side chain. The resin can have two or more kinds of structural unit derived from a monomer having an acid-labile group in its side chain.

In this specification, "an acid-labile group" means a group capable of being eliminated by the action of an acid. Examples of the acid-labile group include groups represented by the formulae (4) and (5):

wherein $R^{a1}$, $R^{a2}$ and $R^{a3}$ independently each represent a linear, branched chain or cyclic aliphatic hydrocarbon group, or $R^{a1}$ and $R^{a2}$ are bonded each other to form a ring together with a carbon atom to which $R^{a1}$ and $R^{a2}$ are bonded, $R^{a4}$ represents a linear, branched chain or cyclic aliphatic hydrocarbon group in which one or more —CH$_2$— can be replaced by —O— or —CO—, $R^{a5}$ and $R^{a6}$ independently each represent a hydrogen atom, or a linear or branched chain aliphatic hydrocarbon group, or $R^{a5}$ and $R^{a6}$ are bonded each other to form a ring together with a carbon atom to which $R^{a5}$ and $R^{a6}$ are bonded.

Examples of the group represented by the formula (4) include a 1,1-dialkylalkoxycarbonyl group such as a tert-butoxycarbonyl group, a 1-alkylcycloalkyloxycarbonyl group such as a 1-alkylcyclohexyloxycarbonyl group, a 2-alkyl-2-isobornyloxycarbonyl group, a 2-alkyl-2-adamantyl oxycarbonyl group and a 1-(1-adamantyl)-1-alkylalkoxycarbonyl group.

Examples of the group represented by the formula (5) include a methoxymethoxycarbonyl group, an ethoxymethoxycarbonyl group, a 1-ethoxyethoxycarbonyl group, a 1-isobutoxyethoxycarbonyl group, a 1-isopropoxyethoxycarbonyl group, a 1-ethoxypropoxyethoxycarbonyl group, a 1-(2-methoxyethoxy)ethoxycarbonyl group, a 1-(2-acetoxyethoxy)ethoxycarbonyl group, a 1-[2-(1-adamantyloxy)

ethoxy]ethoxycarbonyl group, a 1-[2-(1-adamantylcarbonyloxy)ethoxy]ethoxycarbonyl group, a tetrahydro-2-furyloxycarbonyl group and a tetrahydro-2-pyranyloxycarbonyl group.

Preferable monomer is a monomer having an acid-labile group in its side chain and a carbon-carbon double bond. Examples of the monomer having an acid-labile group in its side chain and a carbon-carbon double bond include an acrylate monomer having an acid-labile group, a methacrylate monomer having an acid-labile group in its side chain, a norbornenecarboxylate monomer having an acid-labile group in its side chain, a tricyclodecenecarboxylate monomer having an acid-labile group in its side chain and a tetracyclodecenecarboxylate monomer having an acid-labile group in its side chain.

An acrylate monomer having an acid-labile group in its side chain or a methacryalte monomer having an acid-labile group in its side chain is preferable.

Preferable examples of the monomer having an acid-labile group in its side chain include a monomer having an acid labile group containing a bulky structure such as a alicyclic hydrocarbon ring such as a cyclohexane ring and an adamantane ring. When the monomer having an acid labile group containing a bulky structure is used, a photoresist composition having excellent resolution tends to be obtained. Examples of the monomer having an acid labile group containing a bulky structure include the followings.

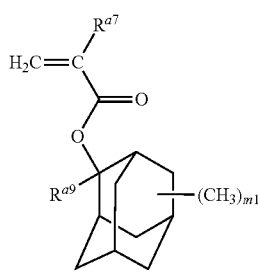

(a1-1)

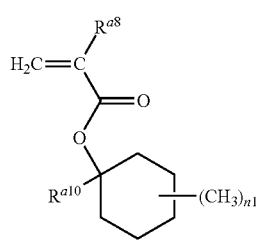

(a1-2)

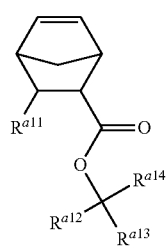

(a1-3)

wherein $R^{a7}$ and $R^{a8}$ independently each represent a hydrogen atom, a halogen atom such as a chlorine atom and a fluorine atom, or a methyl group, $R^{a9}$ and $R^{a10}$ are independently in each occurrence a linear, branched chain or cyclic C1-C10 aliphatic hydrocarbon group, and m1 represents an integer of 0 to 14, and n1 represents an integer of 0 to 10, $R^{a11}$ represents a hydrogen atom, a C1-C3 alkyl group, a C1-C3 hydroxyalkyl group, a carboxyl group, cyano group or a —$COOR^{a15}$ group in which $R^{a15}$ represents a linear, branched chain or cyclic C1-C8 aliphatic hydrocarbon group which can have one or more hydroxyl groups and in which one or more —$CH_2$— can be replaced by —O— or —CO—, $R^{a12}$, $R^{a13}$ and $R^{a14}$ independently each represent a linear, branched chain or cyclic C1-C12 hydrocarbon group which can have one or more hydroxyl groups and in which one or more —$CH_2$— can be replaced by —O— or —CO—, or $R^{a12}$ and $R^{a13}$ are bonded each other to form a ring together with the carbon atom to which $R^{a12}$ and $R^{a13}$ are bonded.

Examples of the linear, branched chain or cyclic C1-C10 aliphatic hydrocarbon group include a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group, an octyl group, a cycloheptyl group, a methylcycloheptyl group, a cyclohexyl group, a methylcyclohexyl group, a dimethylcyclohexyl group, a norbornyl group and a methylnorbornyl group. Among them, a C1-C8 aliphatic hydrocarbon group is preferable and a C1-C6 aliphatic hydrocarbon group is more preferable.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the C1-C3 alkyl group include a methyl group, an ethyl group and a propyl group, and examples of the C1-C3 hydroxyalkyl group include a hydroxylmethyl group and a 2-hydroxyethyl group.

Examples of $R^{a15}$ include a methyl group, an ethyl group, a propyl group, a 2-oxo-oxolan-3-yl group and a 2-oxo-oxolan-4-yl group.

Examples of the monomer represented by the formula (a1-1) include a 2-alkyl-2-adamantyl acrylate, a 2-alkyl-2-adamantyl methacrylate, and a 2-alkyl-2-adamantyl α-chloroacrylate. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-butyl-2-adamantyl acrylate, 2-methyl-2-adamantyl α-chloroacrylate and 2-ethyl-2-adamantyl α-chloroacrylate. Particularly when 2-ethyl-2-adamantyl acrylate, 2-ethyl-2-adamantyl methacrylate, 2-isopropyl-2-adamantyl acrylate or 2-isopropyl-2-adamantyl methacrylate is used, a photoresist composition having excellent resolution, sensitivity and heat resistance tends to be obtained, and therefore, 2-ethyl-2-adamantyl acrylate, 2-ethyl-2-adamantyl methacrylate, 2-isopropyl-2-adamantyl acrylate and 2-isopropyl-2-adamantyl methacrylate are preferable and 2-ethyl-2-adamantyl methacrylate and 2-isopropyl-2-adamantyl methacrylate are more preferable.

Examples of the monomer represented by the formula (a1-2) include a 1-alkyl-1-cyclohexylacrylate such as 1-ethyl-1-cyclohexyl acrylate and a 1-alkyl-1-cyclohexyl methacrylate such as 1-ethyl-1-cyclohexyl methacrylate, and 1-ethyl-1-cyclohexyl methacrylate is preferable.

Examples of the monomer represented by the formula (a1-3) include tert-butyl 5-norbornene-2-carboxylate, 1-methylethyl-1-cyclohexyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

Among the monomers represented by the formulae (a1-1), (a1-2) and (a1-3), the monomer represented by the formula (a1-1) is preferable because a photoresist composition having excellent resolution tends to be obtained when such monomer is used.

The monomer represented by the formula (a1-1) wherein $R^{a9}$ is the alkyl group such as a 2-alkyl-2-adamantyl acrylate can be usually produced by reacting a 2-alkyl-2-adamantanol or a metal salt thereof with an acrylic halide or a methacrylic halide. The monomer represented by the formula (a1-2) wherein $R^{a10}$ is the alkyl group such as a 1-alkyl-1-cyclohexyl acrylate can be usually produced by reacting a 1-alkyl-1-cyclohexanol or a metal salt thereof with an acrylic halide or a methacrylic halide.

The resin preferably contains a structural unit derived from a monomer having no acid-labile group in its side chain in addition to the structural unit derived from a monomer having an acid-labile group in its side chain. When the resin contains a structural unit derived from a monomer having no acid-labile group in its side chain in addition to the structural unit derived from a monomer having an acid-labile group in its side chain, the content of the structural unit derived from a monomer having an acid-labile group in its side chain is usually 10 to 80 mol % and preferably 20 to 60 mol % based on 100 mol % of all the structural units of the resin. When the resin contains a structural unit derived from a monomer having an adamantyl group, especially the monomer represented by the formula (a1-1), the content thereof is preferably 15 mol % or more based on 100 mol % of all the structural units derived from a monomer having an acid-labile group in its side chain. The bigger the content of the structural unit derived from a monomer having an adamantyl group is, the higher dry-etching resistance the photoresist composition shows.

The resin can contain other structural unit or units. Examples of the monomer giving other structural unit include an acrylate monomer having no acid-labile group, a methacrylate monomer having no acid-labile group, an acrylonitrile monomer, a methacrylonitrile monomer, a norbornene monomer, a hydroxystyrene monomer, an unsaturated aliphatic dicarboxylic anhydride such as maleic anhydride, and itaconic acid anhydride.

When a monomer having one or more hydroxyl groups such as hydroxystyrene (for example, p-hydroxystyrene and m-hydroxystyrene) is used, the photoresist composition having good resolution and adhesiveness of photoresist to a substrate tends to be obtained. The resin containing a structural unit derived from a hydroxystyrene can be produced by preparing a resin containing a structural unit derived from an acetoxystyrene using an acetoxystyrene followed by deacetylation. When the exposing is conducted using KrF excimer laser, the resin preferably has a structural unit derived from a styrene monomer such as p-hydroxystyrene and m-hydroxystyrene. When the exposing is conducted using ArF excimer laser, the resin preferably has a structural unit derived from a monomer represented by the formula (a2-1):

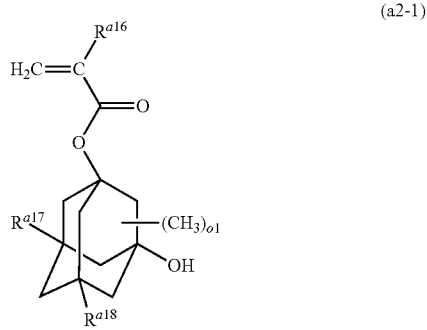

(a2-1)

wherein $R^{a16}$ represents a hydrogen atom or a methyl group, $R^{a17}$ and $R^{a18}$ each independently represent a hydrogen atom, a methyl group or a hydroxyl group, and o1 represents an integer of 0 to 10. The resin can contain two or more kinds of the structural unit derived from a monomer represented by the formula (a2-1) $R^{a16}$ is preferably a methyl group, and o1 is preferably an integer of 0 to 3, and more preferably 0 or 1.

Examples of the monomer represented by the formula (a2-1) include 3-hydroxy-1-adamantyl acrylate, 3-hydroxy-1-adamantyl methacrylate, 3,5-dihydroxy-1-adamantyl acrylate and 3,5-dihydroxy-1-adamantyl methacrylate, and 3-hydroxy-1-adamantyl acrylate and 3-hydroxy-1-adamantyl methacrylate are preferable and 3-hydroxy-1-adamantyl methacrylate is more preferable. 3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

The resin can contain one or more kinds of a structural unit derived from a monomer having a lactone ring. When a monomer having a lactone ring is used, the photoresist composition having good resolution and adhesiveness of photoresist to a substrate tends to be obtained.

Examples of the lactone ring include a monocyclic lactone ring such as β-propiolactone ring, γ-butyrolactone ring and γ-valerolactone ring, and a condensed ring formed from a monocyclic lactone ring and the other ring. Among them, γ-butyrolactone ring and a condensed lactone ring formed from γ-butyrolactone ring and the other ring are preferable.

Preferable examples of the monomer having a lactone ring include the monomers represented by the formulae (a3-1), (a3-2) and (a3-3):

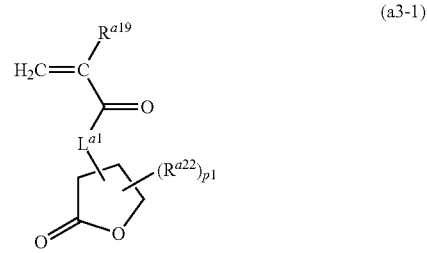

(a3-1)

-continued (a3-2) 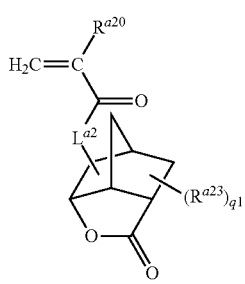

(a3-3) 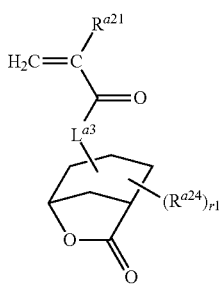

wherein $L^{a1}$, $L^{a2}$ and $L^{a3}$ each independently represent —O— or —O—$(CH_2)_{s1}$—CO—O—, s1 represents an integer of 1 to 4, $R^{a19}$, $R^{a20}$ and $R^{a21}$ each independently represent a hydrogen atom or a methyl group, $R^{a22}$, $R^{a23}$ and $R^{a24}$ are independently in each occurrence a methyl group, a trifluoromethyl group or a halogen atom, and p1, q1 and r1 independently each represents an integer of 0 to 3. $R^{a19}$, $R^{a20}$ and $R^{a21}$ are preferably methyl groups. $L^{a1}$ is preferably bonded to α-position or β-position of γ-butyrolactone ring and more preferably bonded to α-position of γ-butyrolactone ring. $L^{a2}$ is preferably bonded to 2-position or 3-position of 5-oxo-4-oxatricyclo[4.2.1.0$^{3,7}$]nonane ring and more preferably bonded to 2-position of 5-oxo-4-oxatricyclo[4.2.1.0$^{3,7}$]nonane ring. $L^{a3}$ is preferably bonded to 4-position of 7-oxo-6-oxabicyclo[3.2.1]octane ring.

Examples of the monomer represented by the formula (a3-1) include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, β-acryloyloxy-γ-butyrolactone, β-methacryloyloxy-γ-butyrolactone, β-acryloyloxy-α-methyl-γ-butyrolactone and β-methacryloyloxy-α-methyl-γ-butyrolactone. Among them, α-acryloyloxy-γ-butyrolactone and α-methacryloyloxy-γ-butyrolactone are preferable.

Examples of the monomer represented by the formula (a3-2) include the followings.

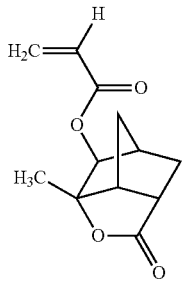
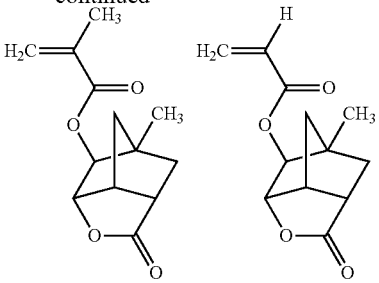

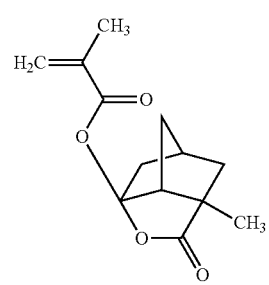

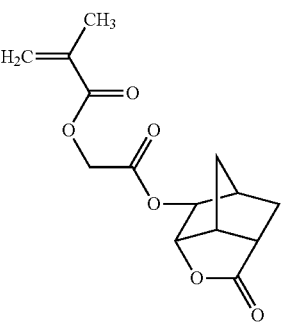
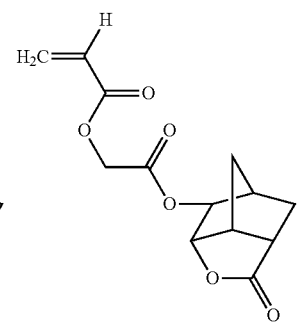

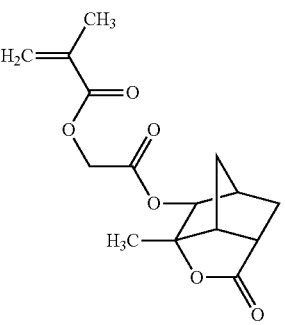
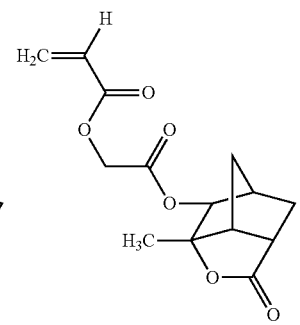

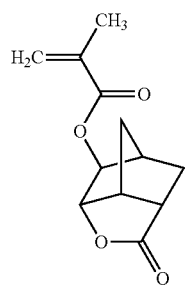
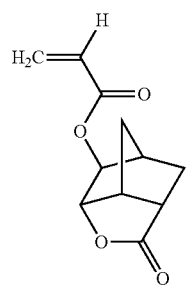
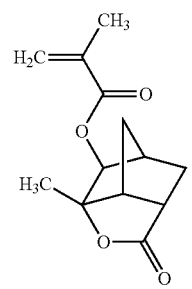

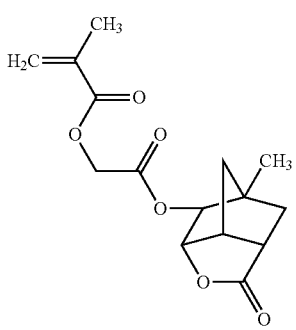

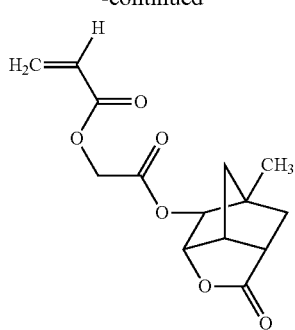

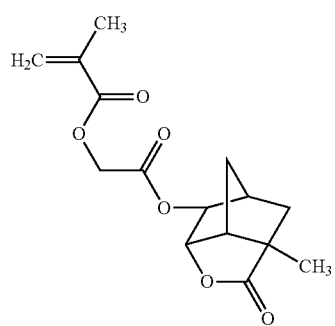

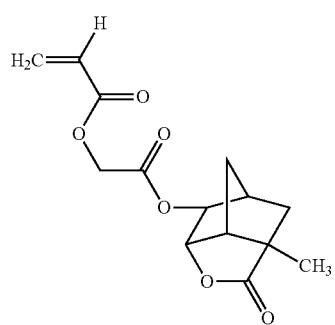

Among them, 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate are preferable.

Examples of the monomer represented by the formula (a3-3) include the followings.

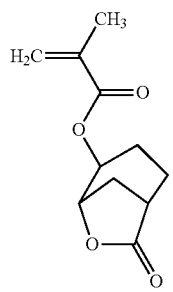 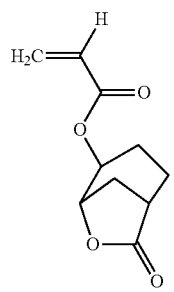 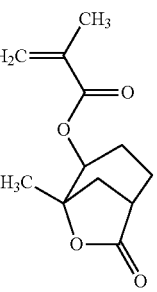

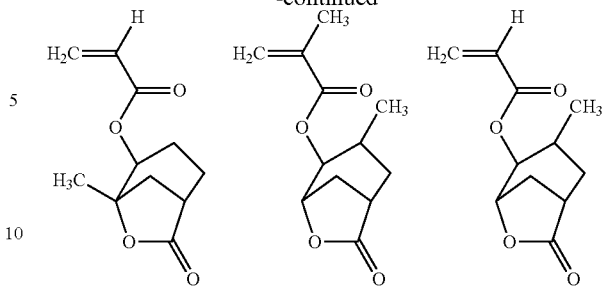

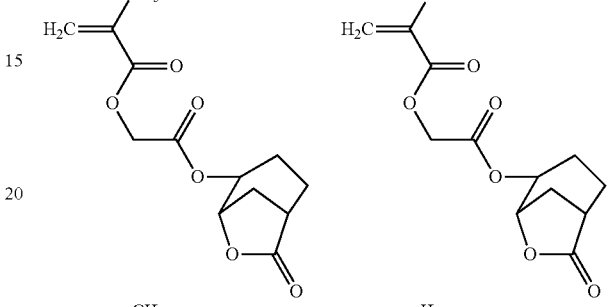

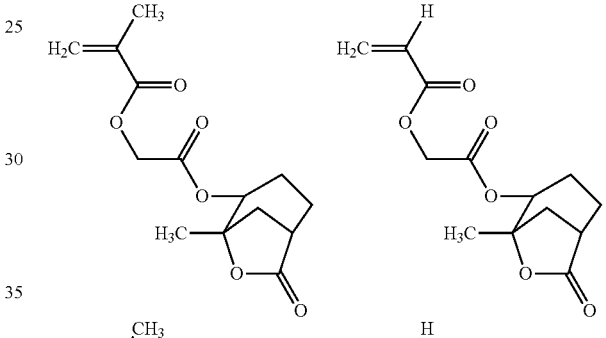

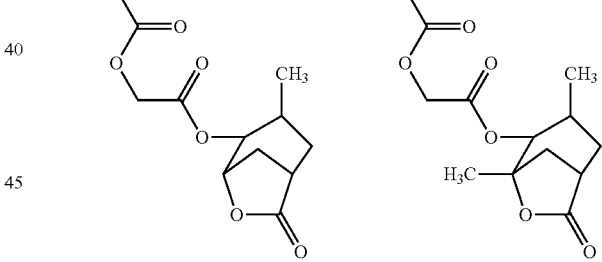

Among them, 7-oxo-6-oxabicyclo[3.2.1]octan-4-yl acrylate, 7-oxo-6-oxabicyclo[3.2.1]octan-4-yl methacrylate, 2-(7-oxo-6-oxabicyclo[3.2.1]octan-4-yloxy)-2-oxoethyl acrylate and 2-(7-oxo-6-oxabicyclo[3.2.1]octan-4-yloxy)-2-oxoethyl methacrylate are preferable.

The monomer represented by the formula (a3-1) wherein L$^{a1}$ is —O— can be produced by reacting the corresponding γ-butyrolactone having a halogen atom (preferably a bromine atom) with an alkali metal salt of acrylic acid or methacrylic acid or reacting the corresponding γ-butyrolactone having a hydroxyl group with acrylic halide, methacrylic halide, acrylic acid ester or methacrylic acid ester. The monomer represented by the formula (a3-2) wherein L$^{a2}$ is —O— and the monomer represented by the formula (a3-3) wherein L$^{a3}$ is —O— can be produced by reacting acrylic acid or methacrylic acid with the following hydroxyl-containing lactones, and the production method thereof is described in, for example, JP 2000-26446 A.

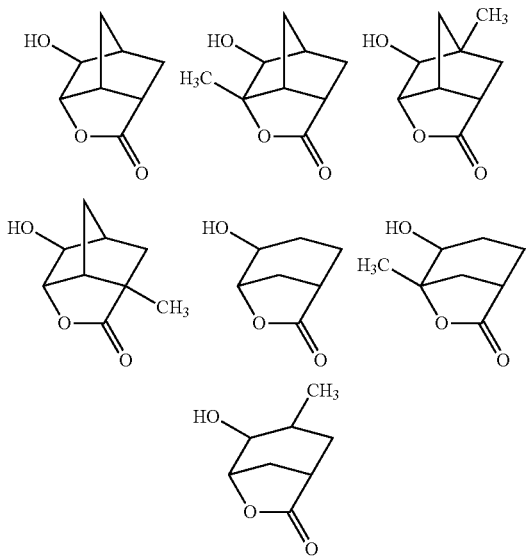

The monomer represented by the formula (a3-1) wherein $L^{a1}$ is —O—$(CH_2)_{s1}$—CO—O— can be produced by reacting the corresponding γ-butyrolactone having X—$(CH_2)_{s1}$—CO—O— group wherein X represents a halogen atom, with an alkali metal salt of acrylic acid or methacrylic acid or reacting the corresponding γ-butyrolactone having HO—$(CH_2)_{s1}$—CO—O— group with acrylic halide, methacrylic halide, acrylic acid ester or methacrylic acid ester. The monomer represented by the formula (a3-2) wherein $L^{a2}$ is —O—$(CH_2)_{s1}$—CO—O— and the monomer represented by the formula (a3-3) wherein $L^{a3}$ is —O—$(CH_2)_{s1}$—CO—O— can be produced by reacting acrylic acid or methacrylic acid with the following lactones, and the production method thereof is described in, for example, JP 2005-331918 A and JP 2005-352466 A.

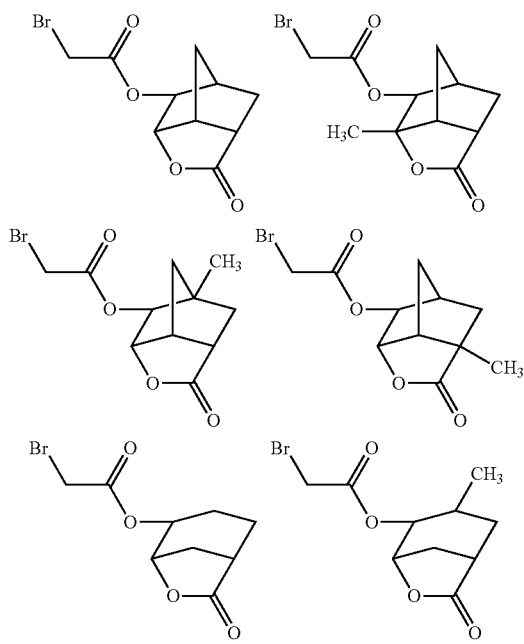

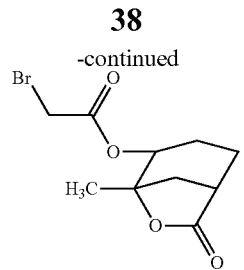

Examples of the other monomer include a monomer represented by the formula (a4-1)

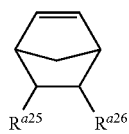

(a4-1)

wherein $R^{a25}$ and $R^{a26}$ each independently represents a hydrogen atom, a C1-C3 alkyl group, a C1-C3 hydroxyalkyl group, a carboxyl group, a cyano group or a —$COOR^{a27}$ group in which $R^{a27}$ represents a linear, branched chain or cyclic C1-C8 aliphatic hydrocarbon group which can have one or more hydroxyl groups and in which one or more —$CH_2$— can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)OC(=O)—. Examples of the C1-C3 alkyl group and the C1-C3 hydroxyalkyl group include the same as described above, and examples of the aliphatic hydrocarbon group include the same as described in $R^{a15}$.

Examples of the monomer represented by the formula (a4-1) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride. When the resin contains a structural unit derived from a monomer represented by the formula (a4-1), the photoresist composition showing higher dry-etching resistance tends to be obtained, Preferable resin is a resin containing the structural units derived from the monomer having an acid-labile group in its side chain, the monomer having one or more hydroxyl groups and the monomer having a lactone ring. The monomer having an acid-labile group in its side chain is preferably the monomer represented by the formula (a1-1), and the monomer having one or more hydroxyl groups is preferably the monomer represented by the formula (a2-1), and the monomer having a lactone ring is preferably the monomer represented by the formula (a3-1)

The resin usually has 1,000 or more of the weight-average molecular weight and 500,000 or less of the weight-average molecular weight, preferably has 4,000 or more of the weight-average molecular weight and 50,000 or less of the weight-average molecular weight. The weight-average molecular weight can be measured with gel permeation chromatography.

The resin can be obtained by conducting polymerization reaction of the monomer or monomers. The polymerization reaction is usually carried out in the presence of a radical initiator. This polymerization reaction can be conducted according to known methods. If a monomer represented by the formula (a1-3) is to be used, it is preferable to use the monomer in an amount that is excessive with respect to a predicted amount of structural units of the monomer in a resin, since the polymerizability of the monomer is low.

The photoresist composition of the present invention contains an acid generator, and preferably a photoacid generator. The content of the acid generator is usually 0.1 part by weight or more, and preferably 3 parts by weight or more per 100 parts by weight of the resin. The content of the acid generator is usually 20 parts by weight or less and preferably 15 parts by weight or less per 100 parts by weight of the resin.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, anionic acid generator and the combination thereof. An ionic acid generator is preferable. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and DNQ 4-sulfonate. Examples of the ionic acid generator include an acid generator having an inorganic anion such as $BF_4^-$, $PF_6^-$, $AsF_6^-$ and $SbF_6^-$, and an acid generator having an organic anion such as a sulfonic acid anion and a bissulfonylimido anion, and an acid generator having a sulfonic acid anion is preferable. Preferable examples of the acid generator include a salt represented by the formula (B1):

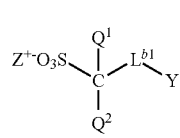

(B1)

wherein $Q^1$ and $Q^2$ each independently represent a fluorine atom or a C1-C6 perfluoroalkyl group, $L^{b1}$ represents a single bond or —(CH$_2$)$_{k2}$— which can be substituted with a linear or branched chain C1-C4 alkyl group and in which one or more methylene groups can be replaced by —O— or —CO—, k2 represents an integer of 1 to 17, Y represents a C3-C36 alicyclic hydrocarbon group which can have one or more substituents, and one or more methylene groups in the alicyclic hydrocarbon group can be replaced by —O— or —CO—, and $Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C3-C36 alicyclic hydrocarbon group include the groups represented by the formulae (W1) to (W24):

(W1)

(W2)

(W3)

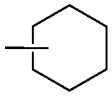

(W4)

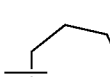

(W5)

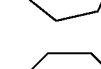

(W6)

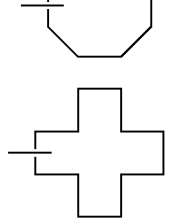

(W7)

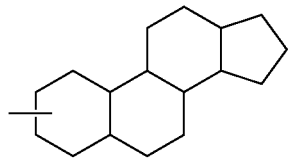

(W8)

(W9)

(W10)

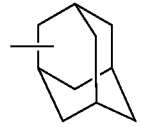

(W11)

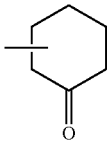

(W12)

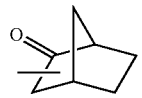

(W13)

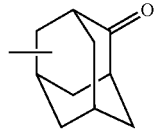

(W14)

(W15) 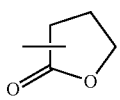

(W16) 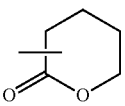

(W17) 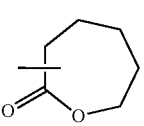

(W18) 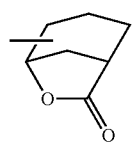

(W19) 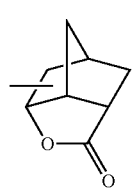

(W20) 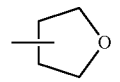

(W21) 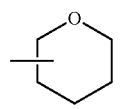

(W22) 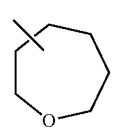

(W23) 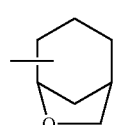

(W24) 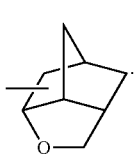

Among them, the groups represented by the formulae (W11), (W14), (W15) and (W19) are preferable and the groups represented by the formulae (W11) and (W14) are more preferable.

Examples of the substituent in Y include a halogen atom, a hydroxyl group, a linear, branched chain or cyclic C1-C12 aliphatic hydrocarbon group, a C1-C12 hydroxyl-containing aliphatic hydrocarbon group, a C1-C12 alkoxy group, a C6-C18 aromatic hydrocarbon group, a C7-C21 aralkyl group, a C2-C4 acyl group, a glycidyloxy group and —(CH$_2$)$_{j2}$—O—CO—R$^{b1}$ in which R$^{b1}$ represents a linear, branched chain or cyclic C1-C16 aliphatic hydrocarbon group or a C6-C18 aromatic hydrocarbon group, and j2 represents an integer of 0 to 4. Examples of the halogen atom include a fluorine atom, a chlorine atom, a bromine atom and an iodine atom, and examples of the aliphatic hydrocarbon group include the same as described above. Examples of the hydroxyl-containing aliphatic hydrocarbon group include a hydroxymethyl group, and examples of the alkoxy group include a methoxy group, an ethoxy group, a propoxy group, an isopropoxy group and a butoxy group, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group. Examples of the acyl group include an acetyl group and a propionyl group.

Examples of Y having one or more substituents include the followings:

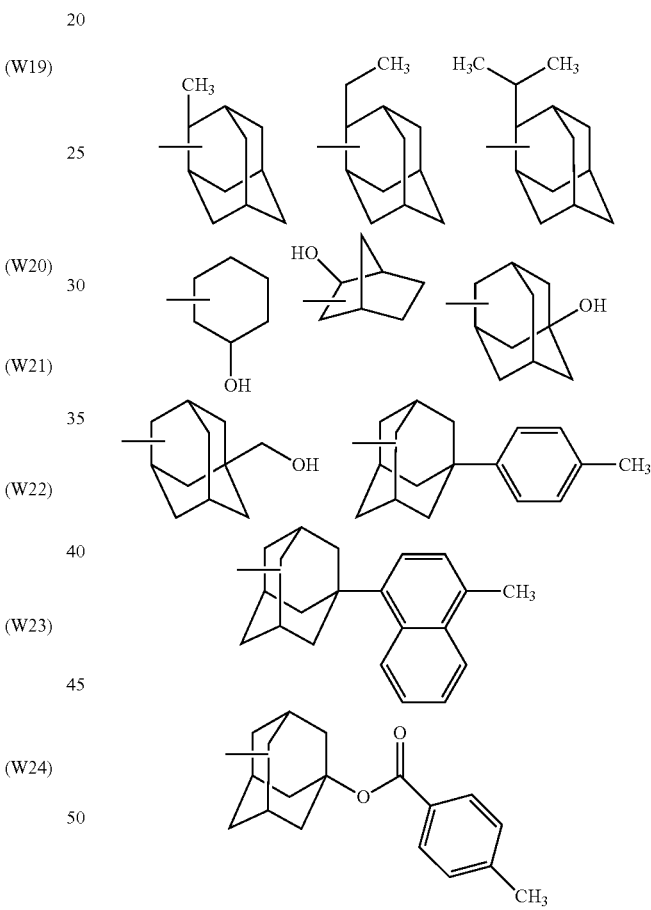

Examples of —(CH$_2$)$_{k2}$— include a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group. They can be substituted with a linear or branched chain C1-C4 alkyl group such as a methyl group, an ethyl group, a propyl group, an isopropyl group, a butyl group, a sec-butyl group and a tert-butyl group. One or more methylene groups in —(CH$_2$)$_{k2}$— can be replaced by —O— or —CO—.

Preferable examples of L$^{b1}$-Y include the following groups represented by the formulae (b1-1) to (b1-4):

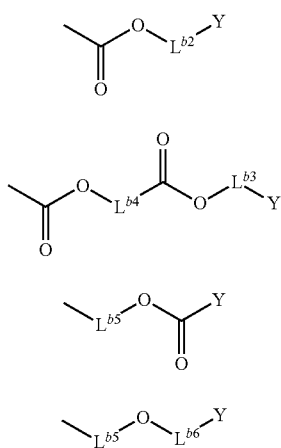

wherein L$^{b2}$ represents a single bond or —(CH$_2$)$_{i2}$—, i2 represents an integer of 1 to 15, L$^{b3}$ represents a single bond or —(CH$_2$)$_{h2}$—, L$^{b4}$ represents —(CH$_2$)$_{g2}$—, h2 represents an integer of 1 to 12, g2 represents an integer of 1 to 13, with the proviso that sum of h2 and g2 is an integer of 13 or less, L$^{b5}$ represents —(CH$_2$)$_{f2}$—, f2 represents an integer of 1 to 15, L$^{b6}$ represents —(CH$_2$)$_{e2}$—, L$^{b7}$ represents —(CH$_2$)$_{d2}$—, e2 represents an integer of 1 to 15, d2 represents an integer of 1 to 15, with the proviso that sum of d2 and e2 is an integer of 16 or less, and one or more methylene groups can be substituted with a linear or branched chain C1-C4 alkyl group. In the above formulae, i2 to d2 are preferably independently an integer of 1 to 6, more preferably independently an integer of 1 to 4, and especially preferably independently 1 or 2.

Among them, the group represented by the formula (b1-1) is preferable, and the group represented by the formula (b1-1) wherein L$^{b2}$ represents a single bond or —CH$_2$—, is more preferable.

Among the sulfonic acid anions having the group represented by the formula (b1-1), the anions represented by formulae (b1-1-1) to (b1-1-9) are preferable.

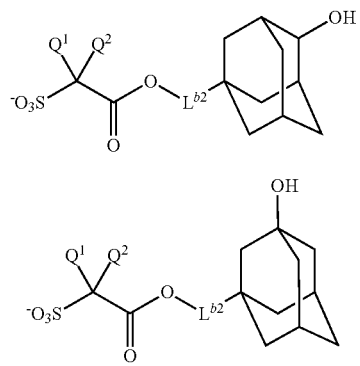

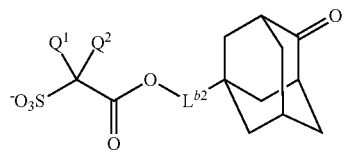

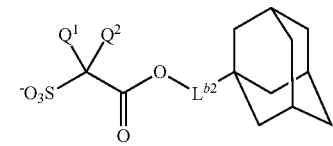

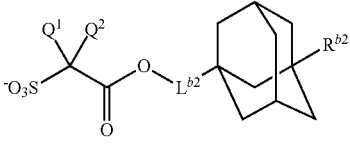

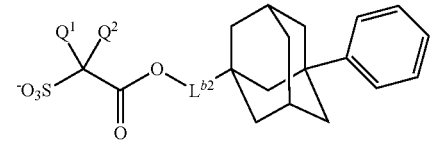

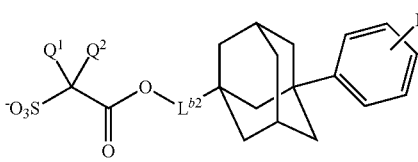

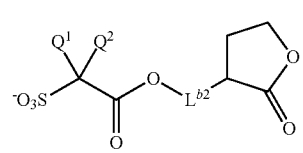

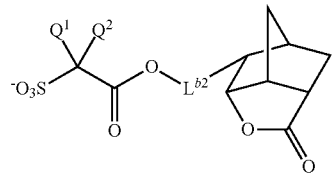

wherein Q$^1$, Q$^2$ and L$^{b2}$ are the same as defined above, and R$^{b2}$ and R$^{b3}$ each independently represent a C1-C4 aliphatic hydrocarbon group, preferably a methyl group.

Specific examples of the sulfonic acid anion include the followings.

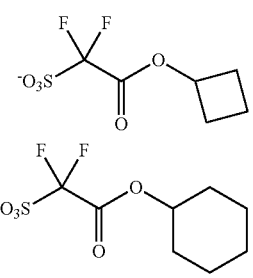

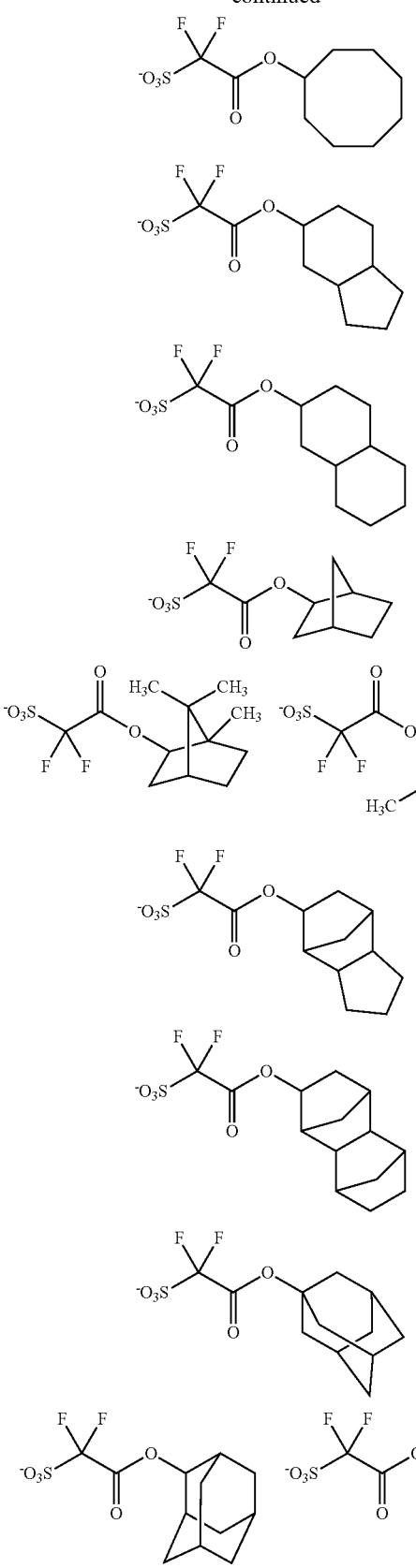
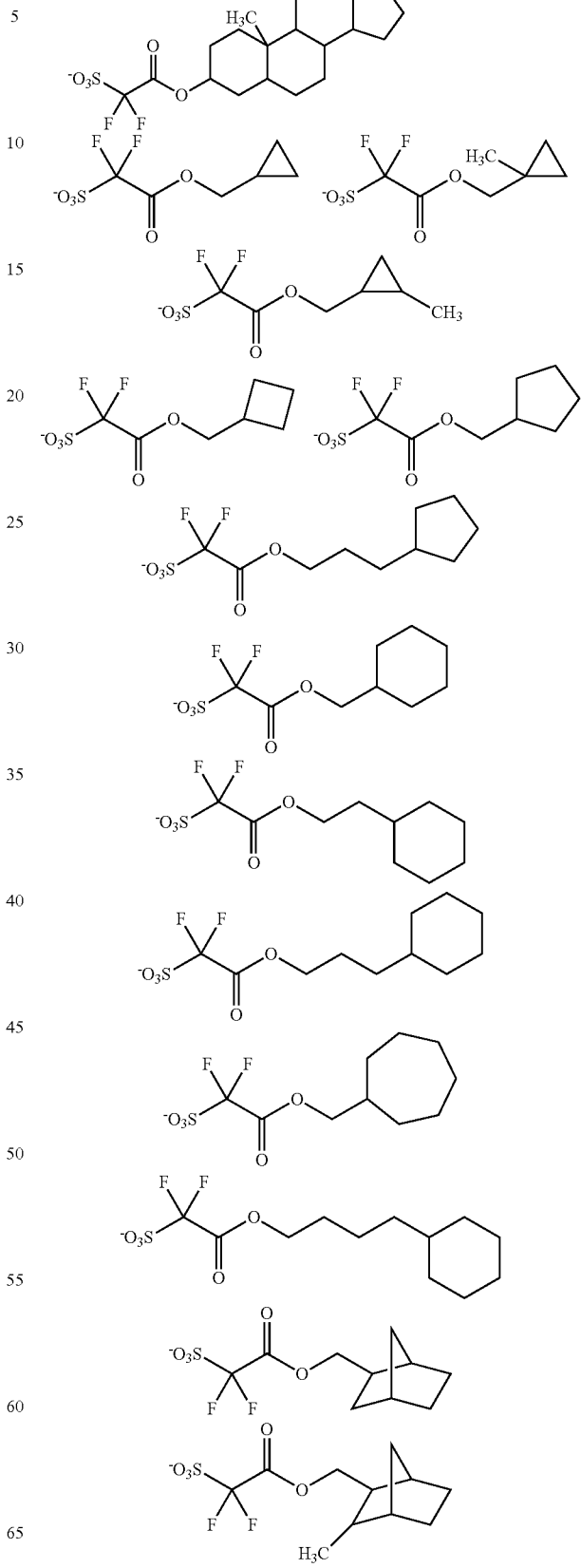

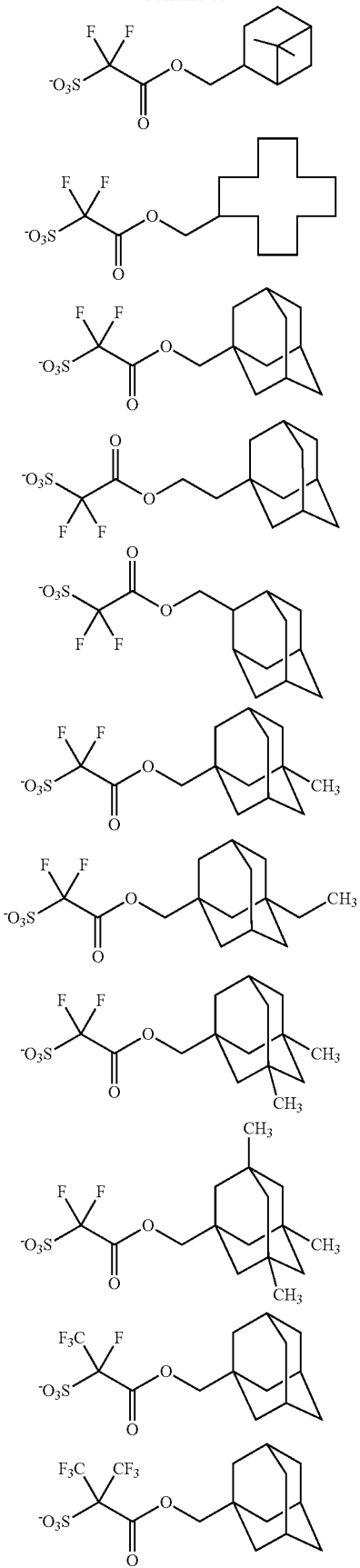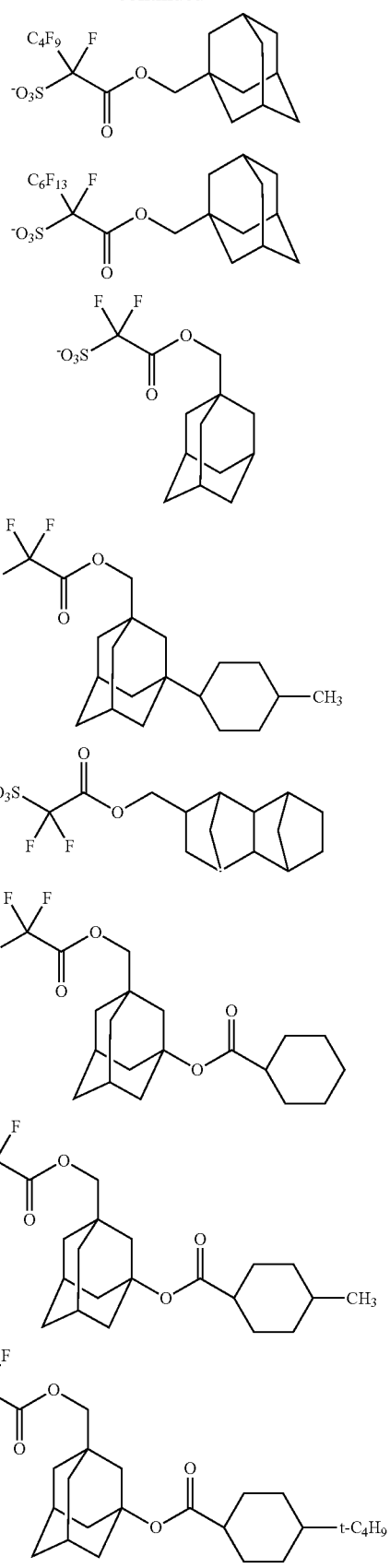

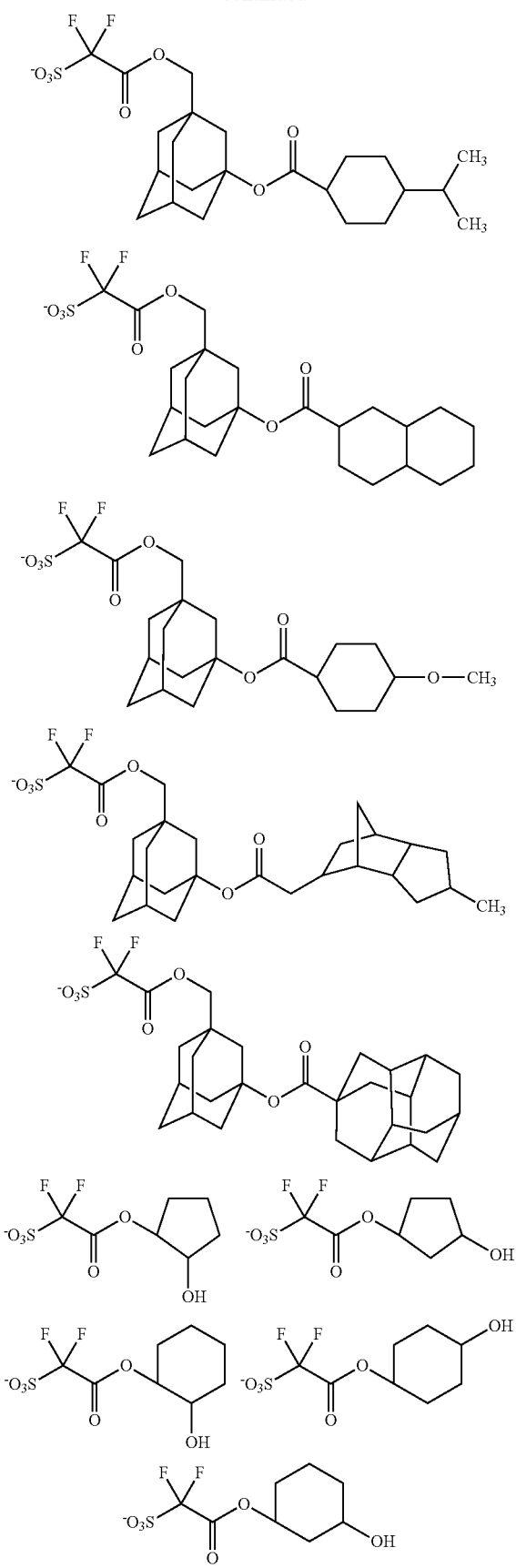
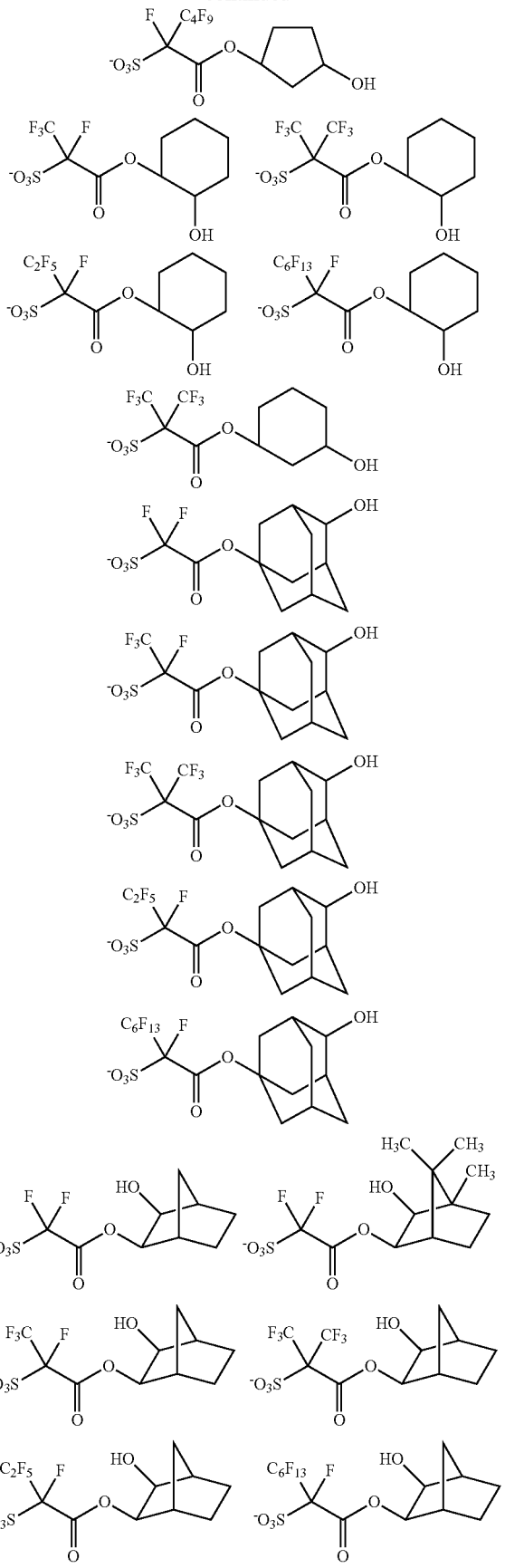

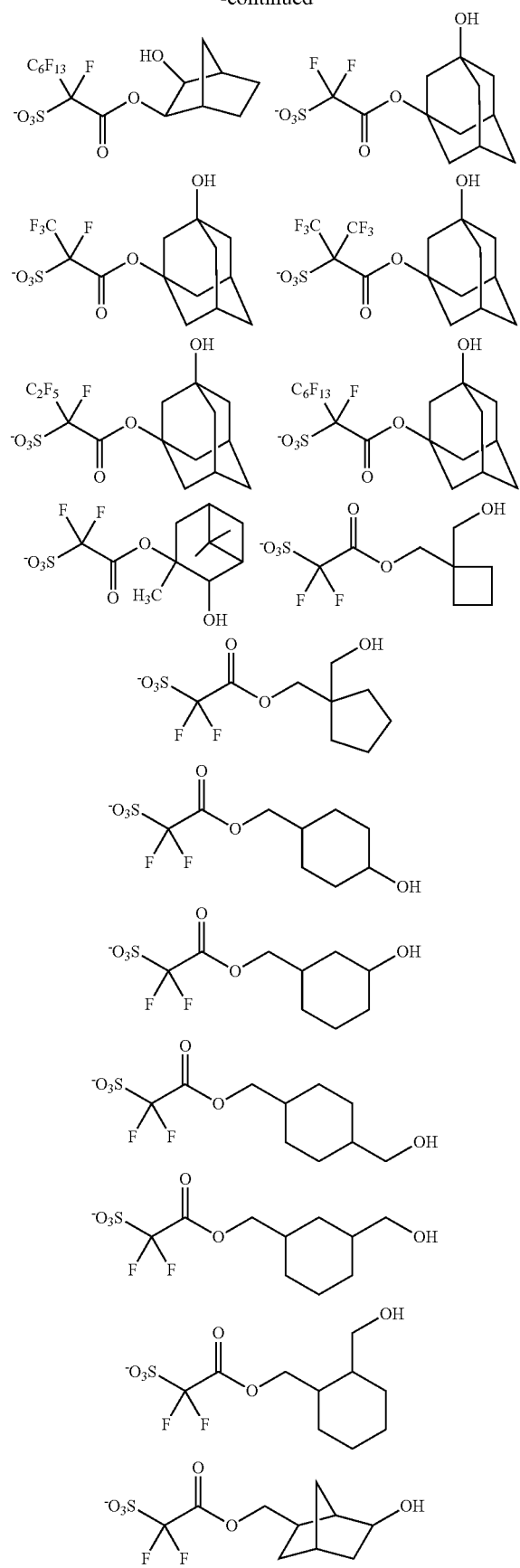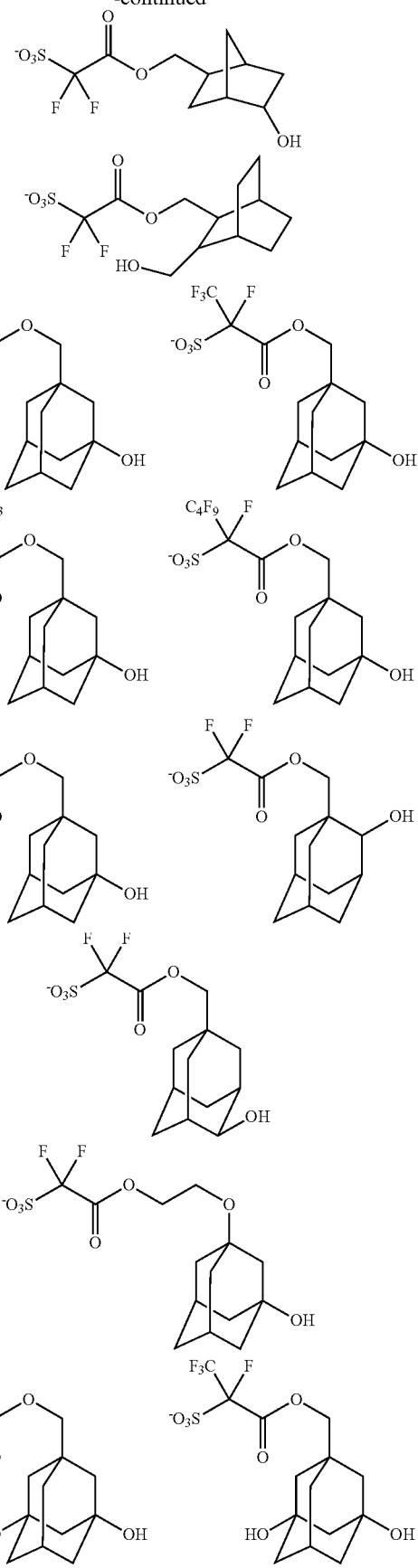

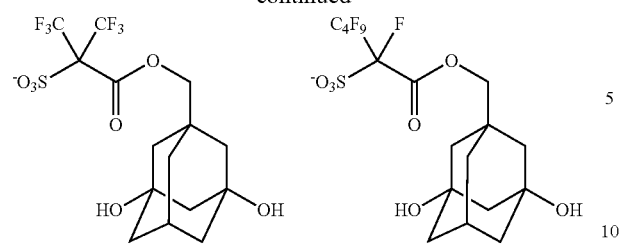
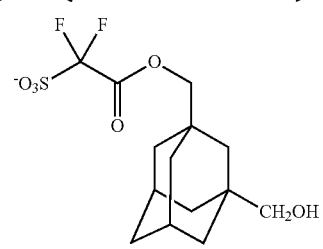
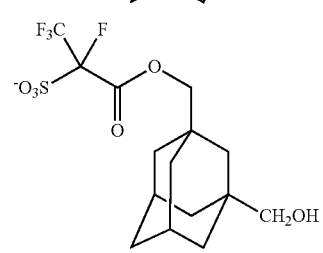
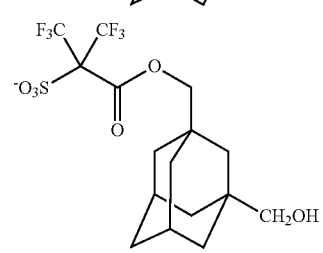
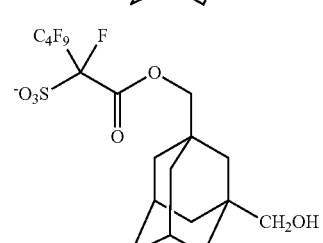
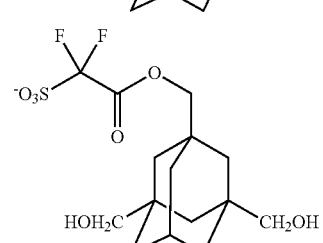
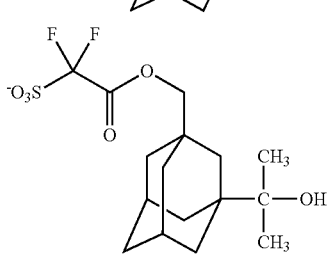
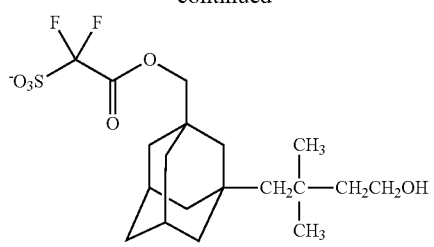
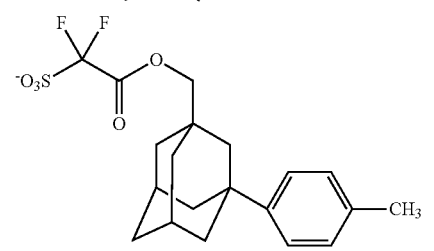
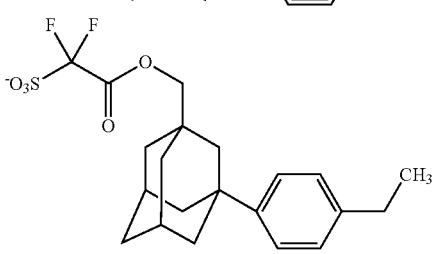
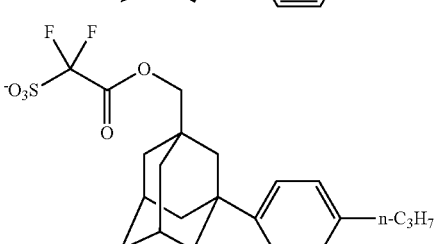
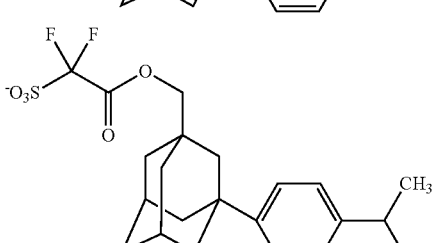
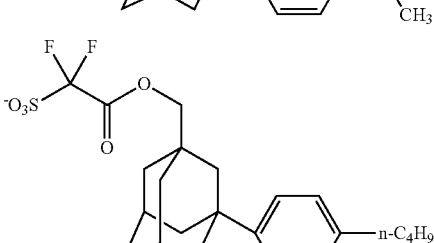
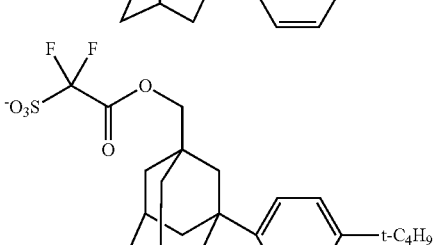

55
-continued
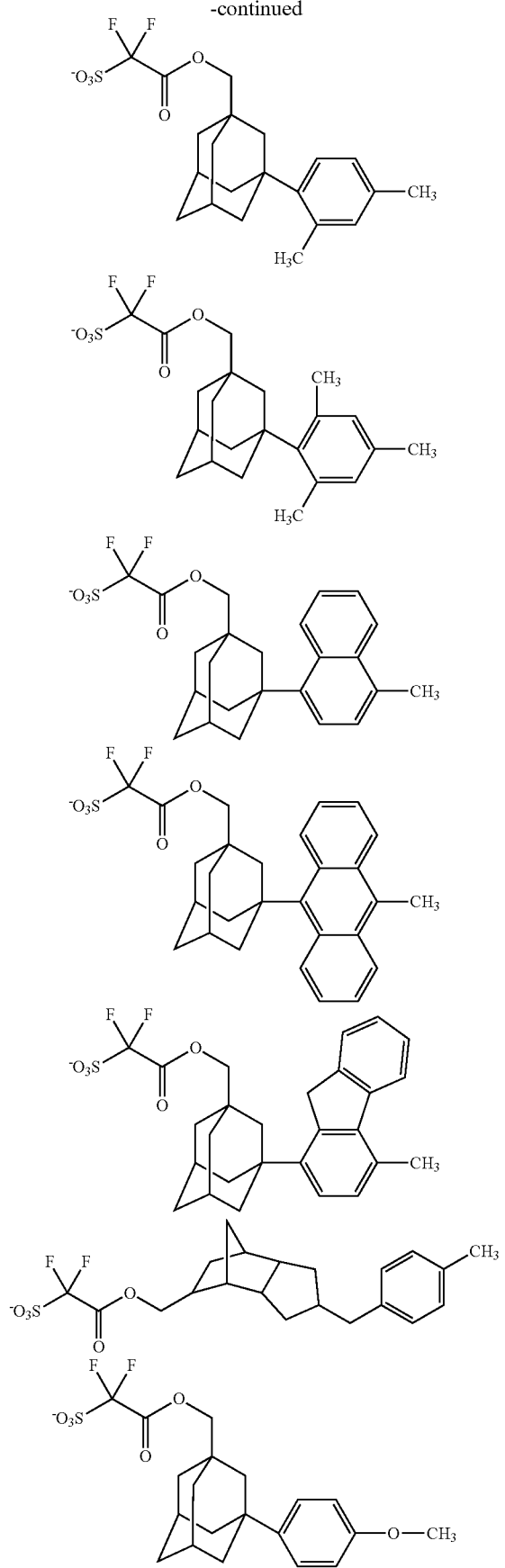
56
-continued
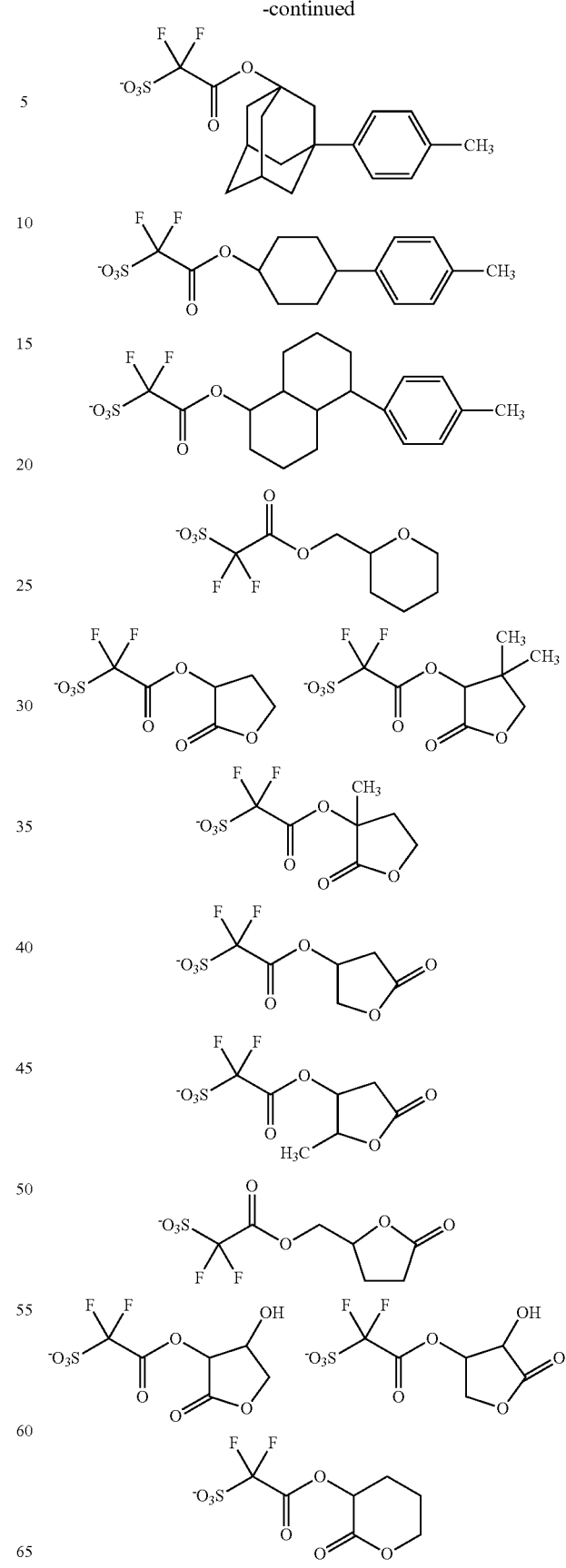

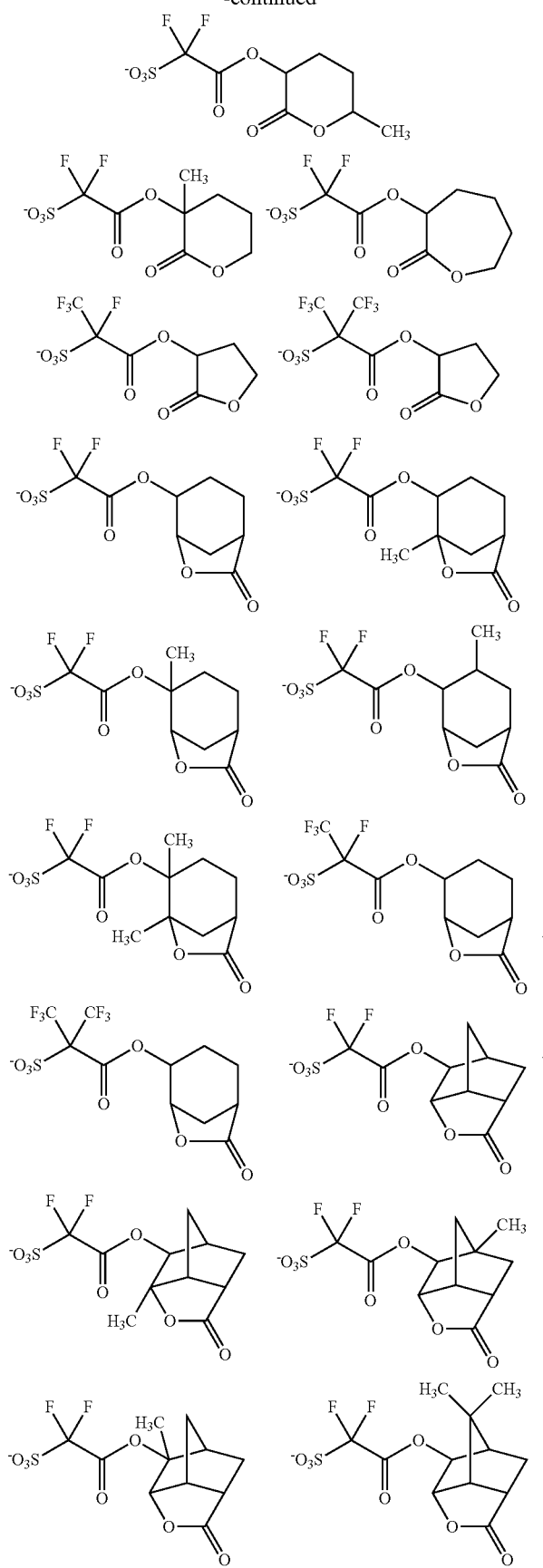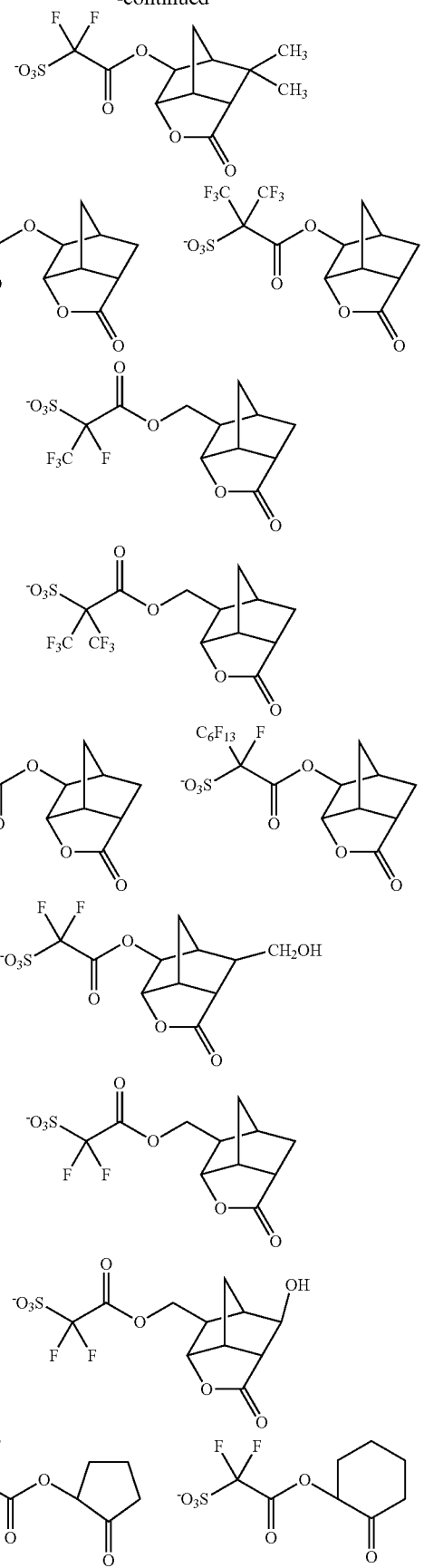

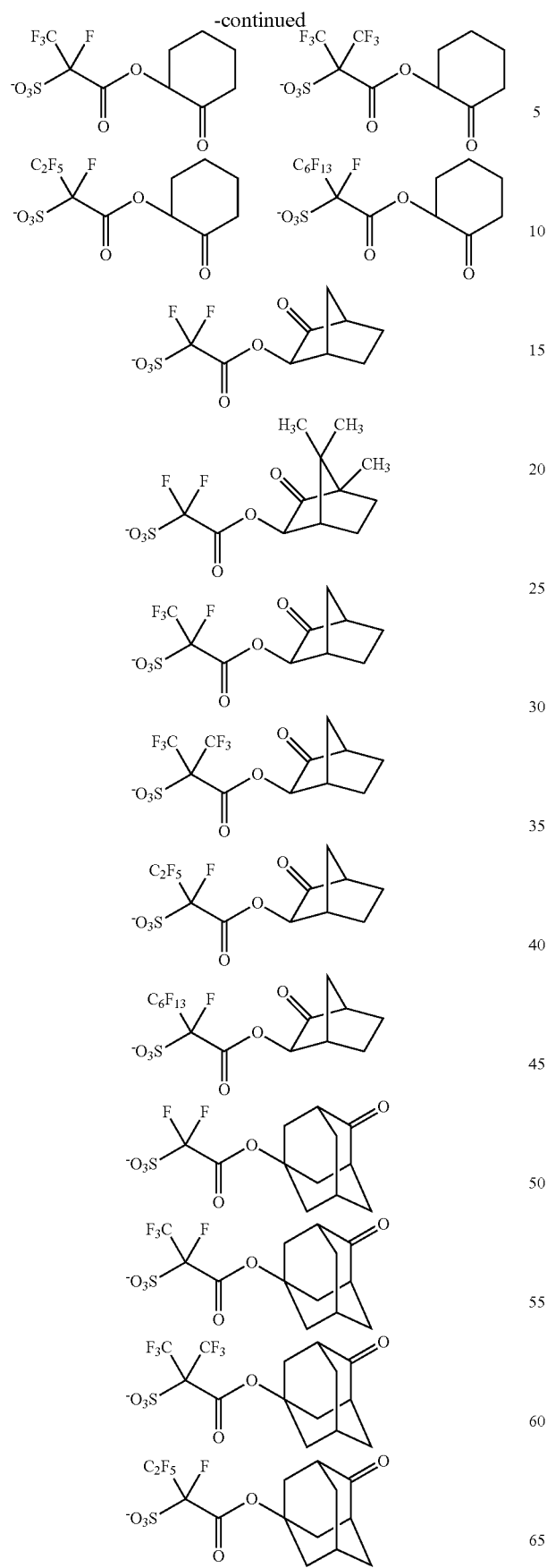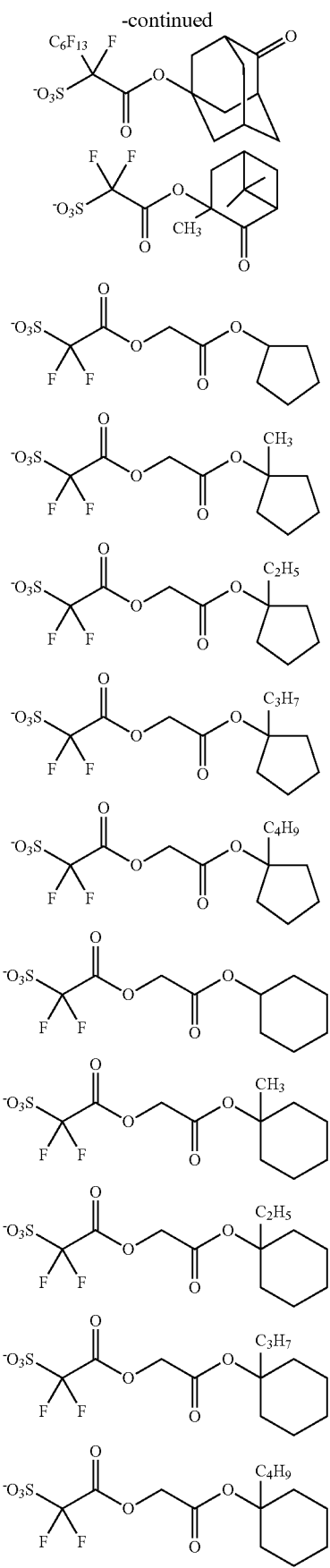

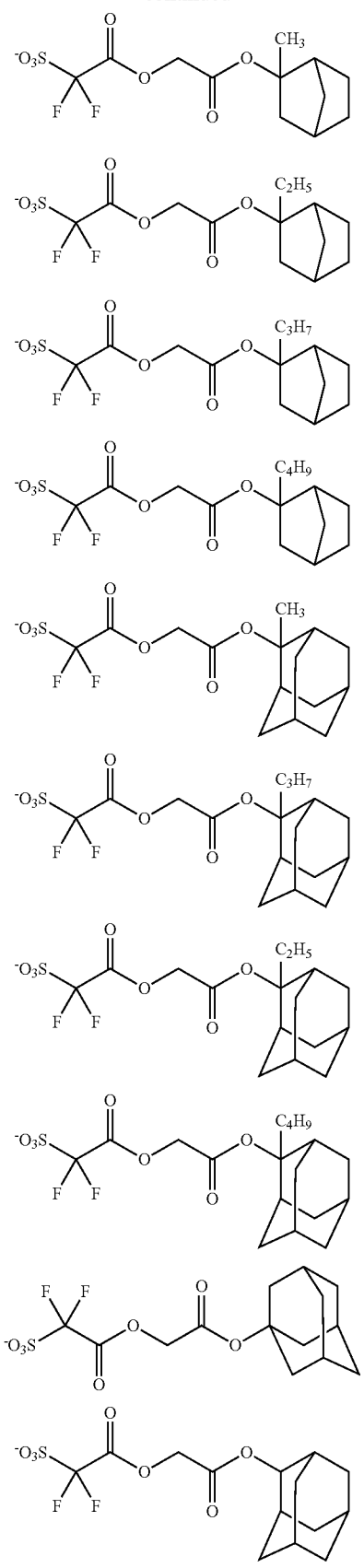
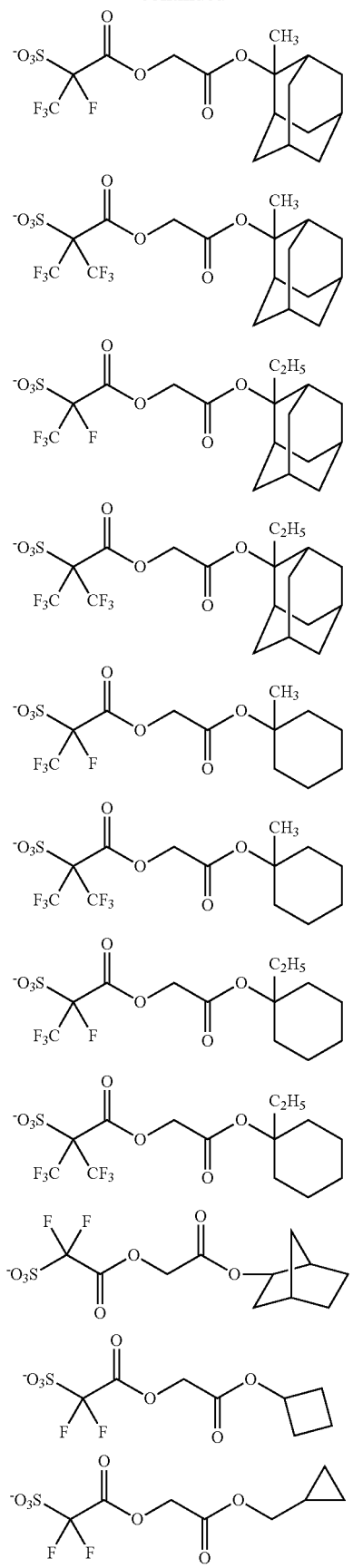

63
-continued
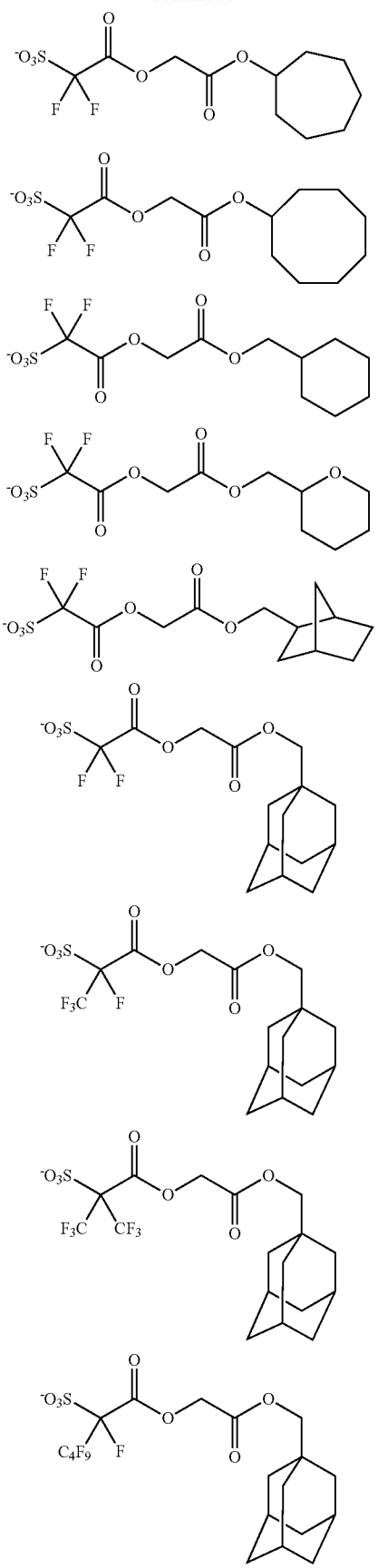
64
-continued
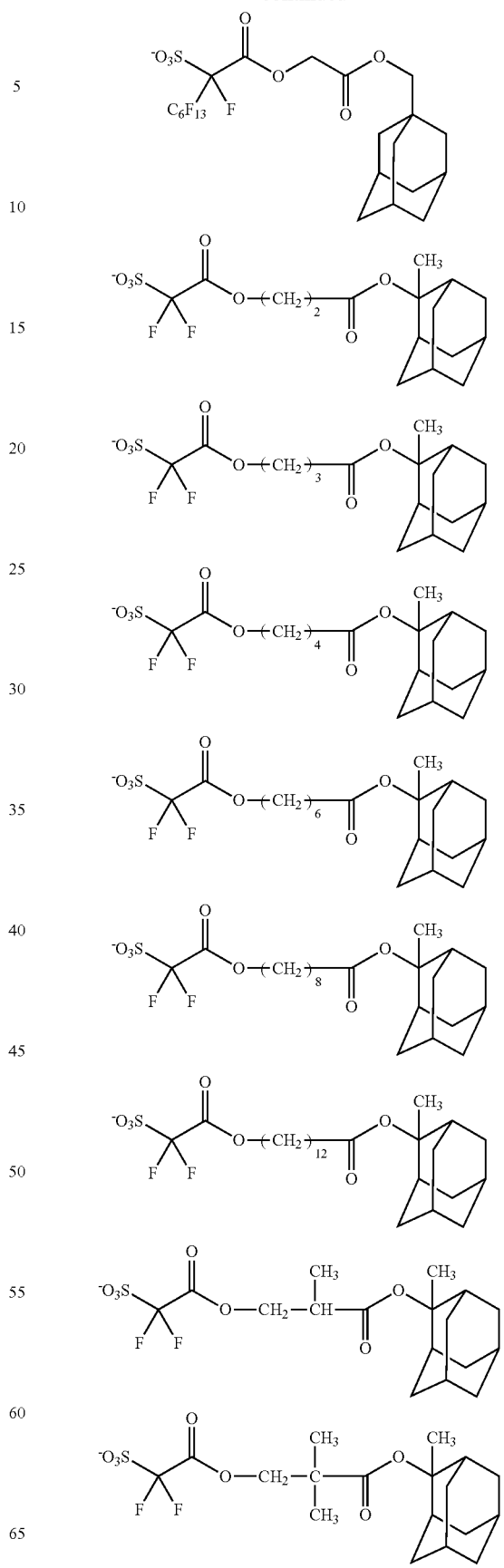

65
-continued
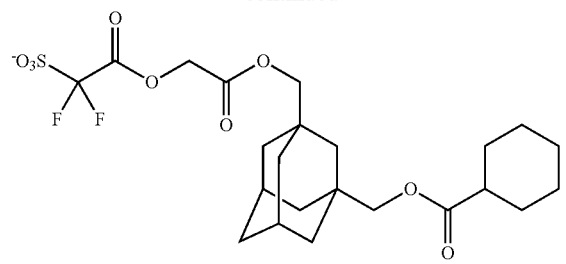
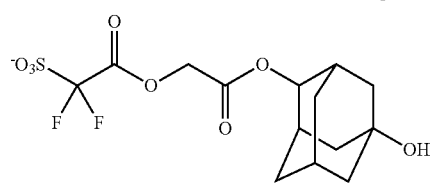
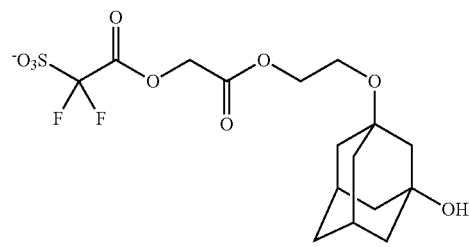
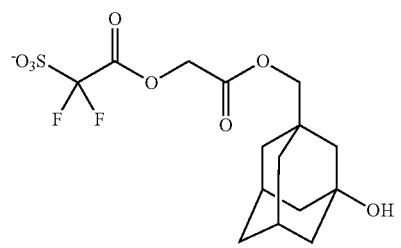
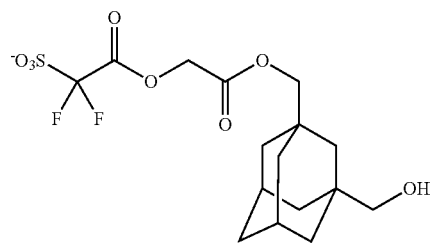
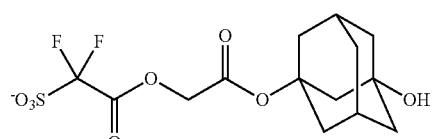
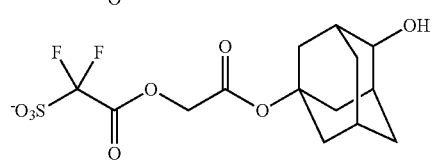
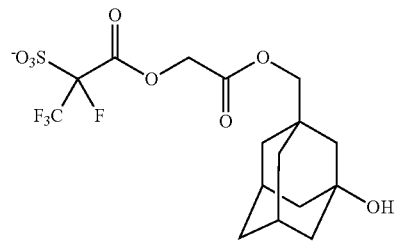
66
-continued
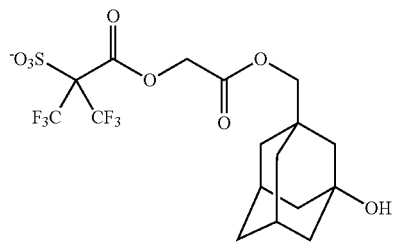
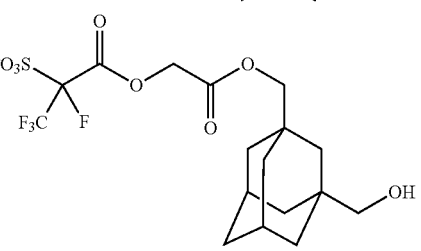
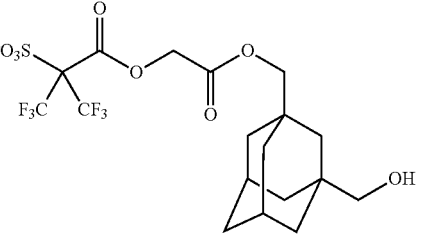
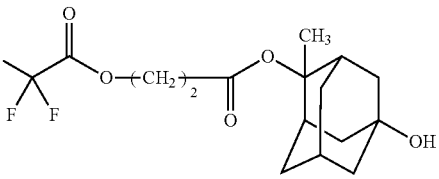
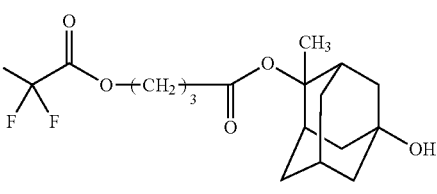
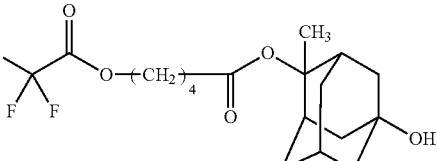
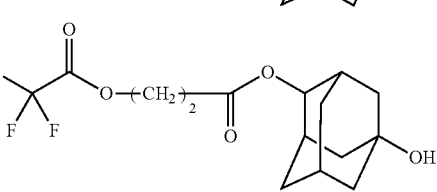
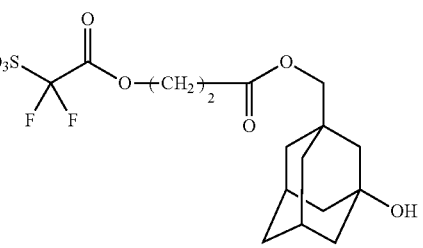

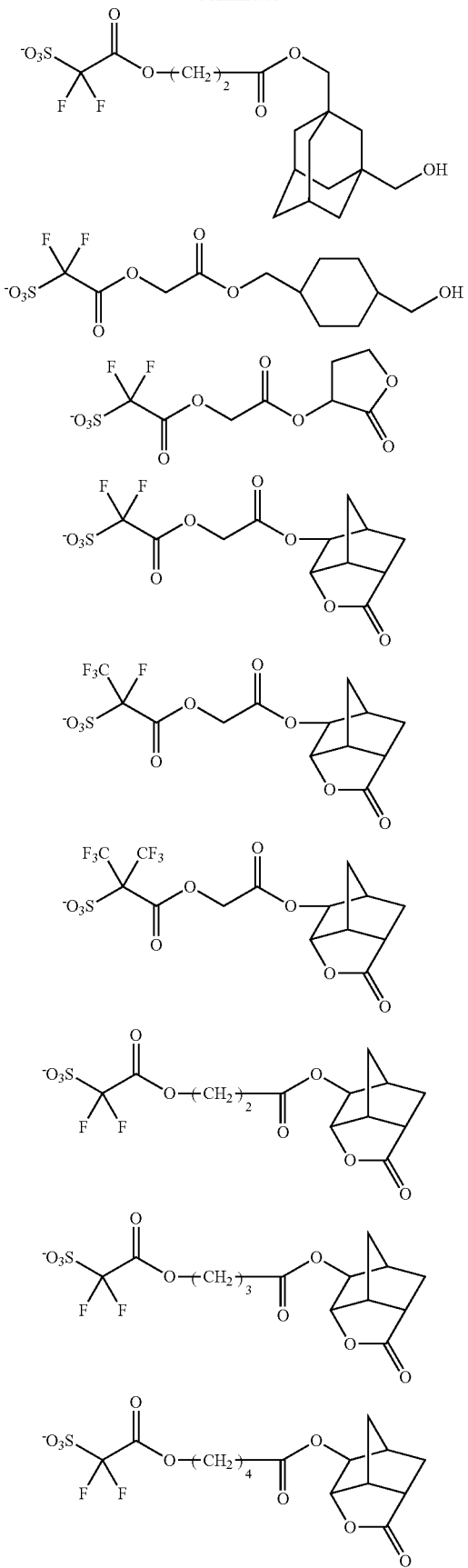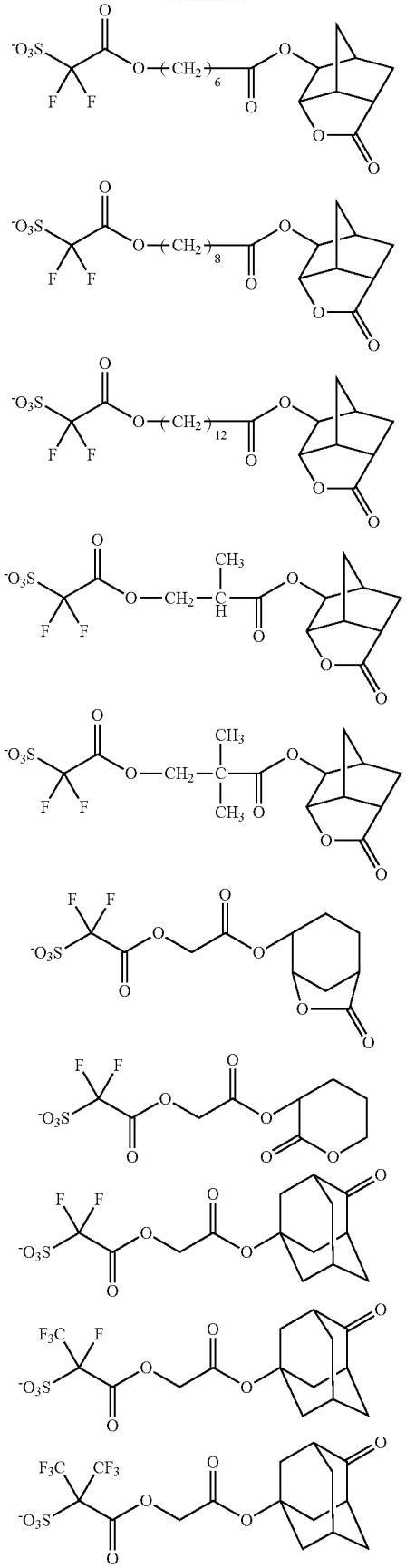

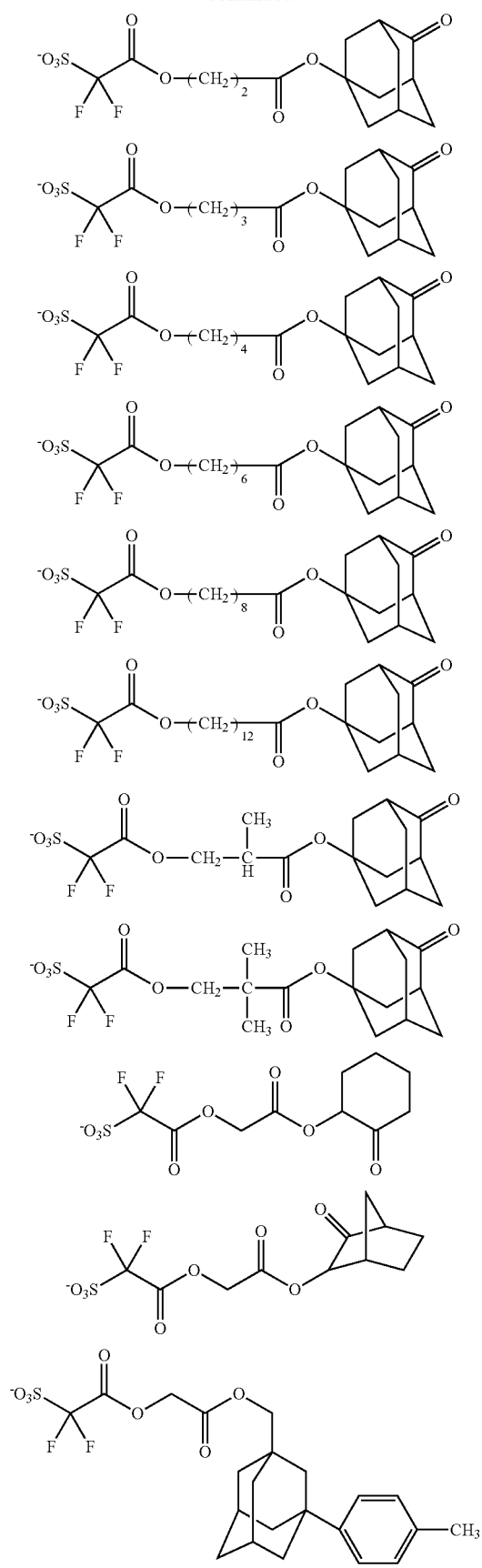
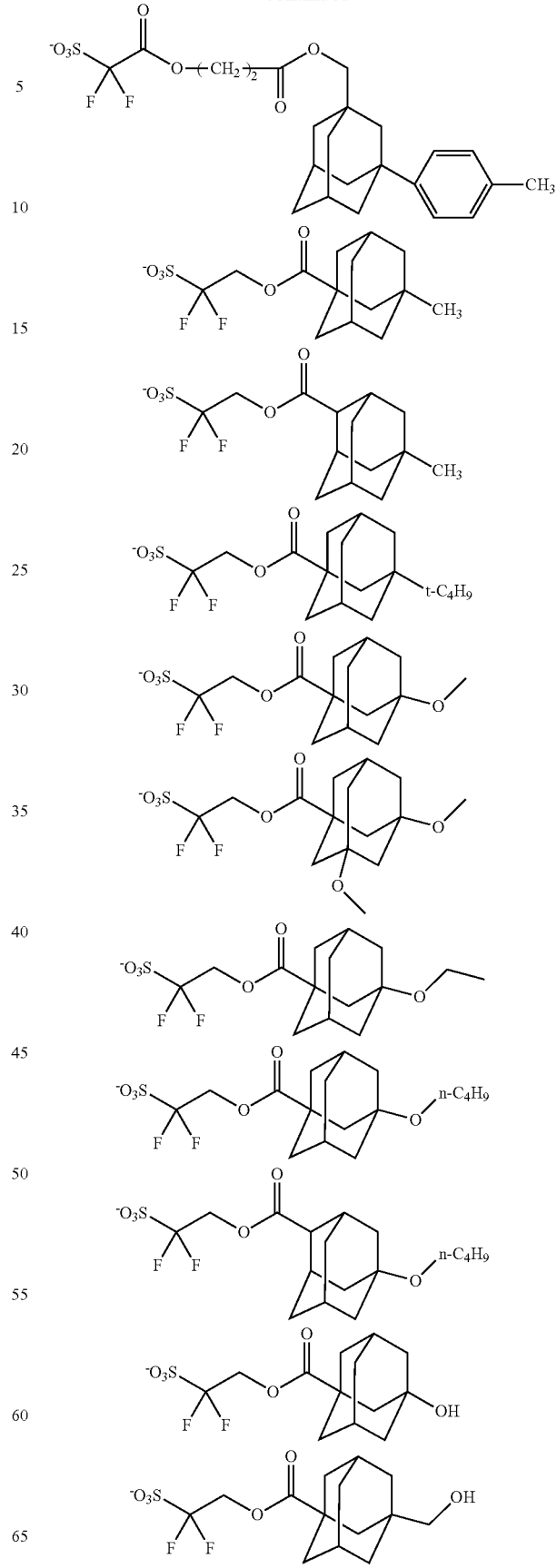

71
-continued
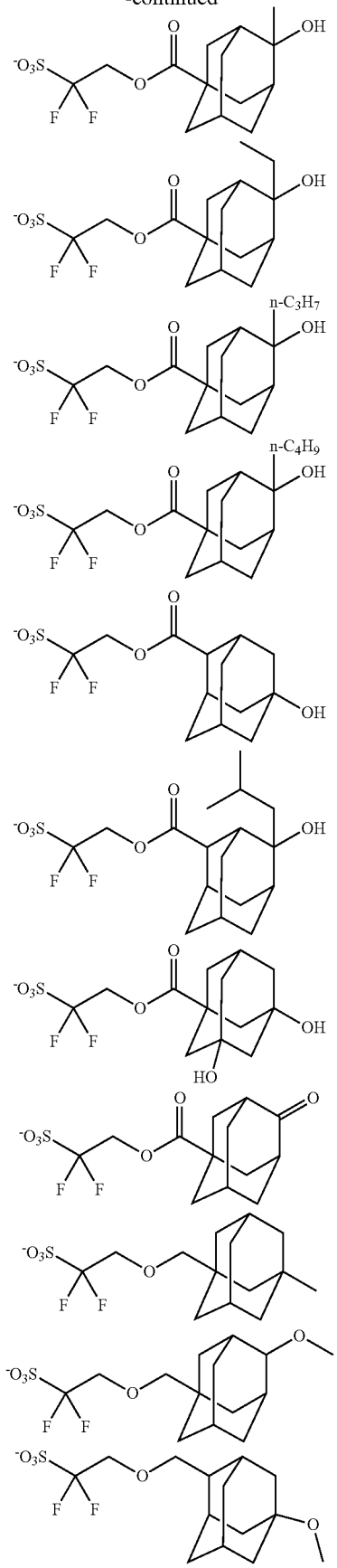
72
-continued
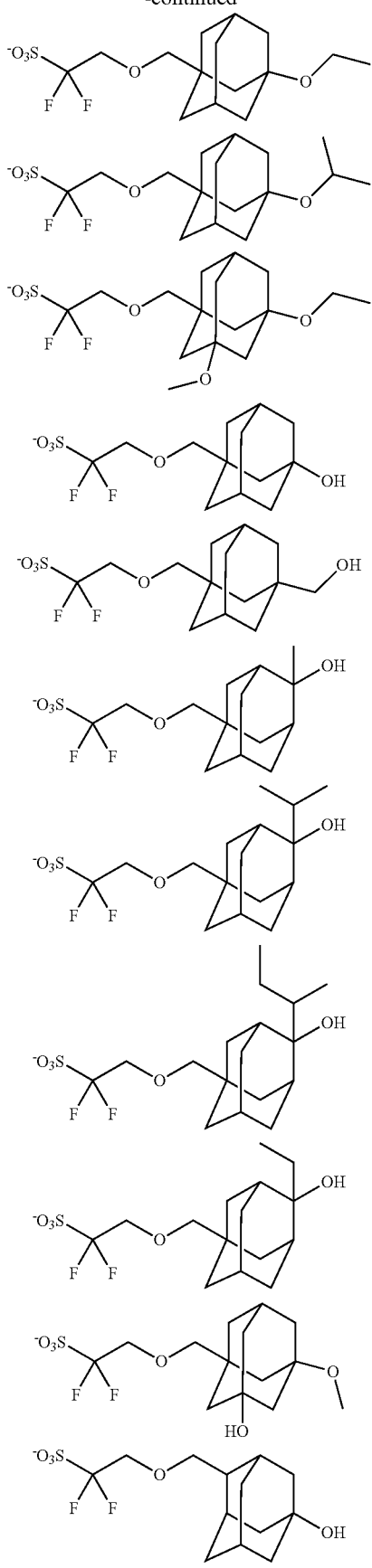

-continued

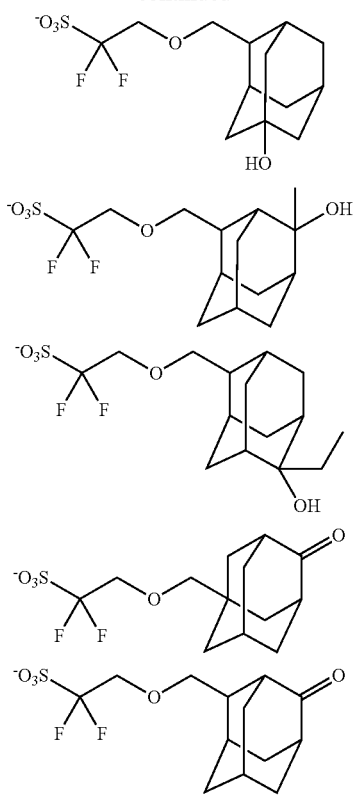

Among them, the following sulfonic anions are preferable.

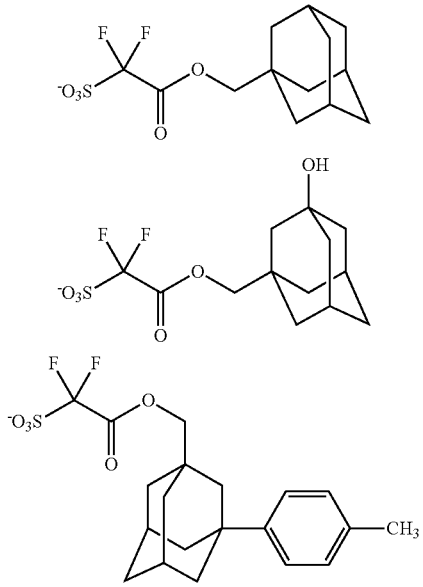

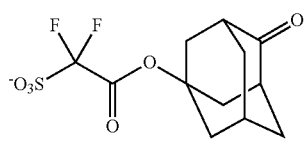

-continued

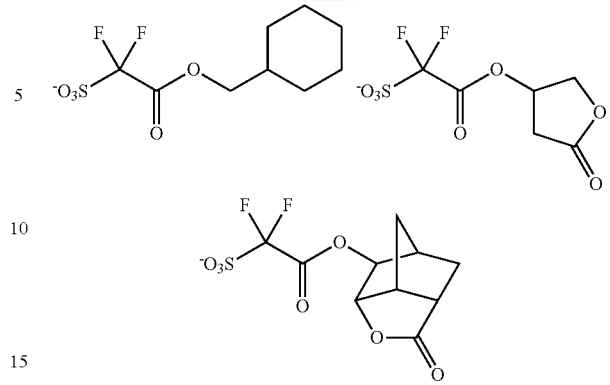

Examples of the cation part represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation part represented by $Z^+$ include the cations represented by the formulae (b2-1) to (b2-4):

(b2-1)

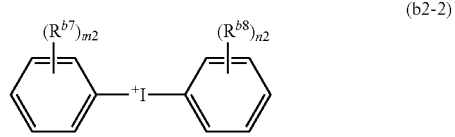

(b2-2)

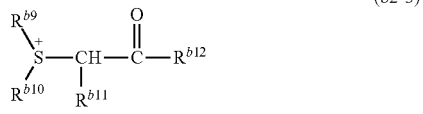

(b2-3)

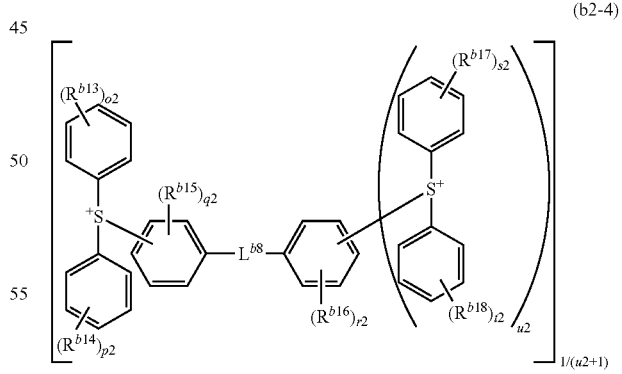

(b2-4)

wherein $R^{b4}$, $R^{b5}$ and $R^{b6}$ each independently represent a linear, branched chain or cyclic C1-C30 aliphatic hydrocarbon group which can have one or more substituents selected from the group consisting of a hydroxyl group, a linear or branched chain C1-C12 alkoxy group and a C6-C18 aromatic hydrocarbon group, or a C6-C18 aromatic hydrocarbon group which can have one or more substituents selected from the group consisting of a hydroxyl group, a linear or branched chain C1-C12 alkoxy group and a linear, branched chain or cyclic C1-C30 aliphatic hydrocarbon group, $R^{b7}$ and $R^{b8}$ are independently in each occurrence a hydroxyl group, a linear or branched chain C1-C12 aliphatic hydrocarbon group or a linear or branched chain C1-C12 alkoxy group, m2 and n2 independently represents an integer of 0 or 1, $R^{b9}$ and $R^{b10}$ each independently represent a linear or branched chain C1-C12 aliphatic hydrocarbon group or a C3-C36 alicyclic hydrocarbon group, or $R^{b9}$ and $R^{b10}$ are bonded to form a C3-C12 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a linear or branched chain C1-C12 aliphatic hydrocarbon group or a C4-C36 alicyclic hydrocarbon group or a C6-C18 aromatic hydrocarbon group, $R^{b12}$ represents a linear or branched chain C1-C12 aliphatic hydrocarbon group or a C6-C18 aromatic hydrocarbon group and the aromatic hydrocarbon group can have one or more substituents selected from the group consisting of a hydroxyl group, a linear or branched chain C1-C12 aliphatic hydrocarbon group and a linear or branched chain C1-C12 alkoxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a linear or branched chain C1-C12 aliphatic hydrocarbon group or a linear or branched chain C1-C12 alkoxy group, $L^{b8}$ represents a sulfur atom or an oxygen atom and o2 to t2 each independently represents an integer of 0 to 2, and u2 represents 0 or 1.

Examples of the aliphatic hydrocarbon group and the aromatic hydrocarbon group include the same as described above. Preferable examples of the linear or branched chain aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. A C4-C12 cyclic aliphatic hydrocarbon group is preferable. Preferable examples of the cyclic aliphatic hydrocarbon group include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

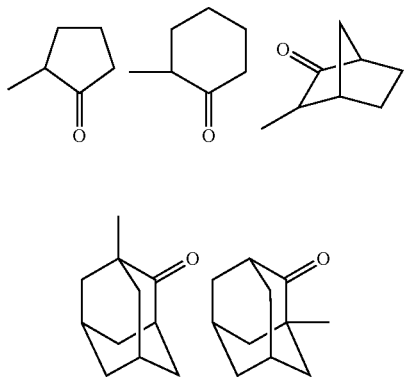

Among the above-mentioned cations, the cation represented by the formula (b2-1) is preferable, and the cation represented by the formula (b2-1-1) is more preferable and a triphenylsulfonium cation is especially preferable.

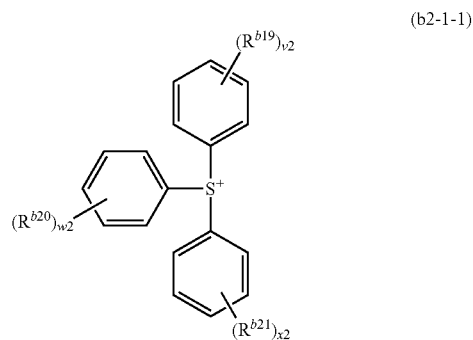

(b2-1-1)

wherein $P^{b19}$, $P^{b20}$ and $P^{b21}$ are independently in each occurrence a hydroxyl group, a linear or branched chain C1-C12 aliphatic hydrocarbon group, or a linear or branched chain C1-C12 alkoxy group, or a C4-C36 alicyclic hydrocarbon group, and one or more hydrogen atoms of the C4-C36 alicyclic hydrocarbon group can be replaced by a halogen atom, a hydroxyl group, a linear or branched chain C1-C12 aliphatic hydrocarbon group, a linear or branched chain C1-C12 alkoxy group, a C6-C12 aryl group, a C7-C12 aralkyl group, a glycidyloxy group or a C2-C4 acyl group, and v2, w2 and x2 independently each represent an integer of 0 to 3. Preferable examples of the alicyclic hydrocarbon group include a group having an adamantane ring or an isobornane ring, and a 2-alkyl-2-adamantyl group, a 1-(1-adamantyl)-1-alkyl group and an isobornyl group are more preferable.

Examples of the cation represented by the formula (b2-1) include the followings.

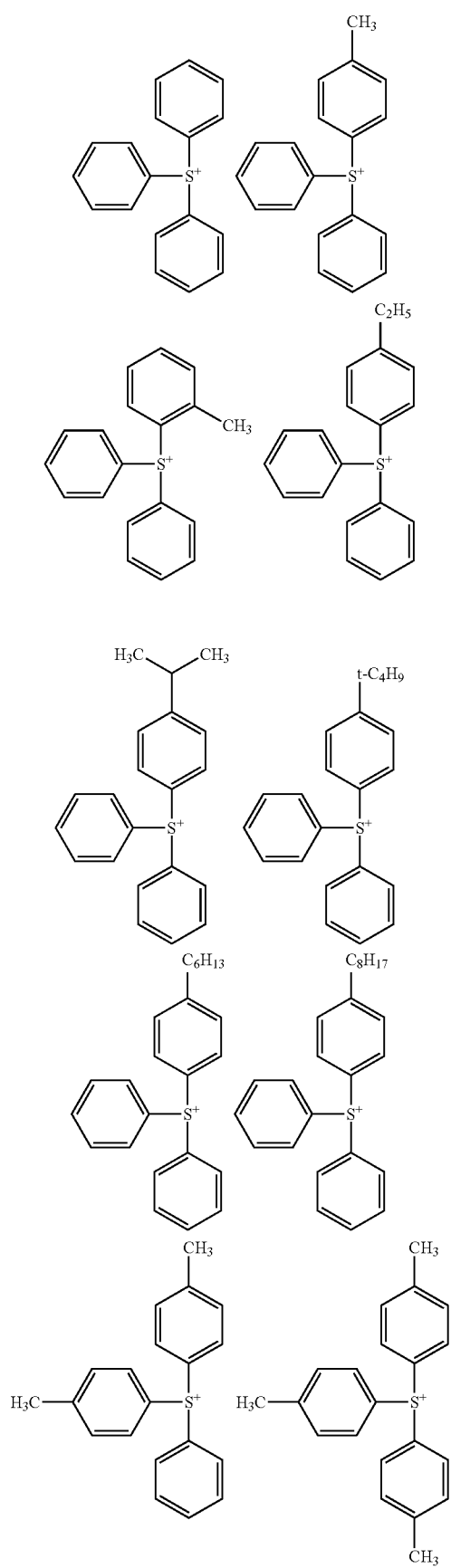
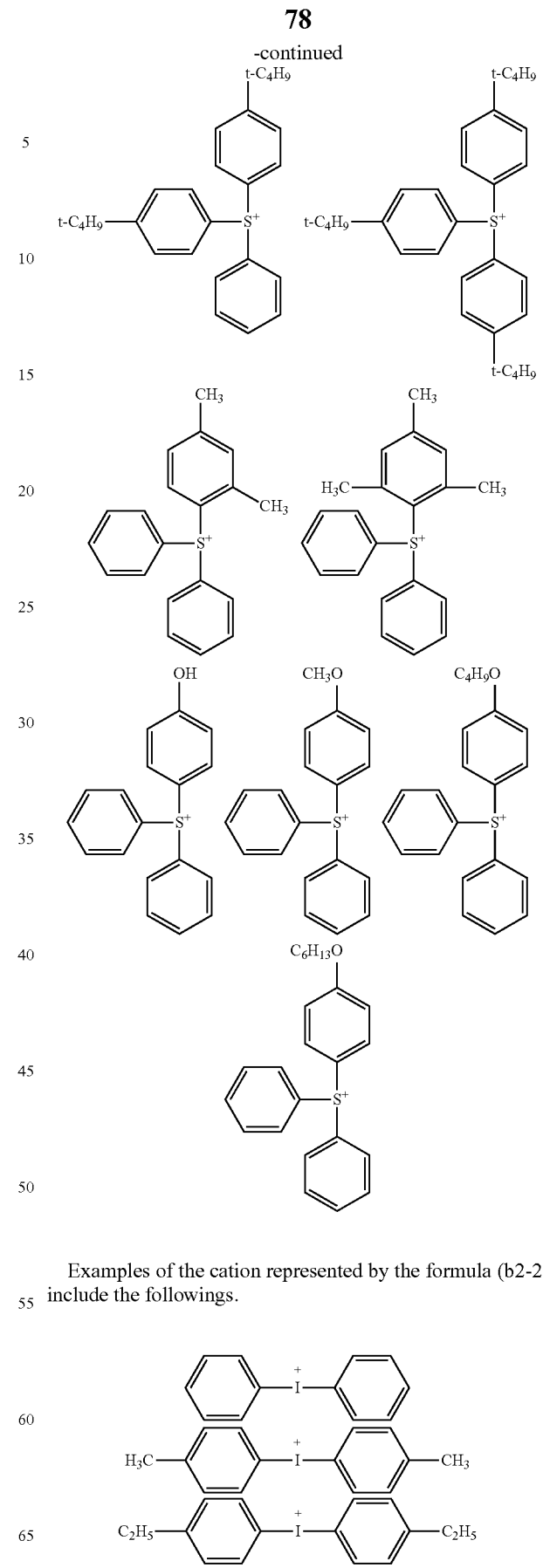
Examples of the cation represented by the formula (b2-2) include the followings.
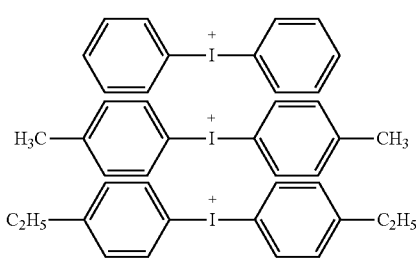

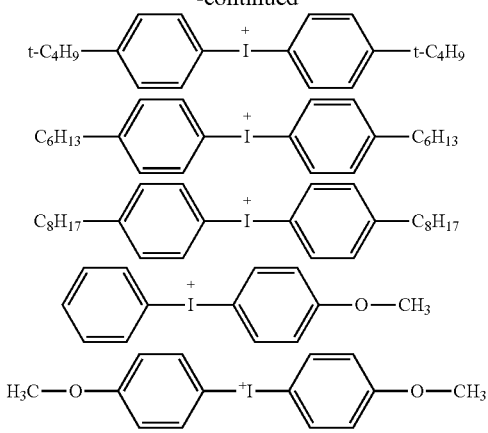
Examples of the cation represented by the formula (b2-3) include the followings.
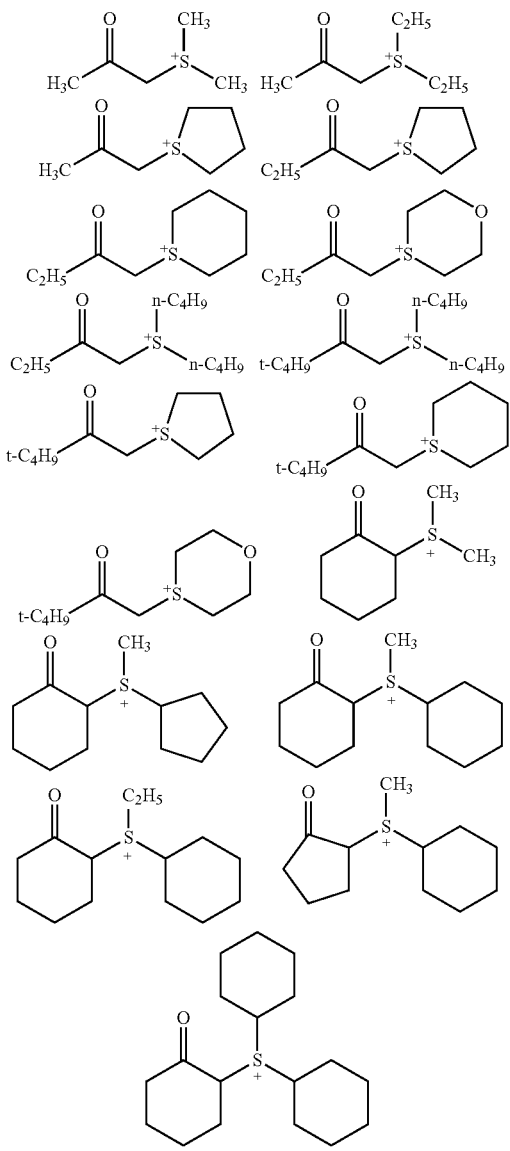
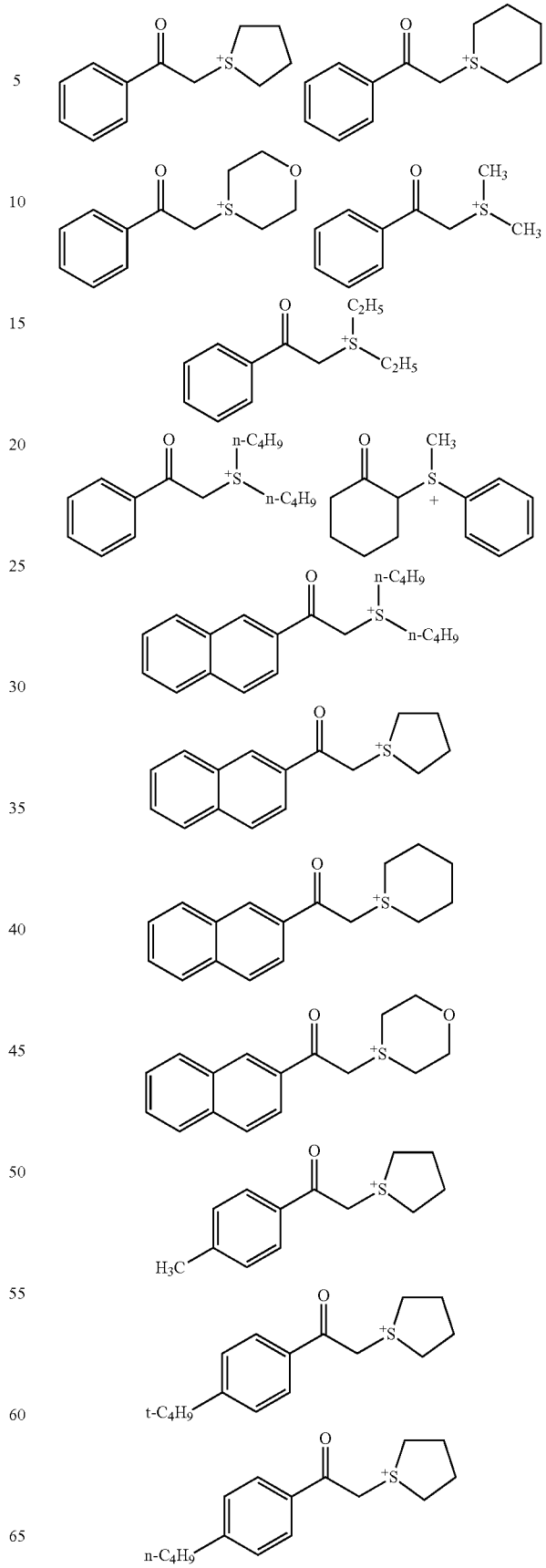

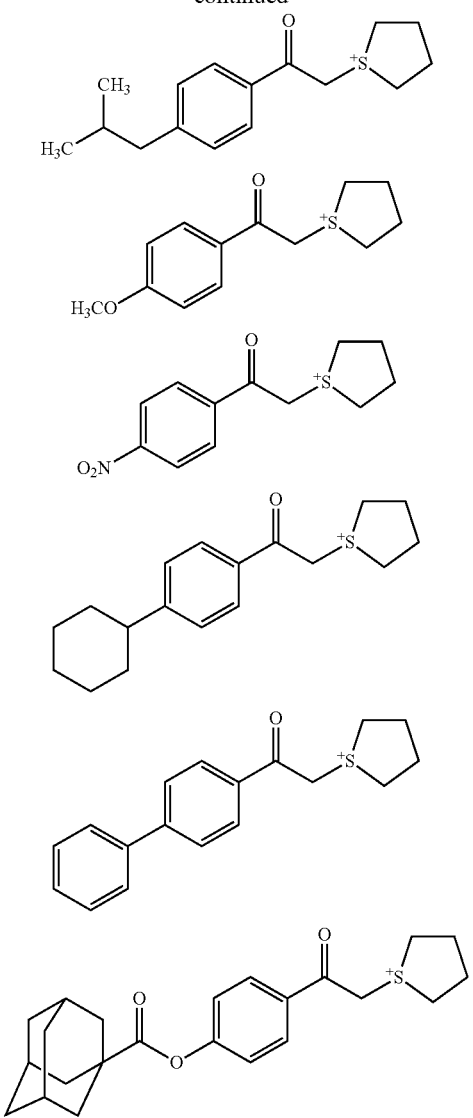
Examples of the cation represented by the formula (b2-4) include the followings.
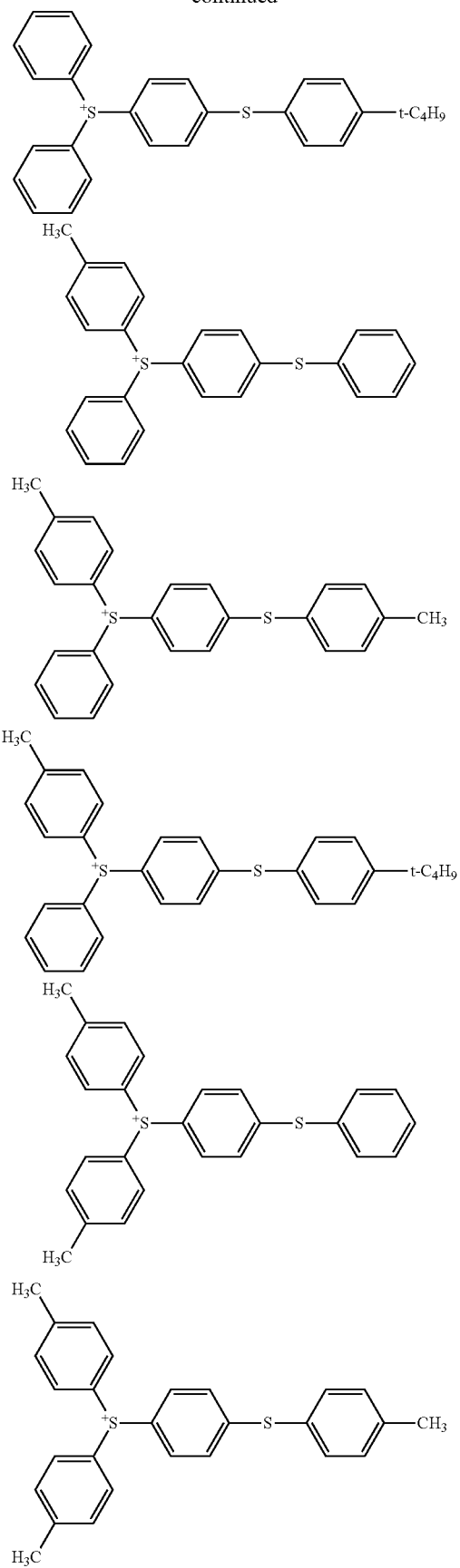

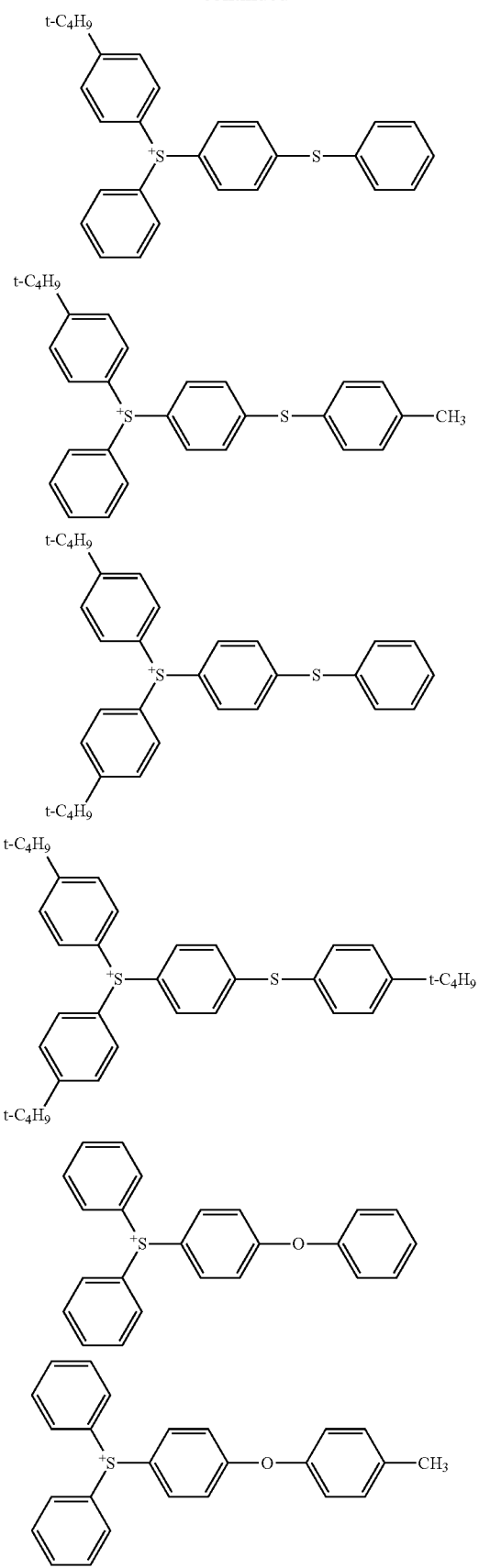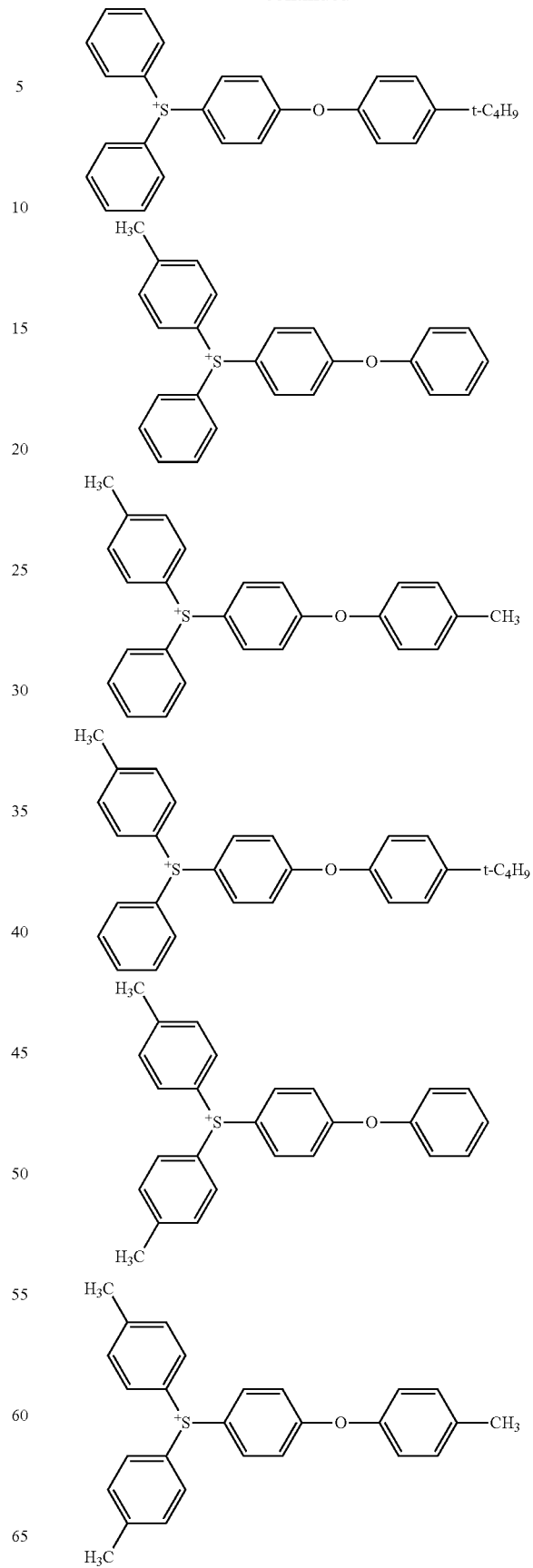

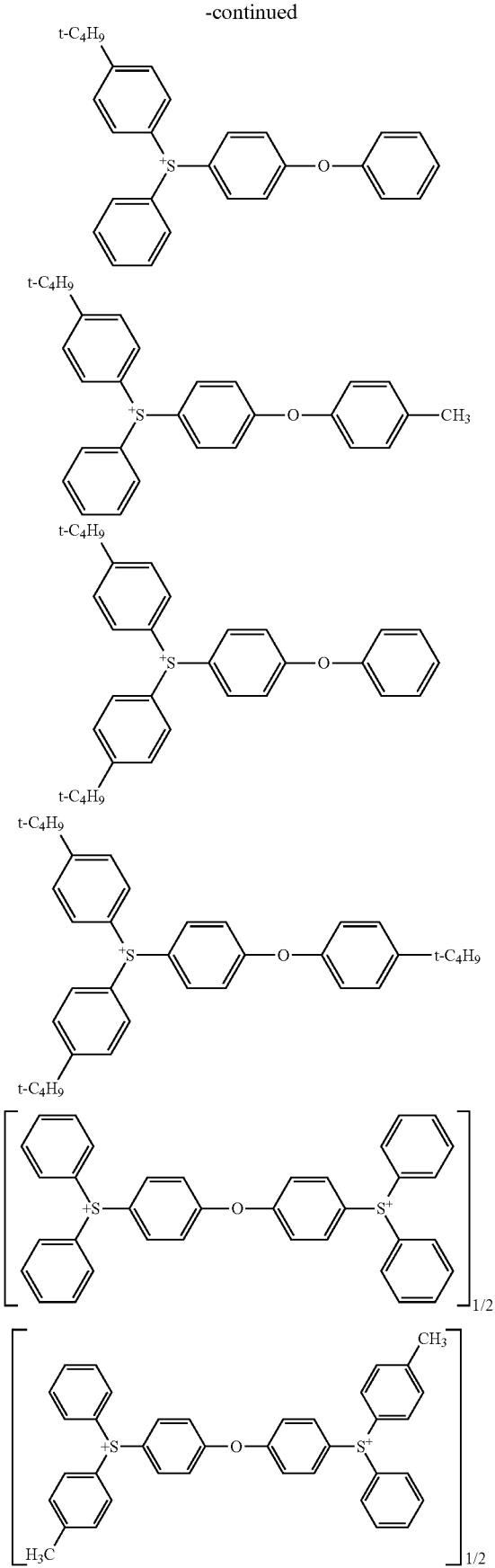

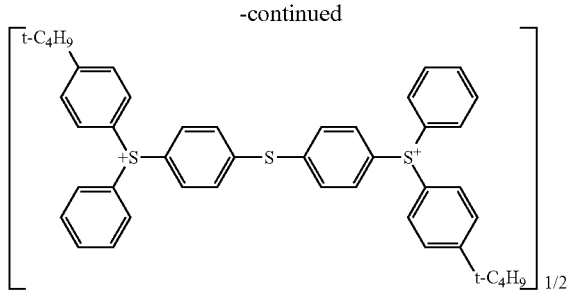

(B1-3)
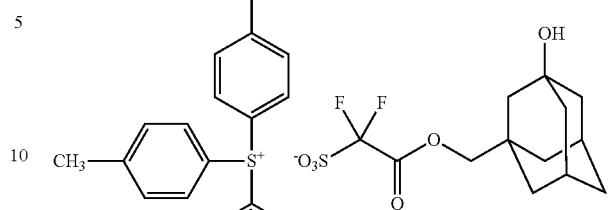

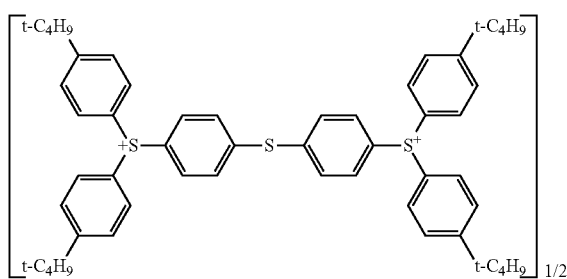

(B1-4)
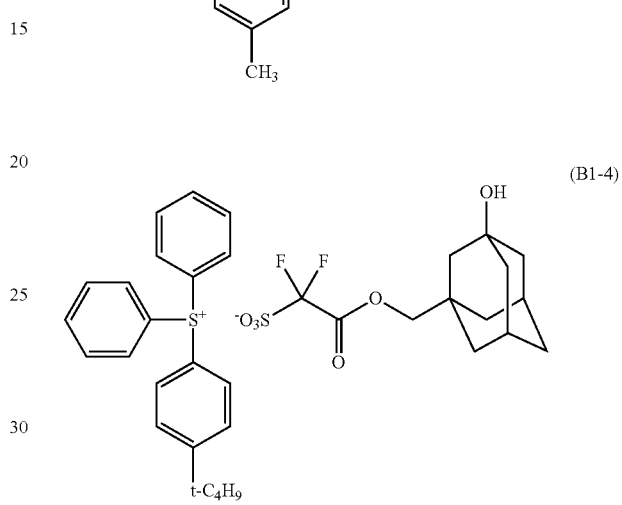

Examples of the salt represented by the formula (B1) include a salt wherein the anion part is any one of the above-mentioned anion part and the cation part is any one of the above-mentioned cation part. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3)

The salt represented by the formulae (B1-1) to (B1-16) are preferable, and the salt represented by the formulae (B1-1), (B1-2), (B1-6), (B1-11), (B1-12), (B1-13) and (B1-14) are more preferable.

(B1-1)
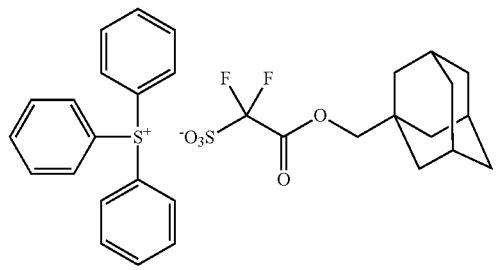

(B1-5)
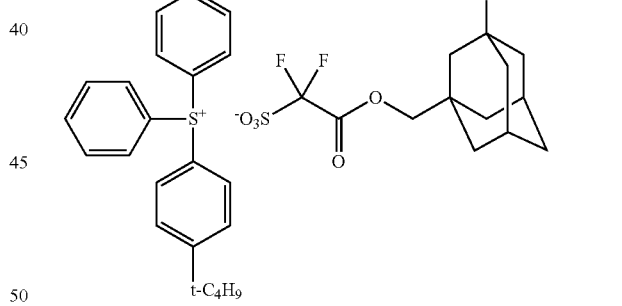

(B1-2)
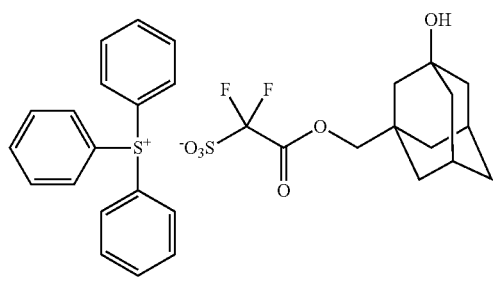

(B1-6)
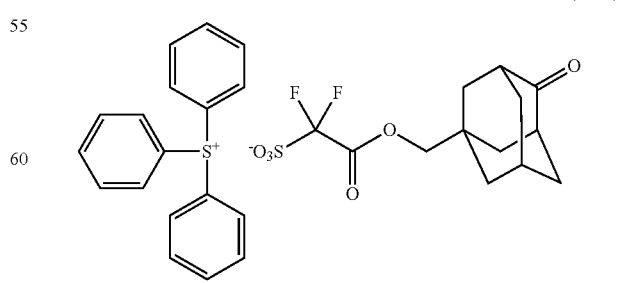

-continued
(B1-7)
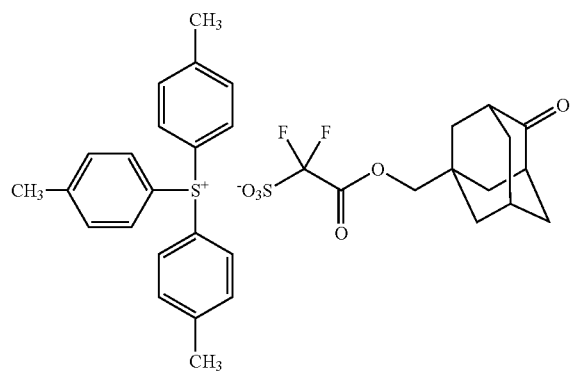
(B1-8)
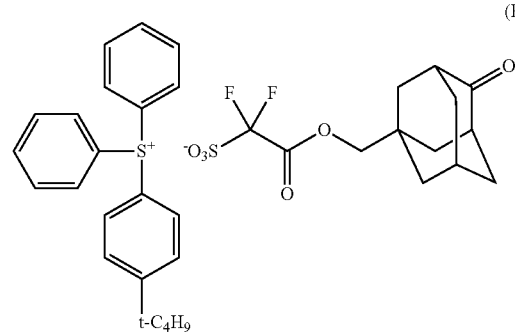
(B1-9)
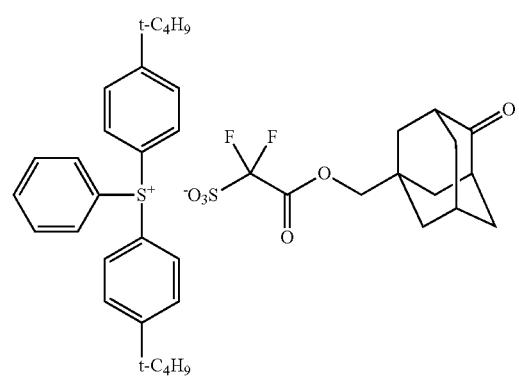
(B1-10)
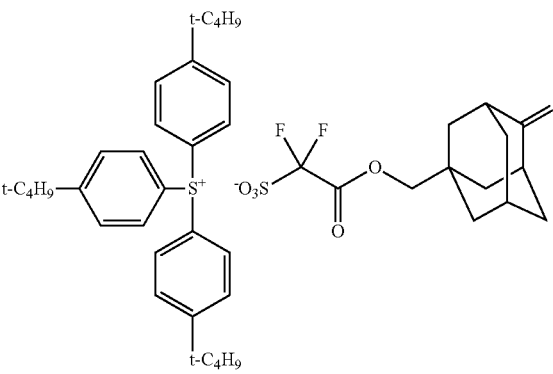
-continued
(B1-11)
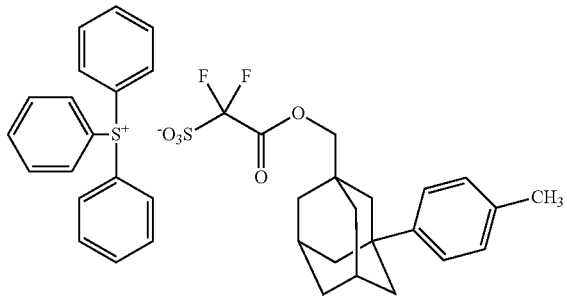
(B1-12)
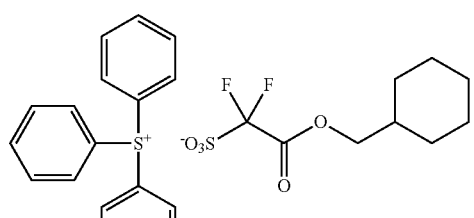
(B1-13)
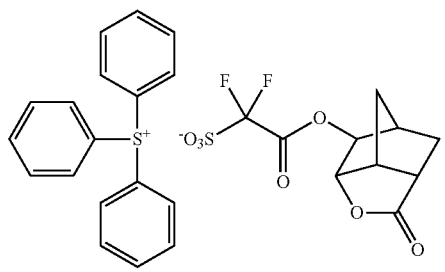
(B1-14)
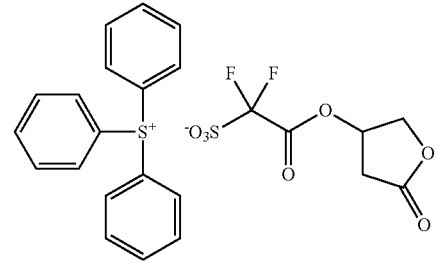
(B1-15)
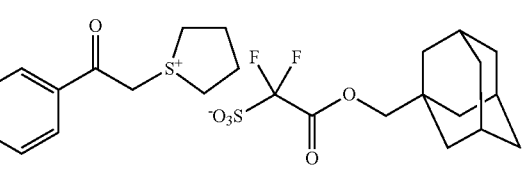
(B1-16)
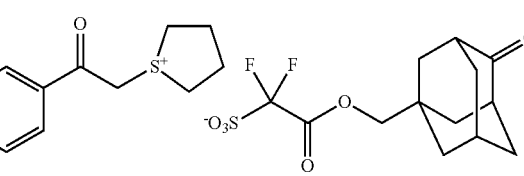
Two or more kinds of the acid generator can be used in combination.
The salt represented by the formula (B1) can be produced, for example, by exchanging $M_a^+$ of the salt represented by the formula (b3-1) for $Z^+$ of the salt represented by the formula (b3-2) as shown in the following scheme:

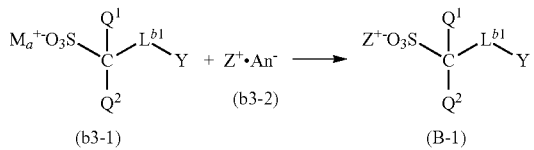

(b3-1)  (b3-2)  (B-1)

wherein $Q^1$, $Q^2$, $L^{b1}$, Y and $Z^+$ are the same as defined above, $M_a^+$ represents $Li^+$, $Na^+$, $K^+$ or $Ag^+$, and $A_n^-$ represents $F^-$, $Cl^-$, $Br^-$, $I^-$, $BF_4^-$, $AsF_6^-$, $SbF_6^-$, $PF_6^-$ or $ClO_4^-$.

The above-mentioned cation exchange reaction is usually conducted in an inert solvent such as acetonitrile, water, methanol, chloroform and dichloromethane, at a temperature of about 0 to about 150° C., preferably of about 0 to about 100° C., with stirring. The amount of the salt represented by the formula (b3-2) is usually 005 to 2 moles per 1 mole of the salt represented by the formula (b3-1). The obtained salt represented by the formula (B1) by the process above can be isolated by recrystallization, and can be purified by washing with water.

The salt of the formula (b3-1) can be produced as described below.

For example, the salt represented by the formula (b3-1-1) can be produced by reacting a salt represented by the formula (b4-1) with an alcohol compound represented by the formula (b4-2) as shown in the following scheme:

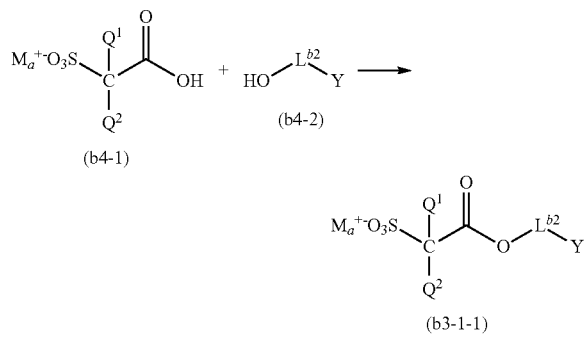

(b4-1)

(b3-1-1)

wherein $Q^1$, $Q^2$, $L^{b2}$, Y and $M_a^+$ are the same as defined above

The amount of the salt represented by the formula (b4-1) is usually 0.2 to 3 moles and preferably 0.5 to 2 moles per 1 mole of the alcohol compound represented by the formula (b4-2)

The salt represented by the formula (b3-1-1) can be also produced by reacting a compound represented by the formula (b4-3) with the alcohol compound represented by the formula (b4-2) followed by hydrolysis with $M_bOH$ as shown in the following scheme:

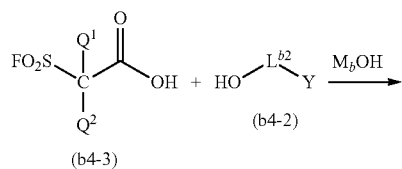

(b4-3)

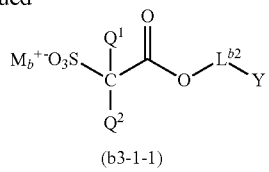

(b3-1-1)

wherein $Q^1$, $Q^2$, $L^{b2}$ and Y are the same as defined above, and $M_b$ represents an alkali metal atom. Examples of the alkali metal atom include lithium atom, sodium atom and potassium atom, and lithium atom and sodium atom are preferable.

The amount of the compound represented by the formula (b4-3) is usually 0.2 to 3 moles and preferably 0.5 to 2 moles per 1 mole of the alcohol compound represented by the formula (b4-2)

Hereinafter, the reaction of the alcohol compound represented by the formula (b4-2) and the salt represented by the formula (b4-1), and the reaction of the alcohol compound represented by the formula (b4-2) and the compound represented by the formula (b4-3) are collectively referred as the esterification reaction.

The esterification reaction is usually conducted in an aprotic solvent such as dichloroethane, toluene, ethylbenzene, monochlorobenzene, acetonitrile and N,N-dimethylformamide, at a temperature of about 20 to 200° C., preferably of 50 to 150° C., with stirring. The esterification reaction can be carried out in the presence of an acid catalyst. Examples of the acid catalyst include organic acids such as p-toluenesulfonic acid, and inorganic acids such as sulfuric acid. While the used amount of the acid catalyst is not limited, it is usually about 0.001 to 5 moles per 1 mole of the salt represented by the formula (b4-1) or the compound represented by the formula (b4-3).

The esterification reaction can be conducted with dehydration because the reaction time tends to be shortened. Examples of the dehydration method include Dean and Stark method. The esterification reaction can be carried out in the presence of a dehydrating agent, and examples of the dehydrating agent include dicyclohexylcarbodiimide, 1-alkyl-2-halopyridinium salt, 1,1'-carbonyldiimidazole, bis(2-oxo-3-oxazolidinyl) phosphinic chloride, 1-ethyl-3-(3-dimethylaminopropyl) carbodiimide hydrochloric acid salt, di-2-pyridyl carbonate, di-2-pyridyl thionocarbonate and 6-methyl-2-nitrobenzoic anhydride with 4-dimethylaminopyridine. While the amount of the dehydrating agent is not limited, it is usually 0.5 to 5 moles, and preferably 1 to 3 moles per 1 mole of the salt represented by the formula (b4-1) or the compound represented by the formula (b4-3)

The salt represented by the formula (B1) wherein is -$L^{b1}$-Y is the group represented by the formula (b1-2) can be produced according to the same manner as described in the above process for producing the salt represented by the formula (b3-1-1)

The salt represented by the formula (b3-1-3) can be produced by reacting a salt represented by the formula (b4-4) with a carboxylic acid compound represented by the formula (b4-5) or the halide compound thereof represented by the formula (b4-6) as shown in the following scheme:

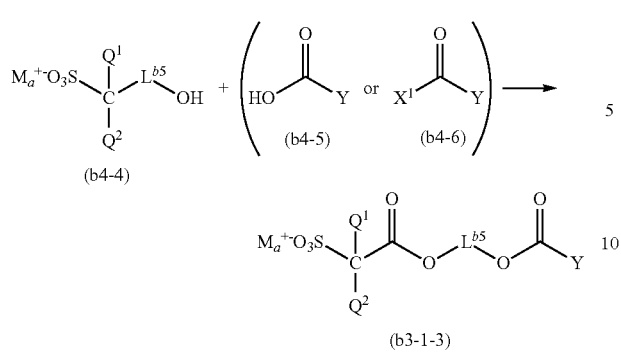

wherein $Q^1$, $Q^2$, $L^{b5}$, Y and $M_a^+$ are the same as defined above, and $X^1$ represents a halogen atom.

The salt represented by the formula (b3-1-1) can be also produced by reacting a compound represented by the formula (b4-7) with the carboxylic acid compound represented by the formula (b4-5) or a halide compound represented by the formula (b4-6) followed by hydrolysis with $M_bOH$ as shown in the following scheme:

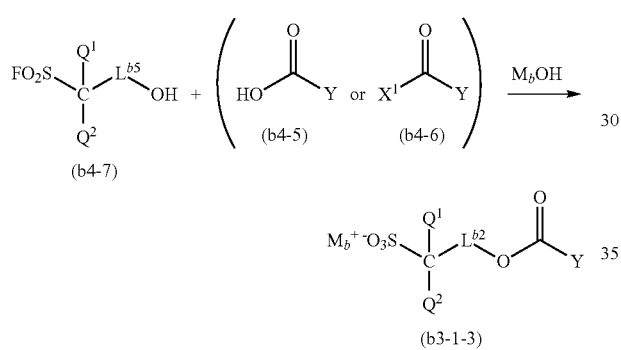

wherein $Q^1$, $Q^2$, $L^{b5}$, $M_b$ and $X^1$ are the same as defined above

The amount of the salt represented by the formula (b4-4) is usually 0.5 to 3 moles and preferably 1 to 2 moles per 1 mole of the carboxylic acid compound represented by the formula (b4-5) or a halide compound represented by the formula (b4-6). The amount of the compound represented by the formula (b4-7) is usually 0.5 to 3 moles and preferably 1 to 2 moles per 1 mole of the carboxylic acid compound represented by the formula (b4-5) or the halide compound thereof represented by the formula (b4-6). The above-mentioned reactions can be conducted according to the same manner as described in the above esterification reaction. When the halide compound represented by the formula (b4-6) is used, the reaction can be carried out in the presence of a base. Examples of the base include an organic base such as triethylamine and pyridine, and an inorganic base such as sodium hydroxide and potassium carbonate. While the used amount of the base is not limited, it is usually 0.001 to 5 moles and preferably 1 to 3 moles per 1 mole of the halide compound represented by the formula (b4-6). The halide compound represented by the formula (b4-6) can be produced by reacting the carboxylic acid compound represented by the formula (b4-5) with a halogenating agent such as thionyl chloride, thionyl bromide, phosphorous trichloride, phosphorous pentachloride and phosphorous tribromide The reaction of the carboxylic acid compound represented by the formula (b4-5) and the halogenating agent is usually conducted in an aprotic solvent such as dichloroethane, toluene, ethylbenzene, monochlorobenzene and N, N-dimethylformamide, at a temperature of about 20 to 200° C., preferably of 50 to 150° C., with stirring. This reaction can be carried out in the presence of an amine catalyst.

The salt represented by the formula (b3-1-4) can be produced by reacting a salt represented by the formula (b4-8) with the alcohol compound represented by the formula (b4-9) or a compound represented by the formula (b4-10) as shown in the following scheme:

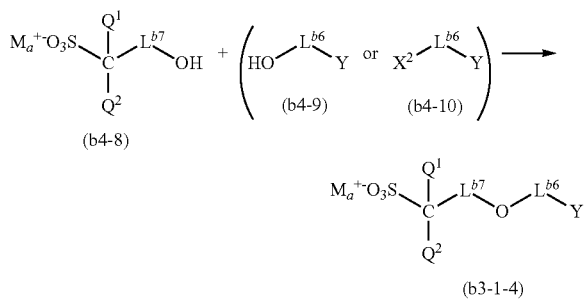

wherein $Q^1$, $Q^2$, $L^{b6}$, $L^{b7}$, $M_a^+$ and Y are the same as defined above, and $X^2$ represents a chlorine atom, a bromine atom, an iodine atom, a methanesulfonyloxy group, a p-toluenesulfonyloxy group or a trifluoromethanesulfonyloxy group.

The salt represented by the formula (b3-1-4) can be also produced by reacting a compound represented by the formula (b4-11) with the alcohol compound represented by the formula (b4-9) or the compound represented by the formula (b4-10) followed by hydrolysis with $M_bOH$ as shown in the following scheme:

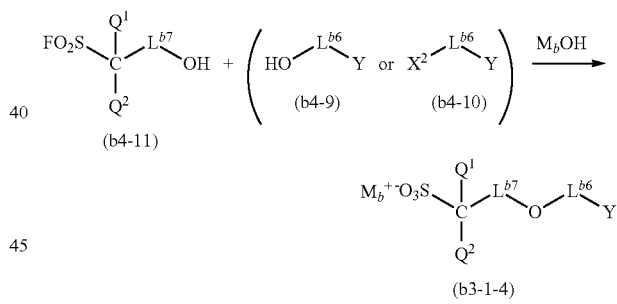

wherein $Q^1$, $Q^2$, $L^{b6}$, $L^{b7}$, $M_b$, Y, and $X^2$ are the same as defined above.

The amount of the salt represented by the formula (b4-8) is usually 0.5 to 3 moles and preferably 1 to 2 moles per 1 mole of the alcohol compound represented by the formula (b4-9) or the compound represented by the formula (b4-10). The amount of the compound represented by the formula (b4-11) is usually 0.5 to 3 moles and preferably 1 to 2 moles per 1 mole of the alcohol compound represented by the formula (b4-9) or the compound thereof represented by the formula (b4-10).

Hereinafter, the reaction of the salt represented by the formula (b4-8) and the alcohol compound represented by the formula (b4-9) or the compound represented by the formula (b4-10), and the reaction of the compound represented by the formula (b4-11) with the alcohol compound represented by the formula (b4-9) or the compound represented by the formula (b4-10) are collectively referred to the etherification reaction.

The etherification reaction is usually conducted in an aprotic solvent such as dichloroethane, toluene, ethylbenzene, monochlorobenzene, acetonitrile and N,N-dimethylformamide, at a temperature of about 20 to 200° C., preferably of 50 to 150° C., with stirring. The etherification reaction can be carried out in the presence of an acid catalyst. Examples of the acid catalyst include organic acids such as p-toluenesulfonic acid, and inorganic acids such as sulfuric acid. While the used amount of the acid catalyst is not limited, it is usually about 0.001 to 5 moles per 1 mole of the alcohol compound represented by the formula (b4-9) or the compound represented by the formula (b4-10). The etherification reaction can be conducted with dehydration because the reaction time tends to be shortened. Examples of the dehydration method include Dean and Stark method. The etherification reaction can be carried out in the presence of a dehydrating agent, and examples of the dehydrating agent include dicyclohexylcarbodiimide and 1,1'-carbonyldiimidazole. While the amount of the dehydrating agent is not limited, it is usually 0.5 to 5 moles, and preferably 1 to 3 moles per 1 mole of the alcohol compound represented by the formula (b4-9) or the compound represented by the formula (b4-10). When the compound represented by the formula (b4-10) is used, the reaction can be carried out in the presence of a base. Examples of the base include an organic base such as triethylamine and pyridine, and an inorganic base such as sodium hydroxide and potassium carbonate While the used amount of the base is not limited, it is usually 0.001 to 5 moles and preferably 1 to 3 moles per 1 mole of the compound represented by the formula (b4-10). The compound represented by the formula (b4-10) can be produced by reacting the alcohol compound represented by the formula (b4-9) with thionyl chloride, thionyl bromide, phosphorous trichloride, phosphorous pentachloride, phosphorous tribromide, methanesulfonyl chloride, p-toluenesulfonyl chloride or trifluoromethanesulfonic anhydride. This reaction is usually conducted in an aprotic solvent such as dichloroethane, toluene, ethylbenzene, monochlorobenzene and N,N-dimethylformamide, at a temperature of about −70 to 200° C., preferably of −50 to 150° C., with stirring. This reaction can be carried out in the presence of a base. Examples of the base include an organic base such as triethylamine and pyridine, and an inorganic base such as sodium hydroxide and potassium carbonate. While the used amount of the base is not limited, it is usually 0.001 to 5 moles and preferably 1 to 3 moles per 1 mole of the alcohol compound represented by the formula (b-4-9).

The photoresist composition of the present invention can contain a nitrogen-containing basic compound in addition to the resin, the acid generator and the compound (C1).

Examples of the nitrogen-containing basic compound include an amine compound and an ammonium hydroxide compound. Examples of the amine compound include an aliphatic amine compound and an aromatic amine compound. Examples of the aliphatic amine compound include a primary aliphatic amine compound, a secondary aliphatic amine compound and a tertiary aliphatic amine compound. Examples of the aromatic amine compound include a compound wherein an amino group is bonded to an aromatic group such as aniline, and a heteroaromatic amine compound such as pyridine. An aromatic amine represented by the formula (Q1) is preferable and an aniline compound represented by the formula (Q1-1) is more preferable.

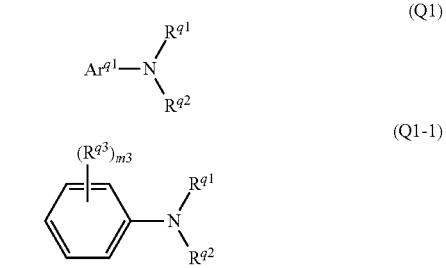

wherein $Ar^{q1}$ represents an aromatic hydrocarbon group, $R^{q1}$ and $R^{q2}$ each independently represent a hydrogen atom, a linear, branched chain or cyclic aliphatic hydrocarbon group or an aromatic hydrocarbon group, and one or more hydrogen atoms of the aliphatic hydrocarbon group and the aromatic hydrocarbon group can be replaced by a hydroxyl group, an amino group or a linear or branched chain C1-C6 alkoxy group, and the amino group can have one or two linear or branched chain C1-C4 alkyl group, $R^{q3}$ is independently in each occurrence a linear, branched chain or cyclic aliphatic hydrocarbon group, a linear or branched chain alkoxy group or an aromatic hydrocarbon group, and one or more hydrogen atoms of the aliphatic hydrocarbon group, the alkoxy group and the aromatic hydrocarbon group can be replaced by a hydroxyl group, an amino group or a linear or branched chain C1-C6 alkoxy group, and the amino group can have one or two linear or branched chain C1-C4 alkyl group, and m3 represents an integer of 0 to 3.

The preferable examples of the linear, branched chain or cyclic aliphatic hydrocarbon group of $R^{q1}$, $R^{q2}$ and $R^{q3}$ include a linear or branched chain alkyl group and a cycloalkyl group. The linear or branched chain aliphatic hydrocarbon group has preferably 1 to 6 carbon atoms, and the cyclic aliphatic hydrocarbon group has preferably 5 to 10 carbon atoms, and the aromatic hydrocarbon group has preferably 6 to 10 carbon atoms. The alkoxy group of $R^{q3}$ has preferably 1 to 6 carbon atoms.

Examples of the aromatic amine represented by the formula (Q1) include 1-naphthylamine and 2-naphthylamine. Examples of the aniline compound represented by the formula (Q1-1) include aniline, diisopropylaniline, 2-methylaniline, 3-methylaniline, 4-methylaniline, 4-nitroaniline, N-methylaniline, N,N-dimethylaniline and diphenylamine. Among them, diisopropylaniline is preferable, and 2,6-diisopropylaniline is more preferable.

A quaternary ammonium hydroxide represented by the formula (Q2)

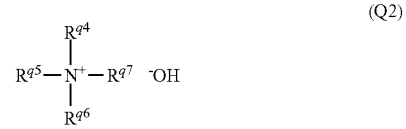

wherein $R^{q4}$, $R^{q5}$ and $R^{q6}$ each independently represent a linear, branched chain or cyclic aliphatic hydrocarbon group or an aromatic hydrocarbon group, and one or more hydrogen atoms of the aliphatic hydrocarbon group and the aromatic hydrocarbon group can be replaced by a hydroxyl group, an amino group or a linear or branched chain C1-C6 alkoxy group, and the amino group can have one or two linear or branched chain C1-C4 alkyl group, and $R^{q7}$ represents a linear, branched chain or cyclic aliphatic hydrocarbon group, and one or more hydrogen atoms of the aliphatic hydrocarbon group can be replaced by a hydroxyl group, an amino group or a linear or branched chain C1-C6 alkoxy group, and the amino group can have one or two linear or branched chain C1-C4 alkyl group, is preferable The preferable examples of the linear, branched chain or cyclic aliphatic hydrocarbon group of $R^{q4}$, $R^{q5}$, $R^{q6}$ and $R^{q7}$ include a linear or branched chain alkyl group and a cycloalkyl group. The linear or branched chain aliphatic hydrocarbon group has preferably 1 to 6 carbon atoms, and the cyclic aliphatic hydrocarbon group has preferably 5 to 10 carbon atoms, and the aromatic hydrocarbon group has preferably 6 to 10 carbon atoms, The alkoxy group of $R^{q3}$ has preferably 1 to 6 carbon atoms.

Examples of the quaternary ammonium hydroxide represented by the formula (Q2) include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammoniumhydroxide (so-called "choline") Among them, tetramethylammonium hydroxide, tetrabutylammonium hydroxide, tetrahexylammonium hydroxide, tetraoctylammonium hydroxide, phenyltrimethylammonium hydroxide and (3-trifluoromethylphenyl)trimethylammonium hydroxide are preferable.

Other examples of the nitrogen-containing compound include the following compounds represented by the formulae (Q3) to (Q11):

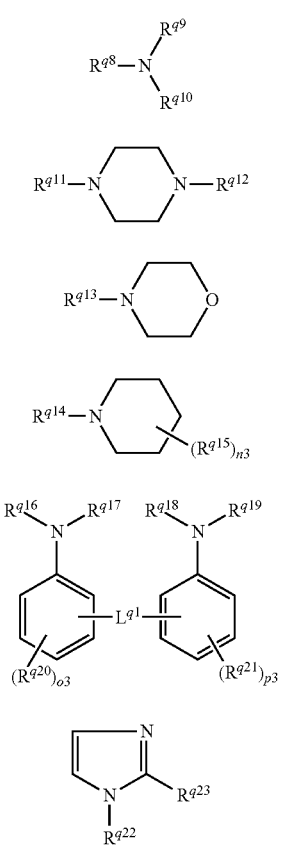

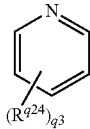

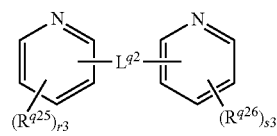

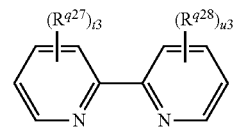

wherein $R^{q8}$ represents a linear, branched chain or cyclic aliphatic hydrocarbon group, and one or more hydrogen atoms of the aliphatic hydrocarbon group can be replaced by a hydroxyl group, an amino group or a linear or branched chain C1-C6 alkoxy group, and the amino group can have one or two linear or branched chain C1-C4 alkyl group, $R^{q9}$, $R^{q10}$, $R^{q11}$, $R^{q12}$, $R^{q13}$, $R^{q14}$, $R^{q16}$, $R^{q17}$, $R^{q18}$, $R^{q19}$ and $R^{q22}$ each independently represent a hydrogen atom, a linear, branched chain or cyclic aliphatic hydrocarbon group or an aromatic hydrocarbon group, and one or more hydrogen atoms of the aliphatic hydrocarbon group and the aromatic hydrocarbon group can be replaced by a hydroxyl group, an amino group or a linear or branched chain C1-C6 alkoxy group, and the amino group can have one or two linear or branched chain C1-C4 alkyl group, $R^{q20}$, $R^{q21}$, $R^{q23}$, $R^{q24}$, $R^{q25}$, $R^{q26}$, $R^{q27}$ and $R^{q28}$ are independently in each occurrence a linear, branched chain or cyclic aliphatic hydrocarbon group, a linear or branched chain alkoxy group or an aromatic hydrocarbon group, and one or more hydrogen atoms of the aliphatic hydrocarbon group, the alkoxy group and the aromatic hydrocarbon group can be replaced by a hydroxyl group, an amino group or a linear or branched chain C1-C6 alkoxy group, and the amino group can have one or two linear or branched chain C1-C4 alkyl group, $R^{q15}$ represents a linear, branched chain or cyclic aliphatic hydrocarbon group or an alkanoyl group, $L^{q1}$ and $L^{q2}$ each independently represent a divalent aliphatic hydrocarbon group, —CO—, —NH—, —S—, —S—S— or a combination thereof, n3 represents an integer of 0 to 8, and o3, p3, q3, r3, s3, t3 and u3 each independently represent an integer of 0 to 3.

The preferable examples of the linear, branched chain or cyclic aliphatic hydrocarbon group of $R^{q8}$ include a linear or branched chain alkyl group and a cycloalkyl group. The linear or branched chain aliphatic hydrocarbon group has preferably 1 to 6 carbon atoms, and the cyclic aliphatic hydrocarbon group has preferably 5 to 10 carbon atoms, and the aromatic hydrocarbon group has preferably 6 to 10 carbon atoms. The alkoxy group has preferably 1 to 6 carbon atoms. The alkanoyl group has preferably 2 to 6 carbon atoms. The divalent aliphatic hydrocarbon group has preferably 2 to 6 carbon atoms. Preferable divalent aliphatic hydrocarbon group is an alkanediyl group.

Examples of the compound represented by the formula (Q3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the compound represented by the formula (Q4) include piperazine. Examples of the compound represented by the formula (Q5) include morpholine. Examples of the compound represented by the formula (Q6) include piperidine and hindered amine compounds having a piperidine skeleton as disclosed in JP 11-52575 A. Examples of the compound represented by the formula (Q7) include 2,2'-methylenebisaniline. Examples of the compound represented by the formula (Q8) include imidazole and 4-methylimidazole. Examples of the compound represented by the formula (Q9) include pyridine and 4-methylpyridine. Examples of the compound represented by the formula (Q10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the compound represented by the formula (Q11) include bipyridine.

When the nitrogen-containing basic compound is used, the present photoresist composition preferably includes 0.01 to 1% by weight of the nitrogen-containing basic compound based on sum of solid component. In this specification, "solid component" means components other than solvent in the photoresist composition.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 60% by weight or more, preferably 80% by weight or more, preferably 90% by weight or more based on total amount of the photoresist composition of the present invention. The amount of the solvent is usually 99.5% by weight or less and preferably 97% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5)

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is of ten used After development, the photoresist pattern formed is preferably washed with ultrapure water, and the remained water on the photoresist pattern and the substrate is preferably removed.

The compound of the present invention is a suitable component of a photoresist composition, and the photoresist composition of the present invention provides a photoresist pattern showing good Mask Error Enhancement Factor (MEEF), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can be used for an immersion lithography and for a dry lithography. Furthermore, the photoresist composition of the present invention can be also used for a double imaging lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: tetrahydrofuran, Flow rate: 1.0 mL/min., Detector: RI detector, Column temperature: 40° C., Injection volume: 100 μL] using standard polystyrene, manufactured by TOSOH CORPORATION, as a standard reference material. Structures of compounds were determined by NMR (EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

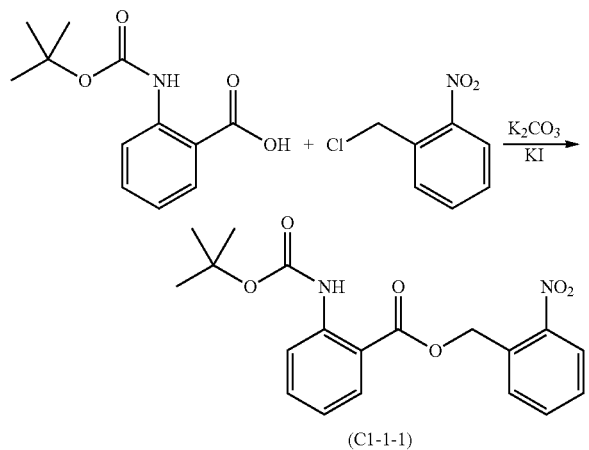

(C1-1-1)

To a solution of 2.0 parts of N-tert-butoxycarbonyl-2-aminobenzoic acid, available from Sigma-Aldrich Corporation, and 20 parts of N,N-dimethylformamide, 0.58 part of potassium carbonate and 0.17 part of potassium iodide were added, and the resultant was stirred at 40° C. for 1 hour. To the mixture, 1.45 parts of 2-nitrobenzyl chloride was added. The obtained mixture was stirred at 40° C. for 4 hours. The obtained reaction mixture was cooled down to room temperature, and 80 parts of saturated aqueous ammonium chloride solution was added thereto, and then, 200 parts of ethyl acetate was added thereto. The resultant mixture was separated to an organic layer and an aqueous layer. The organic layer was washed five times with water and then, was concentrated under reduced pressure to obtain 3.1 parts of a compound represented by the formula (C1-1-1).

$^1$H-NMR (dimethylsulfoxide-$d_6$): δ (ppm) 9.99 (1H, s), 8.16 (2H, t, J=7.6 Hz), 7.96 (1H, d, J=7.9 Hz), 7.84-7.77 (2H, m), 7.70-7.57 (2H, m), 7.17-7.10 (1H, m), 5.67 (2H, s), 1.45 (9H, s)

MS (ESI(+)) Spectrum): [M+Na]$^+$=395.1 ($C_{19}H_{20}N_2O_6$=372.1)

Example 2

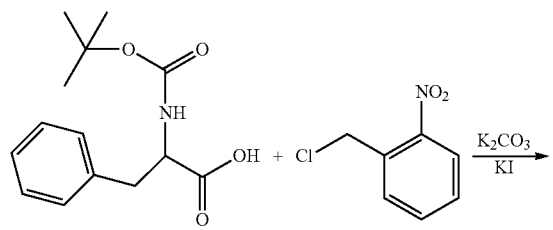

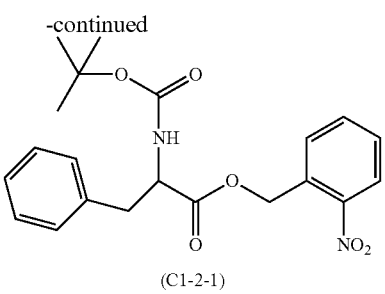

(C1-2-1)

To a solution of 2.0 parts of N-tert-butoxycarbonylphenylalanine, available from Sigma-Aldrich Corporation, and 20 parts of N, N-dimethylformamide, 0.52 part of potassium carbonate and 0.16 part of potassium iodide were added, and the resultant was stirred at 40° C. for 1 hour. To the mixture, 1.29 parts of 2-nitrobenzyl chloride was added. The obtained mixture was stirred at 40° C. for 4 hours. The obtained reaction mixture was cooled down to room temperature, and 80 parts of saturated aqueous ammonium chloride solution was added thereto, and then, 200 parts of ethyl acetate was added thereto. The resultant mixture was separated to an organic layer and an aqueous layer. The organic layer was washed five times with water and then, was concentrated under reduced pressure to obtain 2.5 parts of a compound represented by the formula (C1-2-1).

$^1$H-NMR (dimethylsulfoxide-$d_6$): δ (ppm) 8.12 (1H, d, J=8.2 Hz), 7.79-7.70 (1H, m), 7.65-7.53 (2H, m), 7.47-7.39 (1H, m), 7.32-7.14 (5H, m), 5.44 (2H, s), 4.34-4.13 (1H, m), 3.10-2.82 (2H, m), 1.35 (9H, s)

MS (ESI(+)) Spectrum): [M+Na]$^+$=423.1 ($C_{21}H_{24}N_2O_6$=400.1)

Example 3

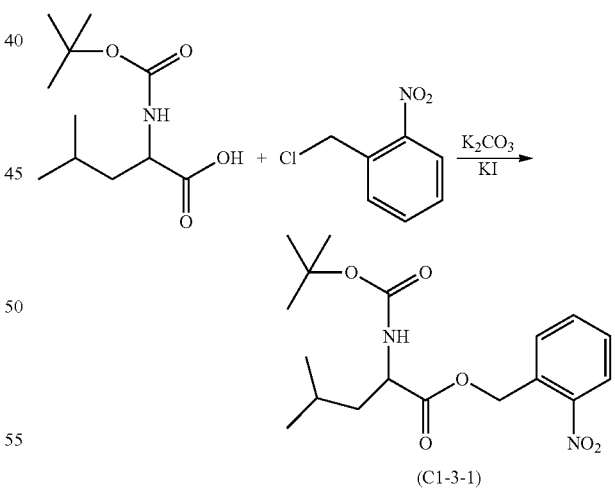

(C1-3-1)

To a solution of 2.0 parts of N-tert-butoxycarbonylleucine, available from Sigma-Aldrich Corporation, and 20 parts of N,N-dimethylformamide, 0.6 part of potassium carbonate and 0.18 part of potassium iodide were added, and the resultant was stirred at 40° C. for 1 hour. To the mixture, 1.48 parts of 2-nitrobenzyl chloride was added. The obtained mixture was stirred at 40° C. for 4 hours. The obtained reaction mixture was cooled down to room temperature, and 80 parts of saturated aqueous ammonium chloride solution was added thereto, and then, 200 parts of ethyl acetate was added thereto. The resultant mixture was separated to an organic layer and an aqueous layer. The organic layer was washed five times with water and then, was concentrated under reduced pressure to obtain 2.4 parts of a compound represented by the formula (C1-3-1).

$^1$H-NMR (dimethylsulfoxide-$d_6$): δ (ppm) 8.11 (1H, d, J=8.2 Hz), 7.84-7.53 (3H, m), 7.35 (1H, d, J=7.6 Hz), 5.52-5.34 (2H, m), 4.12-3.97 (1H, m), 1.70-1.23 (12H, m), 0.89-0.84 (6H, m)

MS (ESI(+) Spectrum): [M+Na]$^+$=389.1 ($C_{18}H_{26}N_2O_6$=366.1)

Example 4

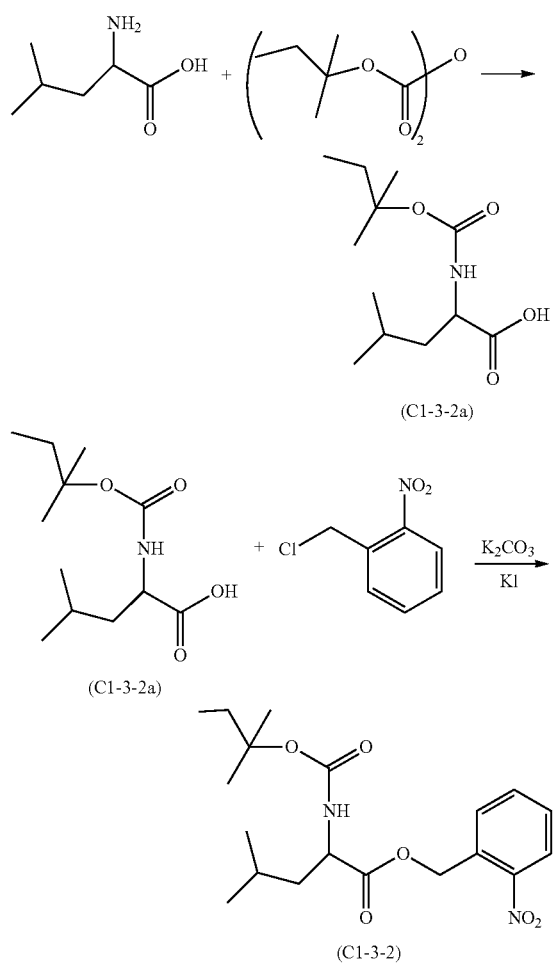

(C1-3-2a)

(C1-3-2)

To a solution of 12.0 parts of leucine, available from Sigma-Aldrich Corporation, 36 parts of 1,4-dioxane and 36 parts of ion-exchanged water, 30 parts of triethylamine and di-tert-amyl dicarbonate, available from Tokyo Chemical Industry Co., Ltd. Were added, and the resultant was stirred at room temperature over night. The obtained reaction mixture was extracted with heptane, and an organic layer and an aqueous layer were obtained. The aqueous layer was mixed with 216 parts of 5% hydrochloric acid and the resultant mixture was extracted with ethyl acetate. The obtained organic layer was dried over magnesium sulfate and concentrated to obtain 23.1 parts of a compound represented by the formula (C1-3-2a)

To a solution of 5.0 parts of the compound represented by the formula (C1-3-2a) and 20 parts of N,N-dimethylformamide, 1.33 parts of potassium carbonate and 0.40 part of potassium iodide were added, and the resultant was stirred at 40° C. for 1 hour. To the mixture, 1.85 parts of 2-nitrobenzyl chloride was added. The obtained mixture was stirred at 40° C. for 2 hours. The obtained reaction mixture was cooled down to room temperature, and 75 parts of ion-exchanged water was added thereto, and then, 150 parts of ethyl acetate was added thereto. The resultant mixture was separated to an organic layer and an aqueous layer. The organic layer was washed five times with water and then, was concentrated under reduced pressure to obtain 10.9 parts of a compound represented by the formula (C1-3-2).

$^1$H-NMR (dimethylsulfoxide-$d_6$): δ (ppm) 8.11 (1H, d, J=7.9 Hz), 7.82-7.56 (3H, m), 7.35 (1H, d, J=7.9 Hz), 5.51-5.36 (2H, m), 4.12-3.96 (1H, m), 1.78-1.21 (11H, m), 0.91-0.69 (9H, m)

MS (ESI(+) Spectrum): [M+Na]$^+$=403.2 ($C_{19}H_{28}N_2O_6$=380.2)

Example 5

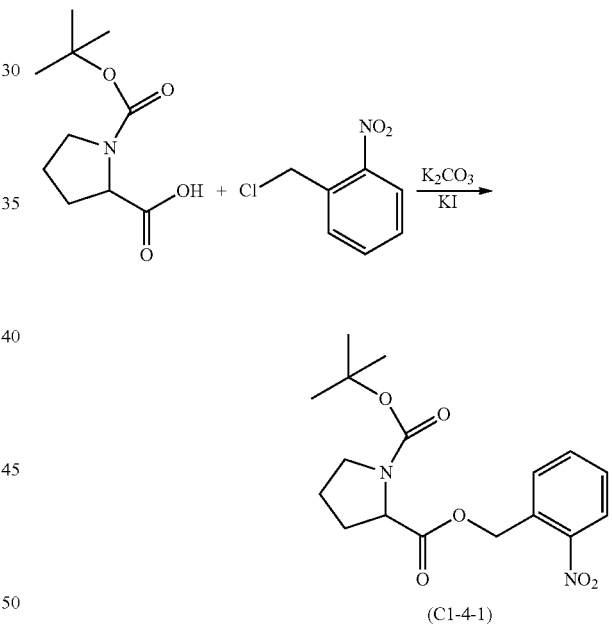

(C1-4-1)

To a solution of 2.0 parts of N-tert-butoxycarbonylphenylalanine and 20 parts of N,N-dimethylformamide, 0.64 part of potassium carbonate and 0.19 part of potassium iodide were added, and the resultant was stirred at 40° C. for 1 hour. To the mixture, 1.59 parts of 2-nitrobenzyl chloride was added. The obtained mixture was stirred at 40° C. The obtained reaction mixture was cooled down to room temperature, and 80 parts of saturated aqueous ammonium chloride solution was added thereto, and then, 200 parts of ethyl acetate was added thereto. The resultant mixture was separated to an organic layer and an aqueous layer. The organic layer was washed five times with water and then, was concentrated under reduced pressure to obtain 2.8 parts of a compound represented by the formula (C1-4-1).

¹H-NMR (dimethylsulfoxide-d₆): δ (ppm) 8.15-8.05 (1H, m), 7.83-7.56 (3H, m), 5.57-5.32 (2H, m), 4.32-4.16 (1H, m), 3.43-3.20 (2H, m), 2.32-2.10 (11H, m), 1.96-1.71 (3H, m), 1.43-1.20 (9H, m)

Example 6

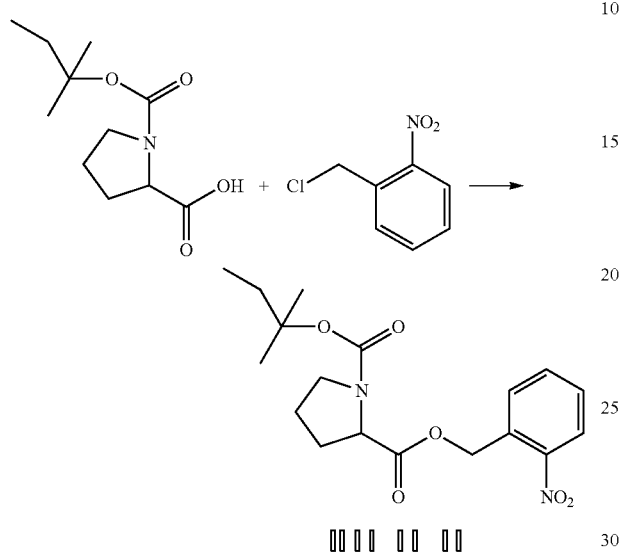

To a solution of 2.0 parts of N-tert-butoxycarbonylphenylalanine and 20 parts of N,N-dimethylformamide, 0.64 part of potassium carbonate and 0.19 part of potassium iodide were added, and the resultant was stirred at 40° C. for 1 hour. To the mixture, 1.59 parts of 2-nitrobenzyl chloride was added. The obtained mixture was stirred at 40° C. The obtained reaction mixture was cooled down to room temperature, and 80 parts of saturated aqueous ammonium chloride solution was added thereto, and then, 200 parts of ethyl acetate was added thereto. The resultant mixture was separated to an organic layer and an aqueous layer. The organic layer was washed five times with water and then, was concentrated under reduced pressure to obtain 2.8 parts of a compound represented by the formula (C1-4-2).

¹H-NMR (dimethylsulfoxide-d₆): δ (ppm) 8.15-8.05 (1H, m), 7.84-7.55 (3H, m), 5.56-5.33 (2H, m), 4.32-4.18 (1H, m), 3.39-3.21 (2H, m), 2.33-2.05 (11H, m), 1.94-1.48 (5H, m), 1.38-1.20 (6H, m), 0.88-0.62 (3H, m)

In Resin Synthesis Example 1, the following monomers were used.

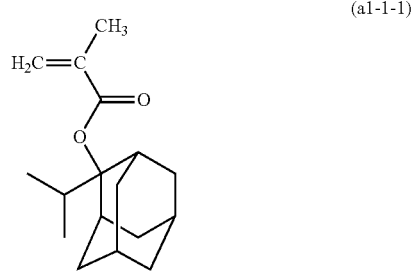

(a1-1-1)

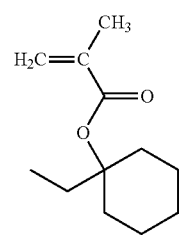

(a1-2-1)

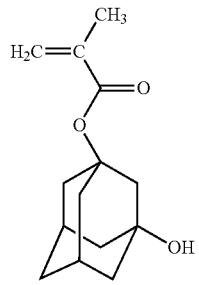

(a2-1-1)

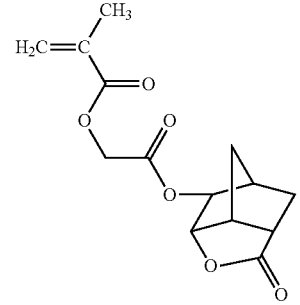

(a3-2-1)

Resin Synthesis Example 1

To a four-necked flask equipped with a thermometer and a reflux condenser, 72.77 parts of 1,4-dioxane was added, and a nitrogen gas was blown into it for 30 minutes. After heating it up to 75° C. under nitrogen, a solution prepared by mixing 76.30 parts of monomer represented by the formula (a1-1-1), 11.42 parts of monomer represented by the formula (a1-2-1), 11.74 parts of monomer represented by the formula (a2-1-1), 52.16 parts of monomer represented by the formula (a3-2-1), 0.96 parts of 2,2'-azobisisobutyronitrile, 4.33 parts of 2,2'-azobis(2,4-dimethylvaleronitrile) and 109.16 parts of 1,4-dioxane was added dropwise thereto over 2 hour at 75° C. The resultant mixture was stirred for 5 hours at 75° C. After cooling the reaction mixture down to room temperature, the reaction mixture was diluted with 212.26 parts of 1,4-dioxane and the resultant solution was poured into a mixture of 536 parts of methanol and 394 parts of water to cause precipitation. The precipitate was isolated and mixed with 985 parts of methanol. The resultant mixture was stirred followed by filtrating to obtain the precipitate. The operation wherein the precipitate was mixed with 985 parts of methanol and the resultant mixture was stirred followed by filtrating to obtain the precipitate was repeated three times. The obtained precipitate was dried under reduced pressure to obtain 112 parts of a resin having a weight-average molecular weight (Mw) of 7,400 and a dispersion degree (Mw/Mn) of 1.83 in a yield of 74%. This resin had the structural units derived from monomers represented by the formulae (a1-1-1), (a1-2-1), (a2-1-1) and (a3-2-1). This is called as resin A1. The ratio of the structural units derived from monomers represented by the formulae (a1-1-1), (a1-2-1), (a2-1-1) and (a3-2-1) ((a1-1-1)/(a1-2-1)/(a2-1-1)/(a3-2-1)) was 40/10/10/40. This ratio is molar ratio of the structural units derived from monomers represented by the formulae (a1-1-1), (a1-2-1), (a2-1-1) and (a3-2-1) and it was calculated based on the amount of the unreacted monomers in the reaction mixture, which was measured by liquid chromatography analysis using LC 2010HT, manufactured by Shimadzu Corporation.

Examples 7 to 12 and Reference Example 1

<Acid Generator>
B1-2: 0.95 part

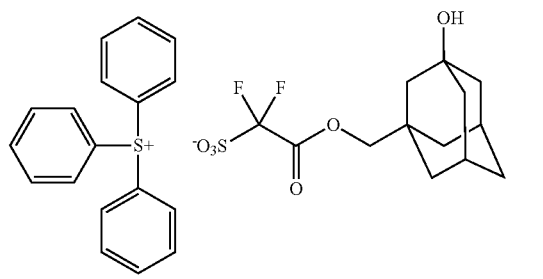

(B1-2)

<Resin>
Resin A1: 10 parts
<Nitrogen-containing Basic Compound>
Q1-1-1: 2,6-diisopropylaniline
<Solvent>

| D: | propylene glycol monomethyl ether acetate | 250 parts |
| | propylene glycol monomethyl ether | 20 parts |
| | 2-heptanone | 10 parts |
| | γ-butyrolactone | 3 parts |

The following components were mixed and dissolved, further, filtrated through a fluorine resin filter having pore diameter of 0.2 μm, to prepare photoresist compositions.
Resin: A1 10 parts
Acid generator B1-2 0.95 part
Present compound (kind and amount are described in Table 1)
Nitrogen-containing basic compound (kind and amount are described in Table 1)
Solvent D

TABLE 1

| Ex. No. | Present compound (kind/amount (part)) | Nitrogen-containing basic compound (kind/amount (part)) |
|---|---|---|
| Ex. 7 | C1-2-1/0.036 | — |
| Ex. 8 | C1-3-1/0.033 | — |
| Ex. 9 | C1-3-2/0.034 | — |
| Ex. 10 | C1-4-1/0.035 | — |
| Ex. 11 | C1-4-2/0.035 | — |
| Ex. 12 | C1-1-1/0.033 | — |
| Ref. Ex. 1 | — | Q1-1-1/0.012 |

Silicon wafers were each coated with "ARC-29SR", which is an organic anti-reflective coating composition available from Nissan Chemical Industries, Ltd., and then baked under the conditions: 205° C., 60 seconds, to form a 930 Å-thick organic anti-reflective coating. Each of the resist liquids prepared as above was spin-coated over the anti-reflective coating so that the thickness of the resulting film became 100 nm after drying. The silicon wafers thus coated with the respective resist liquids were each prebaked on a direct hotplate at 95° C. for 60 seconds. Using an ArF excimer stepper ("XT: 1900Gi" manufactured by ASML, NA-1.35, 3/4 Annular, OUTER=0.9, INNER=0.675), each wafer thus formed with the respective resist film was subjected to contact hole pattern exposure using five photomasks having pitch of 100 nm and hole diameter of 68 to 72 nm with 1 nm increments in between.

After the exposure, each wafer was subjected to post-exposure baking on a hotplate at 85° C. for 60 seconds and then to paddle development for 60 seconds with an aqueous solution of 2.38 wt % tetramethylammonium hydroxide.

Each of hole patterns developed on the organic anti-reflective coating substrate after the development was observed with a scanning electron microscope, the results of which are shown in Tables 2.

Effective Sensitivity (ES): It was expressed as the amount of exposure that hole diameter of the hole pattern became 70 nm after exposure using a mask having pitch of 100 nm and hole diameter of 70 nm and development.

Mask Error Enhancement Factor (MEEF): Hole diameters of each hole patterns exposed at ES using masks having pitch of 100 nm and hole diameter of 68 to 72 nm with 1 nm increments in between and developed were measured. MEEF was expressed as the variation of the hole diameter of the obtained hole pattern per 1 nm of the hole diameter of the used photomask. The smaller the variation is, the better MEEF is.

TABLE 2

| Ex. No. | MEEF |
|---|---|
| Ex. 7 | 2.56 |
| Ex. 8 | 2.54 |
| Ex. 9 | 2.53 |
| Ex. 10 | 3.12 |
| Ex. 11 | 2.98 |
| Ex. 12 | 2.59 |
| Ref. Ex. 1 | 3.42 |

The compound of the present invention is suitable for a component of a photoresist composition, and the photoresist composition containing the compound of the present invention provides a good resist pattern having good Mask Error Enhancement Factor, and is especially suitable for ArF excimer laser lithography, KrF excimer laser lithography and ArF immersion lithography.

What is claimed is:
1. A photoresist composition comprising a resin, an acid generator and
a compound represented by the formula (C1):

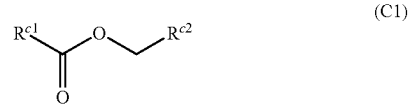

(C1)

wherein $R^{c2}$ represents a C6-C10 aromatic hydrocarbon group having at least one nitro group and the aromatic hydrocarbon group can have one or more substituents other than a nitro group, and $R^{c1}$ group represented by the formula (1):

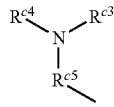
(1)

wherein $R^{c4}$ represents a hydrogen atom, or a linear, branched chain or cyclic C1-C6 aliphatic hydrocarbon group, $R^{c5}$ represents a C1-C30 divalent hydrocarbon which can have one or more substituents selected from the group consisting of a halogen atom, a hydroxyl group a mercapto group(—SH), an amino group and a carbamoyl group (—CONH$_2$), and one or more —CH$_2$— in the divalent hydrocarbon group can be replaced by —O—, —CO—, —S— or —NR$^{c15}$— in which $R^{c15}$ represents a hydrogen atom or a linear or branched chain C1-C4 alkyl group, and one or more —CH═ in the divalent hydrocarbon group can be replaced by —N═, $R^{c4}$ and $R^{c5}$ and can be bonded each other to form a ring, together with the nitrogen atom to which $R^{c4}$ and $R^{c5}$ are bonded, and $R^{c3}$ represents a group represented by the formula (3-1), (3-2), (3-3):

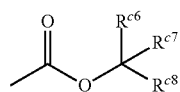
(3-1)

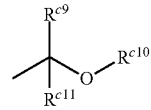
(3-2)

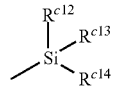
(3-3)

wherein $R^{c6}$, $R^{c7}$, $R^{c8}$, $R^{c9}$, $R^{c10}$, $R^{c11}$, $R^{c12}$, $R^{13}$ and $R^{c14}$ each independently represent a C1-C30 hydrocarbon group which can have one or more hydroxyl groups, and one or more —CH$_2$— in the C1-C30 hydrocarbon group can be replaced —O—, —CO—, —S— or —NR$^{c16}$— in which $R^{c16}$ represents a hydrogen atom or a linear or branched chain C1-C4 alkyl group and $R^{c6}$ and $R^{c7}$ can be bonded each other to form a ring together with the carbon atom to which $R^{c6}$ and $R^{c7}$ are bonded, and $R^9$ and $R^{c10}$ can be bonded each other to form a ring together with the carbon atom to which $R^{c9}$ is bonded and the oxygen atom to which $R^{c10}$ is bonded.

2. The photoresist composition according to claim 1, wherein $R^{c2}$ is a nitrophenyl group.

3. The photoresist composition according to claim 1, wherein $R^{c3}$ is a group represented by the formula (3-1).

4. The photoresist composition according to claim 1, wherein $R^{c1}$ is a group represented by the formula (1-1) or (1-2):

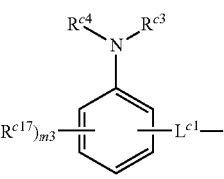
(1-1)

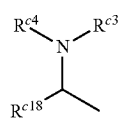
(1-2)

wherein $R^{c3}$ and $R^{c4}$ are the same as defined in claim 1, and $R^{c17}$ is independently in each occurrence a C1-C10 hydrocarbon group which can have one or more hydroxyl groups, and one or more —CH$_2$— in the C1-C10 hydrocarbon group can be replaced by —O—, —CO—, —S— or —NR$^{c19}$— in which $R^{c19}$ represents a hydrogen atom or a linear or branched chain C1-C4 alkyl group, m3 represents an integer of 0 to 4, and $L^{c1}$ represents a single bond or a linear C1-C4 alkanediyl group, $R^{c18}$ represents a hydrogen atom, a linear, branched chain or cyclic C1-C15 aliphatic hydrocarbon group or a C7-C15 aralkyl group, and one or more —CH$_2$— in the aliphatic hydrocarbon group and the aralkyl group can be replaced by —O—, —CO— or —S—, and the aliphatic hydrocarbon group and the aralkyl group can have one or more substituents selected from the group consisting of a halogen atom, a hydroxyl group, a mercapto group (—SH), an amino group and a carbamoyl group (—CONH$_2$), and $R^{c4}$ and $R^{c18}$ can be bonded each other to form a ring together with the carbon atom to which $R^{c18}$ is bonded and the nitrogen atom to which $R^{c4}$ is bonded.

5. The photoresist composition according to claim 1, wherein the compound represented by the formula (C1) is a compound represented by the formula (C1-1), (C1-2), (C1-3) or (C1-4):

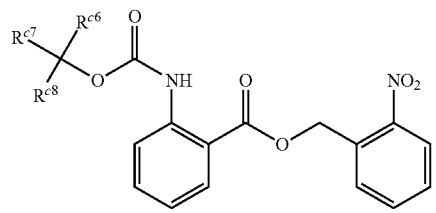
(C1-1)

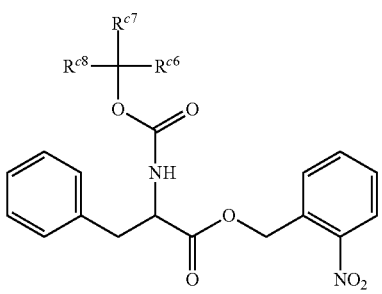
(C1-2)

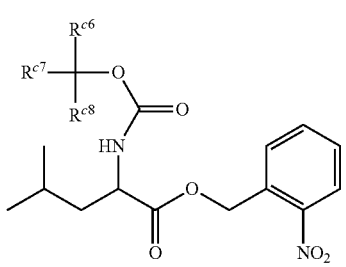
wherein $R^{c6}$, $R^{c7}$ and $R^{c8}$ are the same meanings as defined in claim 1.
* * * * *